United States Patent [19]
Jara et al.

[11] Patent Number: 6,017,762
[45] Date of Patent: Jan. 25, 2000

[54] **CASSETTE FOR THE EXPRESSION OF AN ENDOTHIAPEPSIN PRECURSOR IN *CRYPHONECTRIA PARASITICA***

[75] Inventors: Patrick Jara, Castanet-Tolosan; Richard Legoux, Caraman; Gérard Loison; Voahangy Razanamparany, both of Toulouse, all of France

[73] Assignees: Sanofi, Paris; Elf Aquitaine, Courbevoie, both of France

[21] Appl. No.: 08/115,753

[22] Filed: Sep. 3, 1993

Related U.S. Application Data

[63] Continuation of application No. 07/758,872, Sep. 11, 1991, abandoned.

[30] Foreign Application Priority Data

Sep. 11, 1990 [FR] France ................................ 9011230

[51] Int. Cl.$^7$ .............................. C12N 9/58; C12N 1/15; C12N 15/63; C07H 21/04
[52] U.S. Cl. .................... 435/484; 435/223; 435/254.11; 536/23.2; 536/23.74
[58] Field of Search ............................. 435/69.1, 172.3, 435/223, 254.11, 484, 320.1; 536/23.2, 23.1, 23.74

[56] References Cited

U.S. PATENT DOCUMENTS 3,275,453   9/1966   Sardinas ..................................... 426/36

FOREIGN PATENT DOCUMENTS

WO 89/01969   3/1989   WIPO ............................ C12N 15/00

OTHER PUBLICATIONS

James et al., *Nature* 319: 33–38 (1986).
Woolford et al., *Mol. Cel. Biol.* 6: 2500–2510 (1986).
Choi et al., *Nucleic Acids Research* 18: 18 (1990).
Mullaney et al., *Mol. Gen. Genet.* 199: 37–45 (1985).
Kozak, *Nucl. Ac. Res.* 12: 2 (1984).
Ballance, *Yeast* 2: 229–236 (1986).
Choi et al., *Phytopathology,* 80(10): 1062 (1990).
Punt et al., *Gene.* 69: 49–57 (1988).
Churchill et al., *Current Genetics* 17(1): 25–31 (1990).
Guarente, *Cell* 51: 303–305 (1988).
Frederick et al., *Mol. Gen. Genet.* 221: 148–154 (1990).
Barkholt, *Eur. J. Biochem.* 167(2): 327–338 (1987).
Wernars et al. (1987), Mol. Gen. Genet. 209: 71–77.
Jacobs et al. (1985), Nature 313: 806–810.
Sekine et al. (1969), Agr. Biol. Chem. 33(10):1477–1482.

*Primary Examiner*—David Guzo
*Attorney, Agent, or Firm*—Foley & Lardner

[57] ABSTRACT

The present invention relates to a new cassette for the expression of an endothiapepsin precursor in *Cryphonectria parasitica*, to a strain of this species transformed with this cassette, to a process for preparing endothiapepsin using this strain and also to a process for preparing such a strain devoid of a dominant selection marker.

18 Claims, 21 Drawing Sheets

FIG. 1A

SerThrGlySerAlaThrThrThrProIleAsp

SerLeuAspAspAlaTyrIleThrProValGlnIleGlyThrProAlaGlnThrLeuAsn

LeuAspPheAspThrGlySerSerAspLeuTrpValPheSerSerSerGluThrThrAlaSer

GluValAlaAspGlyGlnThrIleTyrThrProSerLysSerThrThrAlaAlaLysLeuLeuSer

GlyAlaThrTrpSerIleSerTyrGlyAspGlySerSerSerGlyAspValTyrThr

AspThrValSerValGlyGlyLeuThrValThrGlyGlnAlaValGluSerAlaAlaLys

ValSerSerSerPheThrGluAspSerThrIleAspGlyLeuLeuGlyLeuAlaPheSer

ThrLeuAsnThrValSerProThrGlnGlnLysThrPhePheAspAsnAlaAlaLysAlaSer

LeuAspSerProValPheThrAlaAspLeuGlyTyrHisAlaProGlyThrTyrAsnPhe

FIG. 1B

GlyPheIleAspThrThrAlaTyrThrGlySerIleThrTyrThrAlaValSerThrLys

GlnGlyPheTrpGluTrpThrSerThrGlyTyrAlaValGlySerGlyThrPheLysSer

ThrSerIleAspGlyIleAlaAspThrThrGlyThrThrLeuLeuTyrLeuProAlaThrVal

ValSerAlaTyrTrpAlaGlnValSerGlyAlaAlaLysSerSerSerSerValGlyGlyTyr

ValPheProCysSerAlaThrLeuProSerPheThrPheGlyValGlySerAlaArgIle

ValIleProGlyAspTyrIleAspPheGlyProIleSerThrGlySerSerSerCysPhe

GlyGlyIleGlnSerSerAlaGlyIleGlyIleAsnIlePheGlyAspValAlaLeuLys

AlaAlaPheValValPheAsnGlyAlaThrThrProThrLeuGlyPheAlaSerLys

FIG. 2A

```
   1 AAGCTTATCCGCCGCCGGGGAATTCTATTGAACTTGTTCGAATCATTGGTCCGTGG   60
     TTCGAATAGGCGGCGGCCCCCTTAAGATAACTTGAACAAGCTTAGTAACCAGGCACC

61 TCTTTTCGTCCATGCGGGCTCCGCTGGCGGATGAATGACCTTCTGGCTTCTAGCCTGGCG  120
     AGAAAAGCAGGTACGCCCGAGGCGACCGCCTACTTACTGGAAGACCGAAGATCGGACCGC

121 AAGCGATGTTACTCTGTTGTCTATACTATACGATATGGTCAAGAGAGCACATGCCGCC   180
     TTCGCTACAATGAGACAACAGATATGATATGCTATACCAGTTCTCTCGTGTACGGCGG

181 AGATGAAGACATGTATATAAAGGAGTGGCCTCGACGGTTGCTCAACCATCTTCTGTCTG   240
     TCTACTTCTGTACATATATTTCCTCACCGGAGCTGCCAACGAGTTGGTAGAAGACAGAC

241 TCCCAACGCCATCGACTCTTCAACTTCTCCTTCGTGTTCCACCACCACCTTGCTCCA    300
     AGGGTTGCGGTAGCTGAGAAGTTGAAGAGGAAGCACAAGGTGGTGGTGGAACGAGGT
                                                         BstEII
 301 GACTTAGGACTTTCAGCAACCTTCAAAGATGTCTTCCCCTCTCAAGAACGCCTTGGTGAC  360
     CTGAATCCTGAAAGTCGTTGGAAGTTTCTACAGAAGGGGAGAGTTCTTGCGGAACCACTG
         MetSerProLeuLysAsnAlaLeuValTh

361 CGCCATGTTGGCTGGTGCTCTCAGCTCGCCTACAAAGCAACAACACGTTGGAATTCCCGT  420
     GCGGTACAACCGACCACGAGAGTCGAGCGGATGTTTCGTTGTTGTGCAACCTTAAGGGCA
     rAlaMetLeuAlaGlyGlyAlaLeuSerSerProThrLysGlnHisValGlyIleProVa

421 CAACGCCTCTCCTGAAGTTGGCCCCGGAAAGTACTCGTTCAAGCAAGGTGAGTAGAGCTG  480
     GTTGCGGAGAGGACTTCAACCGGGGCCTTTCATGAGCAAGTTCGTTCCACTCATCTCGAC
     lAsnAlaSerProGluValGlyProGlyLysTyrSerPheLysGlnV

481 CTTCTGTGTTGCAACAGAACCAAGCAAAAGAAGAGGTCAAGGCAAGACGGATAT       540
     GAAGACACAACGTTGTCTTGGTTCGTTTTCTTCTCCAGTTCCGTTCTGCCTATA

541 TTTACTGACAATTATACTTTTGAAGTCCGGAACCCCAACTACAAGTTCAACGGGCCTCTG  600
     AAATGACTGTTAATATGAAAACTTCAGGCCTTGGGGTTGATGTTCAAGTTGCCCGGAGAC
     aArgAsnProAsnTyrLysPheAsnGlyProLeu
```

FIG. 2B

```
601  TCGGTCAAGAAGACGTACCTCAAGTACGGGGTGCCGATCCCAGCCTGGCTGGAGGATGCT  660
        SerValLysLysThrTyrLeuLysTyrGlyValProIleProAlaTrpLeuGluAspAla

661  GTCCAGAACTCTACCTCGGGCCTGGCTCGAGCGCTCGACCGGTTCTGCGACCACAACTCCC  720
        ValGlnAsnSerThrSerGlyLeuAlaGluArgSerAlaThrThrThrPro

721  ATCGACAGCCTGATGATGCTTACATCACTCCGGTTCAGATCGGGACCCCTGCGCAGACT  780
        IleAspSerLeuAspAspAlaTyrIleThrProValGlnIleGlyThrProAlaGlnThr

781  CTGAACCTGGACTTTGACACTGGATCTTCGGATCTGTGGGTCTTCAGCAGCGAGACTACA  840
        LeuAsnLeuAspPheAspThrGlySerSerAspLeuTrpValPheSerSerGluThrThr

841  GCCAGCGAGGTTGGTCAACCCTCGCCCCGCATTTTATTGCATACATTTTAGTTTTTTGG  900
        AlaSerGlu

901  TAATCAGAATACTAACATTGGAATTCCCAACTGTAGTCGATGGGCAGACCATCTACA  960
                                             ValAspGlyGlnThrIleTyrT

961  CCCCCAGCAAGAGCACCACCGCCAAGCTGCTGTCGGGCGCTACCTGGTCCATCTCCTACG  1020
        hrProSerLysSerThrThrAlaLysLeuLeuSerGlyAlaThrTrpSerIleSerTyrG

1021 GAGACGGTAGCTCTTCCAGCGGCGATGTCTACACTGACACCGTCTCGGTTGGAGGCCTTA  1080
        lyAspGlySerSerSerGlyAspValTyrThrAspThrValSerValGlyGlyLeuT
```

FIG. 2C

```
1081  CCGTGACGGGCCAGGCTGTCGAGTCGGCCAAGAAGGTTTCTTCCAGCTTCACCGAGGACT
      ------+---------+---------+---------+---------+---------+  1140
       hrValThrGlyGlnAlaValGluSerAlaLysLysValSerSerPheThrGluAspS

1141  CGACCATTGACGGTCTCCCTGGGCCTTCAGCACCCTGAACACTGTGTCGCCTACCC
      ------+---------+---------+---------+---------+---------+  1200
       erThrIleAspGlyLeuLeuLeuAlaPheSerThrLeuAsnThrValSerProThrG

1201  AGCAAAAGACTTTCTTCGACAATGCGAAGGCGTCCTTGGACTCGCCTGTTCACGGCTG
      ------+---------+---------+---------+---------+---------+  1260
       lnGlnLysThrPhePheAspAsnAlaLysAlaSerLeuAspSerProValPheThrAlaA

1261  ATCTTGGCTACCATGCCCGTGAGTGACCCCTCTTGATACATATACTTTTTGATGAATCTT
      ------+---------+---------+---------+---------+---------+  1320
       spLeuGlyTyrHisAlaP

1321  GTTGGAGAAGCATTCCCCACTAATATGGAAATTGTTGTATCTACAGCTGGTACTACAA
      ------+---------+---------+---------+---------+---------+  1380
                                                       roGlyThrTyrAs

1381  CTTCGGCTTCATCGATACCACTGCCTACACGGGCTCCATCACCTACACGGTGTCTCGAC
      ------+---------+---------+---------+---------+---------+  1440
       nPheGlyPheIleAspThrThrAlaTyrThrGlySerIleThrTyrThrAlaValSerTh
```

FIG. 2D

```
1441 CAAGCAAGGGTTCTGGGAGTGGACTTCGACCGGCTACGCCGTCGGCTCCGGCACCTTCAA 1500
     rLysGlnGlyPheTrpThrSerThrGlyTyrAlaValGlyLysGlyThrPheLy

1501 GTCGACTTCCATCGACGGCATGCTGACACTGGCACGACCCTCCTGTACCTCCCTGCCAC 1560
     sSerThrSerIleAspGlyIleAlaAspThrGlyThrThrLeuLeuTyrLeuProAlaTh

1561 CGTCGTGTCGGGCCTACTGGGCCCAAGTCCAGCTCTCCGGCGCTCTTCCGTCGGCGG 1620
     rValValSerAlaTyrTrpAlaGlnValSerGlyAlaAlaLysSerSerSerValGlyGl

1621 CTACGTCTTCCCCCTGCAGGCGCAGACCCCTGCCCTTCCTTCACCTTCGGGGTTGGCTCAGCTCG 1680
     yTyrValPheProCysSerAlaThrLeuProSerPheThrPheGlyValGlySerAlaAr

1681 CATTGTGATTCCTGGCGACTACATTGATTTCGGCCCCATCTCCACTGAAGCTCGTCTTG 1740
     gIleValIleProGlyAspTyrIleAspPheGlyProIleSerThrGlySerSerCy
```

FIG. 2E

```
1741 CTTTGGGGCATCCAGTCCAGGCGCTGGTATCGGCATCAACATCTTCGGTGATGTCGCTCT 1800
     sPheGlyGlyIleGlnSerSerAlaGlyIleGlyIleAsnIlePheGlyAspValAlaLe

1801 GAAGGCCGCTTTGTCGTCTTCAACGGGCTACAACTCCCACTCTTGGCTTTGCTTCCAA    1860
     uLysAlaAlaPheValValPheAsnGlyAlaThrThrProThrLeuGlyPheAlaSerLy

1861 GTAAATTAAGGGCCCTCGCTCCTCCATAGCTGCGATAAATGAGGCAGGCTCAAGTGGAAA  1920
     s

1921 GTCTTGTTGGGTAGGCGTGGATACGTATTGTCTACTTAATTAATTAATGCCAAAGCAGAC  1980

1981 CTGAAGATAGCTTTAGTAATTAATTCAATAAGCACATGGAGATCCTTCGGATCAATATGC  2040

2041 TAACTCGGTCTTCATCTCTAAACGAATGTGTTGTTGCTTGAGTTTCAGATGAATTCCTG   2100

2101 CTGTGATATCCCTCTAAGGTGTAGTATGGACAGTAAGCTT + 2140
```

FIG. 3A

MetSerSerProLeuLysAsnAlaLeuValThrAlaMetLeuAlaAlaGlyGlyAlaLeuSer

SerProThrLysGlnHisValGlyIleProValAsnAlaSerProGluValGlyProGly

LysTyrSerPheLysGlnValArgAsnProAsnTyrLysPheAsnGlyProLeuSerVal

LysLysThrTyrLeuLysTyrGlyValProIleProAlaTrpLeuGluAspAlaValGln

AsnSerThrSerGlyLeuAlaGluArgSerThrGlySerAlaThrThrThrProIleAsp

SerLeuAspAspAlaTyrIleThrProValGlnIleGlyThrProAlaGlnThrLeuAsn

LeuAspPheAspThrGlySerSerAspLeuTrpValPheSerSerGluThrThrAlaSer

GluValAspGlyGlnThrIleTyrThrProSerLysSerThrThrAlaLysLeuLeuSer

GlyAlaThrTrpSerIleSerTyrGlyAspGlySerSerSerSerGlyAspValTyrThr

AspThrValSerValGlyGlyLeuThrValThrGlyGlnAlaValGluSerAlaLysLys

ValSerSerSerPheThrGluAspSerThrIleAspGlyLeuLeuGlyLeuAlaPheSer

FIG. 3B

ThrLeuAsnThrValSerProThrGlnGlnLysThrPhePheAspAsnAlaLysAlaSer

LeuAspSerProValPheThrAlaAspLeuGlyTyrHisAlaProGlyThrTyrAsnPhe

GlyPheIleAspThrThrAlaTyrThrGlySerIleThrTyrThrAlaValSerThrLys

GlnGlyPheTrpGluTrpThrSerThrGlyTyrAlaValGlySerGlyThrPheLysSer

ThrSerIleAspGlyIleAlaAspThrGlyThrThrLeuLeuTyrLeuProAlaThrVal

ValSerAlaTyrTrpAlaGlnValSerGlyAlaLysSerSerSerValGlyGlyTyr

ValPheProCysSerAlaThrLeuProSerPheThrPheGlyValGlySerAlaArgIle

ValIleProGlyAspTyrIleAspPheGlyProIleSerThrGlySerSerSerCysPhe

GlyGlyIleGlnSerSerAlaGlyIleGlyIleAsnIlePheGlyAspValAlaLeuLys

AlaAlaPheValValPheAsnGlyAlaThrThrProThrLeuGlyPheAlaSerLys

FIG. 5A

```
  1  ATGTCTTCCC CTCTCAAGAA CGCCTTGGTG ACCGCCATGT TGGCTGGTGG
 51  TGCTCTCAGC TCGCCTACAA AGCAACACGT TGGAATTCCC GTCAACGCCT
101  CTCCTGAAGT TGGCCCCGGA AAGTACTCGT TCAAGCAAGG TGAGTAGAGC
151  TGCTTCTGTG TGTTGCAACA GAAGACCAAC GCAAAAGAA GAGGTCAAGG
201  CAAGACGGAT ATTTACTGA CAATTATACT TTTGAAGTCC GGAACCCCAA
251  CTACAAGTTC AACGGGCCTC TGTCGGTCAA GAAGACGTAC CTCAAGTACG
301  GCGTGCCGAT CCCAGCCTGG CTGGAGGATG CTGTCCAGAA CTCTACCTCG
351  GGCCTGGCTG AGCGCTCGAC CGGTTCTGCG ACCACAACTC CCATCGACAG
401  CCTCGATGAT GCTTACATCA CTCCGGTTCA GATCGGCACC CCTGCGCAGA
451  CTCTGAACCT GGACTTTGAC ACTGGATCTT CGGATCTGTG GGTCTTCAGC
```

FIG. 5B

```
501  AGCGAGACTA CAGCCAGCGA GGTTGGTCAA CCCTCGCCCG CATTTATTG
551  CATACATTTT TAGTTTTTTT GGTAATCAGA ATACTAACAT TGGGAATTTC
601  CCAACTGTAG GTCGATGGGC AGACCATCTA CACCCCCAGC AAGAGCACCA
651  CCGCCAAGCT GCTGTCGGGC GCTACCTGGT CCATCTCCTA CGGAGACGGT
701  AGCTCTTCCA GCGGCGATGT CTACACTGAC ACGGTCTCGG TTGGAGGCT
751  TACCGTGACG GGCCAGGCTG TCGAGTCGGG CAAGAAGGTT TCTTCCAGCT
801  TCACCGAGGA CTGACCATT GACGGTCTCC TGGGCCTGGC CTTCAGCACC
851  CTGAACACTG TGTCGCCTAC CCAGCAAAAG ACTTTCTTCG ACAATGCGAA
901  GGCGTCCTTG GACTCGCCTG TGTTCACGGC TGATCTTGGC TACCATGCCC
951  GTGAGTGACC CCTCTTGATA CATATACTTT TTGATGAATC TTGTTGGAGA
```

FIG. 5C

```
1001  AGCATCCCC ACTAATATGG AAATGTTTTG TATCTACAGC TGGTACCTAC
1051  AACTTCGGCT TCATCGATAC CACTGCCTAC ACGGGCTCCA TCACCTACAC
1101  CGGTGTCTCG ACCAAGCAAG GGTTCTGGGA GTGGACTTCG ACCGGCTACG
1151  CCGTCGGGCTC CGGCACCTTC AAGTCGACTT CCATCGACGG CATCGCTGAC
1201  ACTGGCACGA CCCTCCTGTA CCTCCCTGCC ACCGTCGTGT CGGCCTACTG
1251  GGCCCAGGTC TCGGGGGCCA AGTCCAGCTC TTCCGTCGGC GGCTACGTCT
1301  TCCCCTGCAG CGGCGACCCTG CCTTCCTTCA CCTTCGGCGT TGGCTCAGCT
1351  CGCATTGTGA TTCCTGGCGA CTACATTGAT TTCGGCCCCA TCTCCACTGG
1401  AAGCTCGTCT TGCTTTGGGG GCATCCAGTC CAGGCGTGGT ATCGGCATCA
1451  ACATCTTCGG TGATGTCGCT CTGAAGGCCG CCTTTGTCGT CTTCAACGGG
1501  GCTACAACTC CCACTCTTGG CTTTGCTTCC AAG
```

FIG. IIA

| | | | | |
|---|---|---|---|---|
| ATGTCTT | CCCCTCTCAA | GAACGCCTTG | GTGACCGCCA | TGTTGGCTGG |
| TGGTGCTCTC | AGCTCGCCTA | CAAAGCAACA | CGTTGGAATT | CCCGTCAACG |
| CCTCTCCTGA | AGTTGGCCCC | GGAAAGTACT | CGTTCAAGCA | AGTCCGAAC |
| CCCAACTACA | AGTTCAACGG | GCCTCTGTCG | GTCAAGAAGA | CGTACCTCAA |
| GTACGGCGTG | CCGATCCCAG | CCTGGCTGGA | GGATGCTGTC | CAGAACTCTA |
| CCTCGGGCCT | GGCTGAGCGC | TCGACCGGTT | CTGCGACCAC | AACTCCCATC |
| GACAGCCTCG | ATGATGCTTA | CATCACTCCG | GTTCAGATCG | GCACCCCTGC |
| GCAGACTCTG | AACCTGGACT | TTGACACTGG | ATCTTTCGGAT | CTGTGGGTCT |
| TCAGCAGCGA | GACTACAGCC | AGCGAGGTCG | ATGGGCAGAC | CATCTACACC |
| CCCAGCAAGA | GCACCACCGC | CAAGCTGCTG | TCGGCGCTAC | CTGGTCCATC |
| TCCTACGGAG | ACGGTAGCTC | TTCCAGCGGC | GATGTCTACA | CTGACACCGT |
| CTCGGTTGGA | GGCCTTACCG | TGACGGGCCA | GGCTGTCGAG | TCGGCCAAGA |
| AGGTTTCTTC | CAGCTTCACC | GAGGACTCGA | CCATTGACGG | TCTCCTGGGC |
| CTGGCCTTCA | GCACCCTGAA | CACTGTGTCG | CCTACCCAGC | AAAGACTTT |

FIG. 11B

```
CTTGACAAT GCGAAGGCGT CCTTGGACTC GCCTGTGTTC ACGGCTGATC
TTGGCTACCA TGCCCCTGGT ACCTACAACT TGGCTTCAT  CGATACCACT
GCCTACACGG GCTCCATCAC CTACACCGCT GTCTCGACCA AGCAAGGGTT
CTGGGAGTGG ACTTCGACCG GCTACGCCGT CGGCTCCGGC ACCTTCAAGT
CGACTTCCAT CGACGGCATC GCTGACACTG GCACGACCCT CCTGTACCTC
CCTGCCACCG TCGTGTCGGC CTACTGGGCC CAGGTCTCGG GCGCCAAGTC
CAGCTCTTCC GTCGGGGGCT ACGTCTTCCC CTGCAGCGCG ACCCTGCCTT
CCTTCACCTT CGGCGTTGGC TCAGCTCGCA TTGTGATTCC TGGCGACTAC
ATTGATTTCG GCCCCATCTC CACTGGAAGC TCGTCTTGCT TTGGGGGCAT
CCAGTCCAGC GCTGGTATCG GCATCAACAT CTTCGGTGAT GTCGCTCTGA
AGGCTTTGTC GTCTTCAACG GGGCTACAAC TCCCACTCTT GGCTTTGCTT
CCAAG
```

FIG. 12  GCATGCTTGG CTCCTTAACG TCCTGCCCAT TCAGGGCCTT CAGCCGGCAC
TGGTCCTTCA TCAAGGGGGA CCTCATGACC ATGAACTAAT CTGTGATATC
TGATATATTC TAGAAGGCTT GGCTCCTCAA AGTTTCCAGC TAATGAATCA
GCGGCCCGCC GCCCTTAAAC CGCATCAGGC AAGTCGTTTG GTGTTGCCAG
GCGATGGCGA CAGGAGAGTG GTGTTGATGG GACAAGGGGA GGGAGGCTTA
GCCGACTTCA TCCATAGCAC CCACCTGCTT GGCGCCGATA AGTCTGACGA
TCCGCTTGAG CTGCAAAACG GCTCCTTGAC CTTTGTTTGG TCGACCGAGG
GAAATAGTCT CTTTTTGCGT GATCGTGCGC GCTTCGTATA GCAATAGCAG
CCAGCACCAG CAGGACGGGC CGTTGTCACG GTCACATCGT TCGCAACATG
CCGAGCGTAG GGATGAACGA ATGACTCGAG CCTTGCCTGA CAGTCTGGCA
ATCAATCTAT GGTCACGCAC GATCACAAGC CAATCGCTGT GACTGCGTTA
CTAGCCCAAT AATCCCTTGT TCGATCAGAG TGTTCTACAG ACTTCAAGTG
AGGTTCAC

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
       (A) LENGTH: 330 amino acids
       (B) TYPE: amino acid
       (D) TOPOLOGY: linear (ii) MOLECULE TYPE: protein (iii) HYPOTHETICAL: NO (iv) ANTI-SENSE: NO (v) FRAGMENT TYPE: N-terminal (vii) IMMEDIATE SOURCE:
        (B) CLONE: endothiapepsin (xi) SEQUENCE DESCRIPTION: SEQ ID NO:1:

Ser Thr Gly Ser Ala Thr Thr Thr Pro Ile Asp Ser Leu Asp Asp Ala
   1               5                   10                  15

Tyr Ile Thr Pro Val Gln Ile Gly Thr Pro Ala Gln Thr Leu Asn Leu
                   20                  25                  30

Asp Phe Asp Thr Gly Ser Ser Asp Leu Trp Val Phe Ser Ser Glu Thr
               35                  40                  45

Thr Ala Ser Glu Val Asp Gly Gln Thr Ile Tyr Thr Pro Ser Lys Ser
           50                  55                  60

Thr Thr Ala Lys Leu Leu Ser Gly Ala Thr Trp Ser Ile Ser Tyr Gly
   65                  70                  75                  80

Asp Gly Ser Ser Ser Gly Asp Val Tyr Thr Asp Thr Val Ser Val
                   85                  90                  95

Gly Gly Leu Thr Val Thr Gly Gln Ala Val Glu Ser Ala Lys Lys Val
                   100                 105                 110

Ser Ser Ser Phe Thr Glu Asp Ser Thr Ile Asp Gly Leu Leu Gly Leu
               115                 120                 125

Ala Phe Ser Thr Leu Asn Thr Val Ser Pro Thr Gln Gln Lys Thr Phe
           130                 135                 140

Phe Asp Asn Ala Lys Ala Ser Leu Asp Ser Pro Val Phe Thr Ala Asp
   145                 150                 155                 160

```
       Leu Gly Tyr His Ala Pro Gly Thr Tyr Asn Phe Gly Phe Ile Asp Thr
                       165                 170                 175

Thr Ala Tyr Thr Gly Ser Ile Thr Tyr Thr Ala Val Ser Thr Lys Gln
                       180                 185                 190

Gly Phe Trp Glu Trp Thr Ser Thr Gly Tyr Ala Val Gly Ser Gly Thr
                       195                 200                 205

Phe Lys Ser Thr Ser Ile Asp Gly Ile Ala Asp Thr Gly Thr Thr Leu
                       210                 215                 220

Leu Tyr Leu Pro Ala Thr Val Ser Ala Tyr Trp Ala Gln Val Ser
       225                 230                 235                 240

Gly Ala Lys Ser Ser Ser Val Gly Tyr Val Phe Pro Cys Ser
                           245                 250                 255

Ala Thr Leu Pro Ser Phe Thr Phe Gly Val Gly Ser Ala Arg Ile Val
                       260                 265                 270

Ile Pro Gly Asp Tyr Ile Asp Phe Gly Pro Ile Ser Thr Gly Ser Ser
                       275                 280                 285

Ser Cys Phe Gly Gly Ile Gln Ser Ser Ala Gly Ile Gly Ile Asn Ile
                       290                 295                 300

Phe Gly Asp Val Ala Leu Lys Ala Ala Phe Val Val Phe Asn Gly Ala
       305                 310                 315                 320

Thr Thr Pro Thr Leu Gly Phe Ala Ser Lys
                       325                 330

(2) INFORMATION FOR SEQ ID NO:2:

(i) SEQUENCE CHARACTERISTICS:
        (A) LENGTH: 419 amino acids
        (B) TYPE: amino acid
        (D) TOPOLOGY: linear (ii) MOLECULE TYPE: protein (iii) HYPOTHETICAL: NO (iv) ANTI-SENSE: NO (v) FRAGMENT TYPE: N-terminal (vii) IMMEDIATE SOURCE:
        (B) CLONE: preproendothiapepsin (ix) FEATURE:
        (A) NAME/KEY: Protein
        (B) LOCATION: 90..419

(xi) SEQUENCE DESCRIPTION: SEQ ID NO:2:

Met Ser Ser Pro Leu Lys Asn Ala Leu Val Thr Ala Met Leu Ala Gly
                       -85                 -80                 -75

Gly Ala Leu Ser Ser Pro Thr Lys Gln His Val Gly Ile Pro Val Asn
                       -70                 -65                 -60

Ala Ser Pro Glu Val Gly Pro Gly Lys Tyr Ser Phe Lys Gln Val Arg
                       -55                 -50                 -45

Asn Pro Asn Tyr Lys Phe Asn Gly Pro Leu Ser Val Lys Lys Thr Tyr
                       -40                 -35                 -30

Leu Lys Tyr Gly Val Pro Ile Pro Ala Trp Leu Glu Asp Ala Val Gln
       -25                 -20                 -15                 -10

Asn Ser Thr Ser Gly Leu Ala Glu Arg Ser Thr Gly Ser Ala Thr Thr
                           -5                   1                   5

Thr Pro Ile Asp Ser Leu Asp Asp Ala Tyr Ile Thr Pro Val Gln Ile
                        10                  15                  20

Gly Thr Pro Ala Gln Thr Leu Asn Leu Asp Phe Asp Thr Gly Ser Ser
```

```
                25                  30                  35
    Asp Leu Trp Val Phe Ser Ser Glu Thr Thr Ala Ser Glu Val Asp Gly
    40                  45                  50                  55

Gln Thr Ile Tyr Thr Pro Ser Lys Ser Thr Thr Ala Lys Leu Leu Ser
                        60                  65                  70

Gly Ala Thr Trp Ser Ile Ser Tyr Gly Asp Gly Ser Ser Ser Ser Gly
                    75                  80                  85

Asp Val Tyr Thr Asp Thr Val Ser Val Gly Gly Leu Thr Val Thr Gly
                90                  95                 100

Gln Ala Val Glu Ser Ala Lys Lys Val Ser Ser Phe Thr Glu Asp
           105                 110                 115

Ser Thr Ile Asp Gly Leu Leu Gly Leu Ala Phe Ser Thr Leu Asn Thr
    120                 125                 130                 135

Val Ser Pro Thr Gln Gln Lys Thr Phe Phe Asp Asn Ala Lys Ala Ser
                        140                 145                 150

Leu Asp Ser Pro Val Phe Thr Ala Asp Leu Gly Tyr His Ala Pro Gly
                    155                 160                 165

Thr Tyr Asn Phe Gly Phe Ile Asp Thr Thr Ala Tyr Thr Gly Ser Ile
                170                 175                 180

Thr Tyr Thr Ala Val Ser Thr Lys Gln Gly Phe Trp Glu Trp Thr Ser
    185                 190                 195

Thr Gly Tyr Ala Val Gly Ser Gly Thr Phe Lys Ser Thr Ser Ile Asp
    200                 205                 210                 215

Gly Ile Ala Asp Thr Gly Thr Thr Leu Leu Tyr Leu Pro Ala Thr Val
                        220                 225                 230

Val Ser Ala Tyr Trp Ala Gln Val Ser Gly Ala Lys Ser Ser Ser Ser
                    235                 240                 245

Val Gly Gly Tyr Val Phe Pro Cys Ser Ala Thr Leu Pro Ser Phe Thr
                    250                 255                 260

Phe Gly Val Gly Ser Ala Arg Ile Val Ile Pro Gly Asp Tyr Ile Asp
        265                 270                 275

Phe Gly Pro Ile Ser Thr Gly Ser Ser Ser Cys Phe Gly Gly Ile Gln
    280                 285                 290                 295

Ser Ser Ala Gly Ile Gly Ile Asn Ile Phe Gly Asp Val Ala Leu Lys
                    300                 305                 310

Ala Ala Phe Val Val Phe Asn Gly Ala Thr Thr Pro Thr Leu Gly Phe
                315                 320                 325

Ala Ser Lys
            330
```

(2) INFORMATION FOR SEQ ID NO:3:

(i) SEQUENCE CHARACTERISTICS:
        (A) LENGTH: 1252 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: DNA coding for preproendothiapepsin having
            SEQ ID NO:2

(xi) SEQUENCE DESCRIPTION: SEQ ID NO:3:

```
ATGTCTTCCC CTCTCAAGAA CGCCTTGGTG ACCGCCATGT TGGCTGGTGG TGCTCTCAGC      60

TCGCCTACAA AGCAACACGT TGGAATTCCC GTCAACGCCT CTCCTGAAGT TGGCCCCGGA     120

AAGTACTCGT TCAAGCAAGT CCGGAACCCC AACTACAAGT TCAACGGGCC TCTGTCGGTC     180

AAGAAGACGT ACCTCAAGTA CGGCGTGCCG ATCCCAGCCT GGCTGGAGGA TGCTGTCCAG     240

AACTCTACCT CGGGCCTGGC TGAGCGCTCG ACCGGTTCTG CGACCACAAC TCCCATCGAC     300

AGCCTCGATG ATGCTTACAT CACTCCGGTT CAGATCGGCA CCCCTGCGCA GACTCTGAAC     360

CTGGACTTTG ACACTGGATC TTCGGATCTG TGGGTCTTCA GCAGCGAGAC TACAGCCAGC     420

GAGGTCGATG GGCAGACCAT CTACACCCCC AGCAAGAGCA CCACCGCCAA GCTGCTGTCG     480

GCGCTACCTG GTCCATCTCC TACGAGACG GTAGCTCTTC CAGCGGCGAT GTCTACACTG     540

ACACCGTCTC GGTTGGAGGC CTTACCGTGA CGGGCCAGGC TGTCGAGTCG GCCAAGAAGG     600

TTTCTTCCAG CTTCACCGAG GACTCGACCA TTGACGGTCT CCTGGGCCTG GCCTTCAGCA     660

CCCTGAACAC TGTGTCGCCT ACCCAGCAAA AGACTTTCTT CGACAATGCG AAGGCGTCCT     720

TGGACTCGCC TGTGTTCACG GCTGATCTTG GCTACCATGC CCCTGGTACC TACAACTTCG     780

GCTTCATCGA TACCACTGCC TACACGGGCT CCATCACCTA CACCGCTGTC TCGACCAAGC     840

AAGGGTTCTG GGAGTGGACT TCGACCGGCT ACGCCGTCGG CTCCGGCACC TTCAAGTCGA     900

CTTCCATCGA CGGCATCGCT GACACTGGCA CGACCCTCCT GTACCTCCCT GCCACCGTCG     960

TGTCGGCCTA CTGGGCCCAG GTCTCGGGCG CCAAGTCCAG CTCTTCCGTC GGCGGCTACG    1020

TCTTCCCCTG CAGCGCGACC CTGCCTTCCT TCACCTTCGG CGTTGGCTCA GCTCGCATTG    1080

TGATTCCTGG CGACTACATT GATTTCGGCC CCATCTCCAC TGGAAGCTCG TCTTGCTTTG    1140

GCGGCATCCA GTCCAGCGCT GGTATCGGCA TCAACATCTT CGGTGATGTC GCTCTGAAGG    1200

CTTTGTCGTC TTCAACGGGG CTACAACTCC CACTCTTGGC TTTGCTTCCA AG           1252

(2) INFORMATION FOR SEQ ID NO:4:

(i) SEQUENCE CHARACTERISTICS:
        (A) LENGTH: 1533 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
         (B) CLONE: DNA sequence coding for endothiapepsin (xi) SEQUENCE DESCRIPTION: SEQ ID NO:4:

ATGTCTTCCC CTCTCAAGAA CGCCTTGGTG ACCGCCATGT TGGCTGGTGG TGCTCTCAGC      60

TCGCCTACAA AGCAACACGT TGGAATTCCC GTCAACGCCT CTCCTGAAGT TGGCCCCGGA     120

AAGTACTCGT TCAAGCAAGG TGAGTAGAGC TGCTTCTGTG TGTTGCAACA GAAGACCAAC     180

GCAAAAAGAA GAGGTCAAGG CAAGACGGAT ATTTTACTGA CAATTATACT TTTGAAGTCC     240

GGAACCCCAA CTACAAGTTC AACGGGCCTC TGTCGGTCAA GAAGACGTAC CTCAAGTACG     300

GCGTGCCGAT CCCAGCCTGG CTGGAGGATG CTGTCCAGAA CTCTACCTCG GGCCTGGCTG     360

AGCGCTCGAC CGGTTCTGCG ACCACAACTC CCATCGACAG CCTCGATGAT GCTTACATCA     420

CTCCGGTTCA GATCGGCACC CCTGCGCAGA CTCTGAACCT GGACTTTGAC ACTGGATCTT     480

CGGATCTGTG GGTCTTCAGC AGCGAGACTA CAGCCAGCGA GGTTGGTCAA CCCTCGCCCG     540
```

```
CATTTTATTG CATACATTTT TAGTTTTTTT GGTAATCAGA ATACTAACAT TGGGAATTTC      600

CCAACTGTAG GTCGATGGGC AGACCATCTA CACCCCCAGC AAGAGCACCA CCGCCAAGCT      660

GCTGTCGGGC GCTACCTGGT CCATCTCCTA CGGAGACGGT AGCTCTTCCA GCGGCGATGT      720

CTACACTGAC ACCGTCTCGG TTGGAGGCCT TACCGTGACG GGCCAGGCTG TCGAGTCGGC      780

CAAGAAGGTT TCTTCCAGCT TCACCGAGGA CTCGACCATT GACGGTCTCC TGGGCCTGGC      840

CTTCAGCACC CTGAACACTG TGTCGCCTAC CCAGCAAAAG ACTTTCTTCG ACAATGCGAA      900

GGCGTCCTTG GACTCGCCTG TGTTCACGGC TGATCTTGGC TACCATGCCC GTGAGTGACC      960

CCTCTTGATA CATATACTTT TTGATGAATC TTGTTGGAGA AGCATTCCCC ACTAATATGG     1020

AAATTGTTTG TATCTACAGC TGGTACCTAC AACTTCGGCT TCATCGATAC CACTGCCTAC     1080

ACGGGCTCCA TCACCTACAC CGCTGTCTCG ACCAAGCAAG GGTTCTGGGA GTGGACTTCG     1140

ACCGGCTACG CCGTCGGCTC CGGCACCTTC AAGTCGACTT CCATCGACGG CATCGCTGAC     1200

ACTGGCACGA CCCTCCTGTA CCTCCCTGCC ACCGTCGTGT CGGCCTACTG GGCCCAGGTC     1260

TCGGGCGCCA AGTCCAGCTC TTCCGTCGGC GGCTACGTCT TCCCCTGCAG CGCGACCCTG     1320

CCTTCCTTCA CCTTCGGCGT TGGCTCAGCT CGCATTGTGA TTCCTGGCGA CTACATTGAT     1380

TTCGGCCCCA TCTCCACTGG AAGCTCGTCT TGCTTTGGCG GCATCCAGTC CAGCGCTGGT     1440

ATCGGCATCA ACATCTTCGG TGATGTCGCT CTGAAGGCCG CCTTTGTCGT CTTCAACGGG     1500

GCTACAACTC CCACTCTTGG CTTTGCTTCC AAG                                  1533

(2) INFORMATION FOR SEQ ID NO:5:

(i) SEQUENCE CHARACTERISTICS:
        (A) LENGTH: 328 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: TATA_signal
        (B) LOCATION: 1..328

(xi) SEQUENCE DESCRIPTION: SEQ ID NO:5:

AAGCTTATCC GCCGCCGGCG GGGGAATTCT ATTGAACTTG TTCGAATCAT TGGTCCGTGG       60

TCTTTTCGTC CATGCGGGCT CCGCTGGCGG ATGAATGACC TTCTGGCTTC TAGCCTGGCG      120

AAGCGATGTT ACTCTGTTGT CTATACTATA CGATATGGTC AAGAGAGCAC ATGTGCCGCC      180

AGATGAAGAC ATGTATATAA AAGGAGTGGC CTCGACGGTT GCTCAACCAT CTTCTGTCTG      240

TCCCAACGCC ATCGACTCTT CAACTTCTCC TTCGTGTTCC ACCACCATCA CCTTGCTCCA      300

GACTTAGGAC TTTCAGCAAC CTTCAAAG                                        328

(2) INFORMATION FOR SEQ ID NO:6:

(i) SEQUENCE CHARACTERISTICS:
        (A) LENGTH: 608 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO
```

(iv) ANTI-SENSE: NO (vii) IMMEDIATE SOURCE:
            (B) CLONE: segment X of fragment C having an activator
                region (xi) SEQUENCE DESCRIPTION: SEQ ID NO:6:

GCATGCTTGG CTCTTTAACG TCCTGCCCAT TCAGGGCCTT CAGCCGGCAC TGGTCCTTCA    60

TCAAGGGGGA CCTCATGACC ATGAACTAAT CTGTGATATC TGAT (i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: oligonucleotide / probe (xi) SEQUENCE DESCRIPTION: SEQ ID NO:9:

GTNGAYGGNC ARACN                                                   15

(2) INFORMATION FOR SEQ ID NO:10:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
          (B) CLONE: oligonucleotid / probe (xi) SEQUENCE DESCRIPTION: SEQ ID NO:10:

GGNTTYTGGG ARTGGACN                                                18

(2) INFORMATION FOR SEQ ID NO:11:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

ATGTCTTCCC CTCTCAAGAA CGCCTTGGTG ACCGCCATGT TGGCTGGTGG TGCTCTCAGC    60

(2) INFORMATION FOR SEQ ID NO:12:

(i) SEQUENCE CHARACTERISTICS:
          (A) LENGTH: 20 amino acids
          (B) TYPE: amino acid
          (D) TOPOLOGY: linear (ii) MOLECULE TYPE: peptide (iii) HYPOTHETICAL: NO (iv) ANTI-SENSE: NO (v) FRAGMENT TYPE: N-terminal (vii) IMMEDIATE SOURCE:
          (B) CLONE: peptide signal (xi) SEQUENCE DESCRIPTION: SEQ ID NO:12:

Met Ser Ser Pro Leu Lys Asn Ala Leu Val Thr Ala Met Leu Ala Gly
    1               5                  10                  15

Gly Ala Leu Ser
                20

(2) INFORMATION FOR SEQ ID NO:13:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: pro nucleotide sequence (xi) SEQUENCE DESCRIPTION: SEQ ID NO:13:

TCGCCTACAA AGCAACACGT TGGAATTCCC GTCAACGCCT CTCCTGAAGT TGGCCCCGGA      60

AAGTACTCGT TCAAGCAAGT CCGGAACCCC AACTACAAGT TCAACGGGCC TCTGTCGGTC     120

AAGAAGACGT ACCTCAAGTA CGGCGTGCCG ATCCCAGCCT GGCTGGAGGA TGCTGTCCAG     180

AACTCTACCT CGGGCCTGGC TGAGCGC                                         207

(2) INFORMATION FOR SEQ ID NO:14:

(i) SEQUENCE CHARACTERISTICS:
        (A) LENGTH: 69 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (vii) IMMEDIATE SOURCE:
        (B) CLONE: pro peptide sequence (xi) SEQUENCE DESCRIPTION: SEQ ID NO:14:

Ser Pro Thr Lys Gln His Val Gly Ile Pro Val Asn Ala Ser Pro Glu
    1               5                  10                  15

Val Gly Pro Gly Lys Tyr Ser Phe Lys Gln Val Arg Asn Pro Asn Tyr
                20                  25                  30

Lys Phe Asn Gly Pro Leu Ser Val Lys Lys Thr Tyr Leu Lys Tyr Gly
                35                  40                  45

Val Pro Ile Pro Ala Trp Leu Glu Asp Ala Val Gln Asn Ser Thr Ser
                50                  55                  60

Gly Leu Ala Glu Arg
    65

(2) INFORMATION FOR SEQ ID NO:15:

(i) SEQUENCE CHARACTERISTICS:
        (A) LENGTH: 89 amino acids
        (B) TYPE: amino acid
        (D) TOPOLOGY: linear (ii) MOLECULE TYPE: peptide (iii) HYPOTHETICAL: NO (iv) ANTI-SENSE: NO (v) FRAGMENT TYPE: N-terminal (vii) IMMEDIATE SOURCE:
             (B) CLONE: prepro peptide sequence (xi) SEQUENCE DESCRIPTION: SEQ ID NO:15:

Met Ser Ser Pro Leu Lys Asn Ala Leu Val Thr Ala Met Leu Ala Gly
    1               5                   10                  15

Gly Ala Leu Ser Ser Pro Thr Lys Gln His Val Gly Ile Pro Val Asn
                    20                  25                  30

Ala Ser Pro Glu Val Gly Pro Gly Lys Tyr Ser Phe Lys Gln Val Arg
                35                  40                  45

Asn Pro Asn Tyr Lys Phe Asn Gly Pro Leu Ser Val Lys Lys Thr Tyr
                50                  55                  60

Leu Lys Tyr Gly Val Pro Ile Pro Ala Trp Leu Glu Asp Ala Val Gln
    65                  70                  75                  80

Asn Ser Thr Ser Gly Leu Ala Glu Arg
                    85

(2) INFORMATION FOR SEQ ID NO:16:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
             (B) CLONE: Start of natural seq. coding for precursor of
                 endothiapepsin (xi) SEQUENCE DESCRIPTION: SEQ ID NO:16:

GATGTCTTCC CCTCTCAAGA ACGCCTTGGT GACC                                     34

(2) INFORMATION FOR SEQ ID NO:17:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
             (B) CLONE: Fragment EM in which the sequence coding for
                 endothiapepsin (xi) SEQUENCE DESCRIPTION: SEQ ID NO:17:

GATGTCTTCC CCTCTCTAAT GAACGCCTTG GTGACC                                   36

(2) INFORMATION FOR SEQ ID NO:18:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide (xi) SEQUENCE DESCRIPTION: SEQ ID NO:18:

GCTAAAGCTT ATCCGCCGCC GGCGGGGGAA TTC                                    33

(2) INFORMATION FOR SEQ ID NO:19:

(i) SEQUENCE CHARACTERISTICS:
       (A) LENGTH: 46 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide (xi) SEQUENCE DESCRIPTION: SEQ ID NO:19:

CAATGGATCC GGTCACCAAG GCGTTCATTA GAGAGGGGAA GACATC                      46

(2) INFORMATION FOR SEQ ID NO:20:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide /primer 5' carrying site NcoI (xi) SEQUENCE DESCRIPTION: SEQ ID NO:20:

ACGTCCATGG CTTCCCCTCT CAAGAACGCC                                        30

(2) INFORMATION FOR SEQ ID NO:21:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide / primer 3' carrying site MluI (xi) SEQUENCE DESCRIPTION: SEQ ID NO:21:

ACGTACGCGT CCACGCCTAC CCAACAAGAC                                30

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide / primer 1

(xi) SEQUENCE DESCRIPTION: SEQ ID NO:22:

AGAAAGCTTG GAGGAGCGAG GGCCC                                     25

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide / primer 2

(xi) SEQUENCE DESCRIPTION: SEQ ID NO:23:

GCAGAATTCA CATATGTCTT CCCCTCTCAA G                              31

(2) INFORMATION FOR SEQ ID NO:24:

(i) SEQUENCE CHARACTERISTICS:
        (A) LENGTH: 1236 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: Fragment 3:synthetic fragment
            BamHI(1)-BamHI(2) containing (xi) SEQUENCE DESCRIPTION: SEQ ID NO:24:

GATCCGCGGA AGCATAAAGT GTAAAGCCTG GGGTGCCTAA TGAGTGAGCT AACTTACATT      60

AATTGCGTTG CGCTCACTGC CCGCTTTCCA GTCGGGAAAC CTGTCGTGCC AGCTGCATTA     120

ATGAATCGGC CAACGCGCGG GGAGAGGCGG TTTGCGTATT GGGCGCCAGG GTGGTTTTTC     180

TTTTCACCAG TGAGACGGGC AACAGCTGAT TGCCCTTCAC CGCCTGGCCC TGAGAGAGTT     240

GCAGCAAGCG GTCCACGCTG GTTTGCCCCA CCACCCGAAA ATCCTGTTTG ATGGTGGTTA     300

```
ACGGCGGGAT ATAACATGAG CTGTCTTCGG TATCGTCGTA TCCCACTACC GAGATATCCG    360

CACCAACGCG CAGCCCGGAC TCGGTAATGG CGCGCATTGC GCCCAGCGCC ATCTGATCGT    420

TGGCAACCAG CATCGCAGTG GGAACGATGC CCTCATTCAG CATTTGCATG GTTTGTTGAA    480

AACCGGACAT GGCACTCCAG TCGCCTTCCC GTTCCGCTAT CGGCTGAATT TGATTGCGAG    540

TGAGATATTT ATGCCAGCCA GCCAGACGCA GACGCGCCGA GACAGAACTT AATGGGCCCG    600

CTAACAGCGC GATTTGCTGG TGACCCAATG CGACCAGATG CTCCACGCCC AGTCGCGTAC    660

CGTCTTCATG GGAGAAAATA ATACTGTTGA TGGGTGTCTG GTCAGAGACA TCAAGAAATA    720

ACGCCGGAAC ATTAGTGCAG GCAGCTTCCA CAGCAATGGC ATCCTGGTCA TCCAGCGGAT    780

AGTTAATGAT CAGCCCACTG ACGCGTTGCG CGAGAAGATT GTGCACCGCC GCTTTACAGG    840

CTTCGACGCC GCTTCGTTCT ACCATCGACA CCACCACGCT GGCACCCAGT TGATCGGCGC    900

GAGATTTAAT CGCCGCGACA ATTTGCGACG GCGCGTGCAG GGCCAGACTG GAGGTGGCAA    960

CGCCAATCAG CAACGACTGT TTGCCCGCCA GTTGTTGTGC CACGCGGTTG GGAATGTAAT   1020

TCAGCTCCGC CATCGCCGCT TCCACTTTTT CCCGCGTTTT CGCAGAAACG TGGCTGGCCT   1080

GGTTCACCAC GCGGGAAACG GTCTGATAAC AGACACCGGC ATACTCTGCG ACATCGTATA   1140

ACGTTACTGG TTTCACATTC ACCACCCTGA ATTGACTCTC TTCCGGGCGC TATCATGCCA   1200

TACCGCGAAA GGTTTTGCGC CATTCGATGG TGTCCG                             1236
```

(2) INFORMATION FOR SEQ ID NO:25:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: -35_signal
        (B) LOCATION: 18..23

(ix) FEATURE:
        (A) NAME/KEY: -10_signal
        (B) LOCATION: 41..46

(ix) FEATURE:
        (A) NAME/KEY: sig_peptide
        (B) LOCATION: 107..184

(ix) FEATURE:
        (A) NAME/KEY: mat_peptide
        (B) LOCATION: 185..316

(ix) FEATURE:
        (A) NAME/KEY: CDS
        (B) LOCATION: 107..316

(xi) SEQUENCE DESCRIPTION: SEQ ID NO:25:

```
TCGAGCTGAC TGACCTGTTG CTTATATTAC ATCGATAGCG TATAATGTGT GGAATTGTGA     60

GCGATAACAA TTTCACACAG TTTAACTTTA AGAAGGAGAT ATACAT ATG GCT ACC       115
                                                 Met Ala Thr
                                                 -26 -25

GGA TCC CGG ACT AGT CTG CTC CTG GCT TTT GGC CTG CTC TGC CTG CCC       163
Gly Ser Arg Thr Ser Leu Leu Leu Ala Phe Gly Leu Leu Cys Leu Pro
       -20              -15              -10
```

```
TGG CTT CAA GAG GGC AGT GCC TTC CCA ACC ATT CCC TTA TCT AGA CTT      211
Trp Leu Gln Glu Gly Ser Ala Phe Pro Thr Ile Pro Leu Ser Arg Leu
        -5                   1                   5

TTT GAC AAC GCT ATG CTC CGC GCC CAT CGT CTG CAC CAG CTG GCC TTT      259
Phe Asp Asn Ala Met Leu Arg Ala His Arg Leu His Gln Leu Ala Phe
 10              15                  20                  25

GAC ACC TAC CAG GAG TTT GAA GAA GCC TAT ATC CCA AAG GAA CAG AAG      307
Asp Thr Tyr Gln Glu Phe Glu Glu Ala Tyr Ile Pro Lys Glu Gln Lys
            30                  35                  40

TAT TCA TTC CTGCA                                                    321
Tyr Ser Phe
```

(2) INFORMATION FOR SEQ ID NO:26:

(i) SEQUENCE CHARACTERISTICS:
        (A) LENGTH: 70 amino acids
        (B) TYPE: amino acid
        (D) TOPOLOGY: linear (ii) MOLECULE TYPE: protein (xi) SEQUENCE DESCRIPTION: SEQ ID NO:26:

```
Met Ala Thr Gly Ser Arg Thr Ser Leu Leu Ala Phe Gly Leu Leu
-26 -25                 -20                 -15

Cys Leu Pro Trp Leu Gln Glu Gly Ser Ala Phe Pro Thr Ile Pro Leu
-10                 -5                  1                   5

Ser Arg Leu Phe Asp Asn Ala Met Leu Arg Ala His Arg Leu His Gln
                10                  15                  20

Leu Ala Phe Asp Thr Tyr Gln Glu Phe Glu Glu Ala Tyr Ile Pro Lys
            25                  30                  35

Glu Gln Lys Tyr Ser Phe
            40
```

(2) INFORMATION FOR SEQ ID NO:27:

(i) SEQUENCE CHARACTERISTICS:
        (A) LENGTH: 74 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

```
CGATAGCGTA TAATGTGTGG AATTGTGAGC GGATAACAAT TTCACACAGT TTTTCGCGAA    60

GAAGGAGATA TACA                                                     74
```

(2) INFORMATION FOR SEQ ID NO:28:

(i) SEQUENCE CHARACTERISTICS:
        (A) LENGTH: 190 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

```
GATCTTCAAG CAGACCTACA GCAAGTTCGA CACAAACTCA CACAACGATG ACGCACTACT      60

CAAGAACTAC GGGCTGCTCT ACTGCTTCAG GAAGGACATG GACAAGGTCG AGACATTCCT     120

GCGCATCGTG CAGTGCCGCT CTGTGGAGGG CAGCTGTGGC TTCTAGTAAG GTACCCTGCC     180

CTACGTACCA                                                           190
```

(2) INFORMATION FOR SEQ ID NO:29:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide complementary to SEQ ID NO:30

(xi) SEQUENCE DESCRIPTION: SEQ ID NO:29:

```
TATGTCTGCG GTAAAAGCAG CGCGCTACGG CAAGGACAAT GTTCGCGT                  48
```

(2) INFORMATION FOR SEQ ID NO:30:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: oligonucleotide complementary to SEQ ID NO:29

(xi) SEQUENCE DESCRIPTION: SEQ ID NO:30:

```
AGACGCGAAC ATTGTCCTTG CCGTAGCGCG CTGCTTTTAC CGCAGACA                  48
```

(2) INFORMATION FOR SEQ ID NO:31:

(i) SEQUENCE CHARACTERISTICS:
        (A) LENGTH: 906 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

```
ATGTCTGCGG TAAAAGCAGC GCGCTACGGC AAGGACAATG TTCGCGTCTA CAAGGTTCAC      60

AAGGACGAGA AGACCGGTGT CCAGACGGTG TACGAGATGA CCGTCTGTGT GCTTCTGGAG     120

GGTGAGATTG AGACCTCTTA CACCAAGGCC GACAACAGCG TCATTGTCGC AACCGACTCC     180

ATTAAGAACA CCATTTACAT CACCGCCAAG CAGAACCCCG TTACTCCTCC CGAGCTGTTC     240

GGCTCCATCC TGGGCACACA CTTCATTGAG AAGTACAACC ACATCCATGC CGCTCACGTC     300

AACATTGTCT GCCACCGCTG GACCCGGATG GACATTGACG GCAAGCCACA CCCTCACTCC     360
```

```
TTCATCCGCG ACAGCGAGGA GAAGCGGAAT GTGCAGGTGG ACGTGGTCGA GGGCAAGGGC      420

ATCGATATCA AGTCGTCTCT GTCCGGCCTG ACCGTGCTGA AGAGCACCAA CTCGCAGTTC      480

TGGGGCTTCC TGCGTGACGA GTACACCACA CTTAAGGAGA CCTGGGACCG TATCCTGAGC      540

ACCGACGTCG ATGCCACTTG GCAGTGGAAG AATTTCAGTG GACTCCAGGA GGTCCGCTCG      600

CACGTGCCTA AGTTCGATGC TACCTGGGCC ACTGCTCGCG AGGTCACTCT GAAGACTTTT      660

GCTGAAGATA ACAGTGCCAG CGTGCAGGCC ACTATGTACA AGATGGCAGA GCAAATCCTG      720

GCGCGCCAGC AGCTGATCGA GACTGTCGAG TACTCGTTGC CTAACAAGCA CTATTTCGAA      780

ATCGACCTGA GCTGGCACAA GGGCCTCCAA AACACCGGCA AGAACGCCGA GGTCTTCGCT      840

CCTCAGTCGG ACCCCAACGG TCTGATCAAG TGTACCGTCG GCCGGTCCTC TCTGAAGTCT      900

AAATTG                                                                906
```

(2) INFORMATION FOR SEQ ID NO:32:

(i) SEQUENCE CHARACTERISTICS:
        (A) LENGTH: 2140 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: base pairs 402-405 : site BstIII (ix) FEATURE:
        (A) NAME/KEY: intron
        (B) LOCATION: 468..565
        (D) OTHER INFORMATION: /standard_name= "intron 1"

(ix) FEATURE:
        (A) NAME/KEY: intron
        (B) LOCATION: 850..938
        (D) OTHER INFORMATION: /standard_name= "intron 2"

(ix) FEATURE:
        (A) NAME/KEY: intron
        (B) LOCATION: 1279..1367
        (D) OTHER INFORMATION: /standard_name= "intron 3"

(ix) FEATURE:
        (A) NAME/KEY: sig_peptide
        (B) LOCATION: join(329..467, 566..693)

(ix) FEATURE:
        (A) NAME/KEY: mat_peptide
        (B) LOCATION: join(694..849, 939..1278, 1368..1861)

(ix) FEATURE:
        (A) NAME/KEY: CDS
        (B) LOCATION: join(329..467, 566..849, 939..1278, 1368..1861)

(xi) SEQUENCE DESCRIPTION: SEQ ID NO:32:

```
AAGCTTATCC GCCGCCGGCG GGGGAATTCT ATTGAACTTG TTCGAATCAT TGGTCCGTGG       60

TCTTTTCGTC CATGCGGGCT CCGCTGGCGG ATGAATGACC TTCTGGCTTC TAGCCTGGCG      120

AAGCGATGTT ACTCTGTTGT CTATACTATA CGATATGGTC AAGAGAGCAC ATGTGCCGCC      180

AGATGAAGAC ATGTATATAA AAGGAGTGGC CTCGACGGTT GCTCAACCAT CTTCTGTCTG      240

TCCCAACGCA ATCGACTCTT CAACTTCTCC TTCGTGTTCC ACCACCATCA CCTTGCTCCA      300

GACTTAGGAC TTTCAGCAAC CTTCAAAG ATG TCT TCC CCT CTC AAG AAC GCC        352
                                Met Ser Ser Pro Leu Lys Asn Ala
```

|  |  |
|---|---|
|                              -89                       -85 | |
| TTG GTG ACC GCC ATG TTG GCT GGT GGT GCT CTC AGC TCG CCT ACA AAG<br>Leu Val Thr Ala Met Leu Ala Gly Gly Ala Leu Ser Ser Pro Thr Lys<br>    -80                      -75                       -70 | 400 |
| CAA CAC GTT GGA ATT CCC GTC AAC GCC TCT CCT GAA GTT GGC CCC GGA<br>Gln His Val Gly Ile Pro Val Asn Ala Ser Pro Glu Val Gly Pro Gly<br>-65                  -60                    -55                  -50 | 448 |
| AAG TAC TCG TTC AAG CAA  G GTGAGTAGAG CTGCTTCTGT GTGTTGCAAC<br>Lys Tyr Ser Phe Lys Gln<br>                -45 | 497 |
| AGAAGACCAA CGCAAAAAGA AGAGGTCAAG GCAAGACGGA TATTTTACTG ACAATTATAC | 557 |
| TTTTGAAG  TC CGG AAC CCC AAC TAC AAG TTC AAC GGG CCT CTG TCG GTC<br>               Val Arg Asn Pro Asn Tyr Lys Phe Asn Gly Pro Leu Ser Val<br>                 -42     -40                -35                   -30 | 606 |
| AAG AAG ACG TAC CTC AAG TAC GGC GTG CCG ATC CCA GCC TGG CTG GAG<br>Lys Lys Thr Tyr Leu Lys Tyr Gly Val Pro Ile Pro Ala Trp Leu Glu<br>           -25                    -20                    -15 | 654 |
| GAT GCT GTC CAG AAC TCT ACC TCG GGC CTG GCT GAG CGC TCG ACC GGT<br>Asp Ala Val Gln Asn Ser Thr Ser Gly Leu Ala Glu Arg Ser Thr Gly<br>        -10                   -5                        1 | 702 |
| TCT GCG ACC ACA ACT CCC ATC GAC AGC CTC GAT GAT GCT TAC ATC ACT<br>Ser Ala Thr Thr Thr Pro Ile Asp Ser Leu Asp Asp Ala Tyr Ile Thr<br>  5                      10                   15 | 750 |
| CCG GTT CAG ATC GGC ACC CCT GCG CAG ACT CTG AAC CTG GAC TTT GAC<br>Pro Val Gln Ile Gly Thr Pro Ala Gln Thr Leu Asn Leu Asp Phe Asp<br> 20                  25                  30                35 | 798 |
| ACT GGA TCT TCG GAT CTG TGG GTC TTC AGC AGC GAG ACT ACA GCC AGC<br>Thr Gly Ser Ser Asp Leu Trp Val Phe Ser Ser Glu Thr Thr Ala Ser<br>               40                    45                   50 | 846 |
| GAG GTTGGTCAAC CCTCGCCCGC ATTTTATTGC ATACATTTTT AGTTTTTTTG<br>Glu | 899 |
| GTAATCAGAA TACTAACATT GGGAATTTCC CAACTGTAG GTC GAT GGG CAG ACC<br>                                                         Val Asp Gly Gln Thr<br>                                                            55 | 953 |
| ATC TAC ACC CCC AGC AAG AGC ACC ACC GCC AAG CTG CTG TCG GGC GCT<br>Ile Tyr Thr Pro Ser Lys Ser Thr Thr Ala Lys Leu Leu Ser Gly Ala<br>        60                    65                    70 | 1001 |
| ACC TGG TCC ATC TCC TAC GGA GAC GGT AGC TCT TCC AGC GGC GAT GTC<br>Thr Trp Ser Ile Ser Tyr Gly Asp Gly Ser Ser Ser Ser Gly Asp Val<br> 75                   80                    85 | 1049 |
| TAC ACT GAC ACC GTC TCG GTT GGA GGC CTT ACC GTG ACG GGC CAG GCT<br>Tyr Thr Asp Thr Val Ser Val Gly Gly Leu Thr Val Thr Gly Gln Ala<br> 90                   95                  100              105 | 1097 |
| GTC GAG TCG GCC AAG AAG GTT TCT TCC AGC TTC ACC GAG GAC TCG ACC<br>Val Glu Ser Ala Lys Lys Val Ser Ser Ser Phe Thr Glu Asp Ser Thr<br>           110                   115                 120 | 1145 |
| ATT GAC GGT CTC CTG GGC CTG GCC TTC AGC ACC CTG AAC ACT GTG TCG<br>Ile Asp Gly Leu Leu Gly Leu Ala Phe Ser Thr Leu Asn Thr Val Ser<br>          125                   130                 135 | 1193 |
| CCT ACC CAG CAA AAG ACT TTC TTC GAC AAT GCG AAG GCG TCC TTG GAC<br>Pro Thr Gln Gln Lys Thr Phe Phe Asp Asn Ala Lys Ala Ser Leu Asp<br>          140                   145                 150 | 1241 |
| TCG CCT GTG TTC ACG GCT GAT CTT GGC TAC CAT GCC  C GTGAGTGACC<br>Ser Pro Val Phe Thr Ala Asp Leu Gly Tyr His Ala<br>          155                   160                 165 | 1288 |
| CCTCTTGATA CATATACTTT TTGATGAATC TTGTTGGAGA AGCATTCCCC ACTAATATGG | 1348 |
| AAATTGTTTG TATCTACAG  CT GGT ACC TAC AAC TTC GGC TTC ATC GAT ACC<br>                               Pro Gly Thr Tyr Asn Phe Gly Phe Ile Asp Thr<br>                                        170                   175 | 1399 |

-continued

| | |
|---|---|
| ACT GCC TAC ACG GGC TCC ATC ACC TAC ACC GCT GTC TCG ACC AAG CAA<br>Thr Ala Tyr Thr Gly Ser Ile Thr Tyr Thr Ala Val Ser Thr Lys Gln<br>          180                    185                    190 | 1447 |
| GGG TTC TGG GAG TGG ACT TCG ACC GGC TAC GCC GTC GGC TCC GGC ACC<br>Gly Phe Trp Glu Trp Thr Ser Thr Gly Tyr Ala Val Gly Ser Gly Thr<br>          195                    200                    205 | 1495 |
| TTC AAG TCG ACT TCC ATC GAC GGC ATC GCT GAC ACT GGC ACG ACC CTC<br>Phe Lys Ser Thr Ser Ile Asp Gly Ile Ala Asp Thr Gly Thr Thr Leu<br>          210                    215                    220 | 1543 |
| CTG TAC CTC CCT GCC ACC GTC GTG TCG GCC TAC TGG GCC CAG GTC TCG<br>Leu Tyr Leu Pro Ala Thr Val Val Ser Ala Tyr Trp Ala Gln Val Ser<br>225                    230                    235                    240 | 1591 |
| GGC GCC AAG TCC AGC TCT TCC GTC GGC GGC TAC GTC TTC CCC TGC AGC<br>Gly Ala Lys Ser Ser Ser Ser Val Gly Gly Tyr Val Phe Pro Cys Ser<br>                    245                    250                    255 | 1639 |
| GCG ACC CTG CCT TCC TTC ACC TTC GGC GTT GGC TCA GCT CGC ATT GTG<br>Ala Thr Leu Pro Ser Phe Thr Phe Gly Val Gly Ser Ala Arg Ile Val<br>          260                    265                    270 | 1687 |
| ATT CCT GGC GAC TAC ATT GAT TTC GGC CCC ATC TCC ACT GGA AGC TCG<br>Ile Pro Gly Asp Tyr Ile Asp Phe Gly Pro Ile Ser Thr Gly Ser Ser<br>          275                    280                    285 | 1735 |
| TCT TGC TTT GGC GGC ATC CAG TCC AGC GCT GGT ATC GGC ATC AAC ATC<br>Ser Cys Phe Gly Gly Ile Gln Ser Ser Ala Gly Ile Gly Ile Asn Ile<br>          290                    295                    300 | 1783 |
| TTC GGT GAT GTC GCT CTG AAG GCC GCC TTT GTC GTC TTC AAC GGG GCT<br>Phe Gly Asp Val Ala Leu Lys Ala Ala Phe Val Val Phe Asn Gly Ala<br>305                    310                    315                    320 | 1831 |
| ACA ACT CCC ACT CTT GGC TTT GCT TCC AAG TAAATTAAGG GCCCTCGCTC<br>Thr Thr Pro Thr Leu Gly Phe Ala Ser Lys<br>                          325                    330 | 1881 |
| CTCCATAGCT GCGATAAATG AGGCAGGCTC AAGTGGAAAG TCTTGTTGGG TAGGCGTGGA | 1941 |
| TACGTATTGT CTACTTAATT AATTAATGCC AAAGCAGACC TGAAGATAGC TTTAGTAATT | 2001 |
| AATTCAATAA GCACATGGAG ATCCTTCGGA TCAATATGCT AACTCGGTCT TCATCTCTAA | 2061 |
| ACGAATGTGT TGTTGCTTGA GTTTCAGATG AATTTCCTGC TGTGATATCC CTCTAAGGTG | 2121 |
| TAGTATGGAC AGTAAGCTT | 2140 |

(2) INFORMATION FOR SEQ ID NO:33:

(i) SEQUENCE CHARACTERISTICS:
        (A) LENGTH: 419 amino acids
        (B) TYPE: amino acid
        (D) TOPOLOGY: linear (ii) MOLECULE TYPE: protein (xi) SEQUENCE DESCRIPTION: SEQ ID NO:33:

Met Ser Ser Pro Leu Lys Asn Ala Leu Val Thr Ala Met Leu Ala Gly
-89                  -85                  -80                  -75

Gly Ala Leu Ser Ser Pro Thr Lys Gln His Val Gly Ile Pro Val Asn
              -70                  -65                  -60

Ala Ser Pro Glu Val Gly Pro Gly Lys Tyr Ser Phe Lys Gln Val Arg
        -55                  -50                  -45                  -42

Asn Pro Asn Tyr Lys Phe Asn Gly Pro Leu Ser Val Lys Lys Thr Tyr
        -40                  -35                  -30

Leu Lys Tyr Gly Val Pro Ile Pro Ala Trp Leu Glu Asp Ala Val Gln
-25                  -20                  -15                  -10

Asn Ser Thr Ser Gly Leu Ala Glu Arg Ser Thr Gly Ser Ala Thr Thr
              -5                    1                     5

```
Thr Pro Ile Asp Ser Leu Asp Asp Ala Tyr Ile Thr Pro Val Gln Ile
        10              15                  20

Gly Thr Pro Ala Gln Thr Leu Asn Leu Asp Phe Asp Thr Gly Ser Ser
    25                  30                  35

Asp Leu Trp Val Phe Ser Ser Glu Thr Thr Ala Ser Glu Val Asp Gly
40                  45                  50                  55

Gln Thr Ile Tyr Thr Pro Ser Lys Ser Thr Thr Ala Lys Leu Leu Ser
            60                  65                      70

Gly Ala Thr Trp Ser Ile Ser Tyr Gly Asp Gly Ser Ser Ser Ser Gly
                75                  80                  85

Asp Val Tyr Thr Asp Thr Val Ser Val Gly Gly Leu Thr Val Thr Gly
        90                  95                  100

Gln Ala Val Glu Ser Ala Lys Lys Val Ser Ser Ser Phe Thr Glu Asp
    105             110                 115

Ser Thr Ile Asp Gly Leu Leu Gly Leu Ala Phe Ser Thr Leu Asn Thr
120             125                 130                 135

Val Ser Pro Thr Gln Gln Lys Thr Phe Phe Asp Asn Ala Lys Ala Ser
            140                 145                 150

Leu Asp Ser Pro Val Phe Thr Ala Asp Leu Gly Tyr His Ala Pro Gly
            155                 160                 165

Thr Tyr Asn Phe Gly Phe Ile Asp Thr Thr Ala Tyr Thr Gly Ser Ile
170             175                 180

Thr Tyr Thr Ala Val Ser Thr Lys Gln Gly Phe Trp Glu Trp Thr Ser
    185                 190                 195

Thr Gly Tyr Ala Val Gly Ser Gly Thr Phe Lys Ser Thr Ser Ile Asp
200                 205                 210                 215

Gly Ile Ala Asp Thr Gly Thr Thr Leu Leu Tyr Leu Pro Ala Thr Val
                220                 225                 230

Val Ser Ala Tyr Trp Ala Gln Val Ser Gly Ala Lys Ser Ser Ser Ser
            235                 240                 245

Val Gly Gly Tyr Val Phe Pro Cys Ser Ala Thr Leu Pro Ser Phe Thr
            250                 255                 260

Phe Gly Val Gly Ser Ala Arg Ile Val Ile Pro Gly Asp Tyr Ile Asp
265                 270                 275

Phe Gly Pro Ile Ser Thr Gly Ser Ser Ser Cys Phe Gly Gly Ile Gln
280                 285                 290                 295

Ser Ser Ala Gly Ile Gly Ile Asn Ile Phe Gly Asp Val Ala Leu Lys
                300                 305                 310

Ala Ala Phe Val Val Phe Asn Gly Ala Thr Thr Pro Thr Leu Gly Phe
            315                 320                 325

Ala Ser Lys
    330
```

CASSETTE FOR THE EXPRESSION OF AN ENDOTHIAPEPSIN PRECURSOR IN *CRYPHONECTRIA PARASITICA*

This application is a continuation of application Ser. No. 07/758,872, filed Sep. 11, 1991, now abandoned.

The present invention relates to a new cassette for the expression of an endothiapepsin precursor in *Cryphonectria parasitica,* to a strain of this species transformed with this cassette, to a process for preparing endothiapepsin using this strain and also to a process for preparing such a strain devoid of a dominant selection marker.

The filamentous fungus *Cryphonectria parasitica,* also known as *Endothia parasitica,* which belongs to the Ascomycetes group, naturally secretes an aspartic protease, namely endothiapepsin, capable of curdling milk by specifically hydrolysing the micelles of casein, and which is hence useful in the manufacture of certain cheeses, especially cooked cheeses of the Emmental type. This enzyme, whose sequence of 330 amino acids has been described by Barkolt V., 1987, Eur. J. Biochem. 167, 327–338, then replaces chymosin.

This enzyme is currently produced on an industrial scale by processes of fermentation of *Cryphonectria parasitica* strains chosen for their good level of expression of endothiapepsin.

These processes possess drawbacks, and in particular that of an immobilisation of a large reactor volume, since the quantity of endothiapepsin per unit of biomass, and hence the quantity of endothiapepsin per unit of reactor volume for a given quantity of biomass, is low.

Conventional mutation/selection techniques enable the quantity of endothiapepsin produced per unit of biomass to be increased by only approximately 30%.

There is hence a need for genetic engineering tools enabling *Cryphonectria parasitica* strains to be obtained which are overproductive of endothiapepsin with a large overproduction factor. The latter is defined here as the ratio of the quantity of endothiapepsin produced by the overproductive transformed strain to the quantity of this protein produced by the untransformed control strain, for the same quantity of biomass.

*Cryphonectria parasitica* is a filamentous fungus whose genetics is still very little known, in contrast to that of other filamentous fungi of the Ascomycetes group such as those of the genus Aspergillus, Neurospora or Trichoderma. Only very recently have the first transformations of Cryphonectria been described, by Churchill et al. 1990, Curr. Gen, 17, 25–31. These authors transformed laboratory strains of Cryphonectria using plasmids carrying markers for resistance to hygromycin, benomyl or G 418. No protein of commercial interest has ever been produced hitherto using a Cryphonectria recombined by genetic engineering.

Recently, at the Congress: "Annual Meeting of the American Phytopathological Society and the Canadian Phytopathological Society", Aug. 4th to 8th 1990, G. H. Choi et al. presented—apparently (according to the published abstract of their communication)—the coding sequence of endothiapepsin, an assumed prepro sequence of 88 amino acids and a portion of the endothiapepsin promoter comprising the TATA box but not the activator regions necessary for the promoter to be able to function. Such a genomic DNA fragment, but containing a prepro sequence of 89 amino acids, had already been isolated and sequenced by the Applicant in 1989, who had observed that it does not permit the expression of endothiapepsin (see Sections 1 and 6 below).

The present invention relates to a new cassette for the expression of an endothiapepsin precursor in *Cryphonectria parasitica,* characterised in that it comprises a functional promoter upstream of a sequence coding for the endothiapepsin precursor, endothiapepsin having the following sequence (P1)(SEQ ID NO:1):

```
Ser Thr Gly Ser Ala Thr Thr Thr Pro Ile Asp Ser Leu Asp Asp Ala Tyr
Ile Thr Pro Val Gln Ile Gly Thr Pro Ala Gln Thr Leu Asn Leu Asp Phe
Asp Thr Gly Ser Ser Asp Leu Trp Val Phe Ser Ser Glu Thr Thr Ala Ser
Glu Val Asp Gly Gln Thr Ile Tyr Thr Pro Ser Lys Ser Thr Thr Ala Lys
Leu Leu Ser Gly Ala Thr Trp Ser Ile Ser Tyr Gly Asp Gly Ser Ser Ser
Ser Gly Asp Val Tyr Thr Asp Thr Val Ser Val Gly Gly Leu Thr Val Thr
Gly Gln Ala Val Glu Ser Ala Lys Lys Val Ser Ser Ser Phe Thr Glu Asp
Ser Thr Ile Asp Gly Leu Leu Gly Leu Ala Phe Ser Thr Leu Asn Thr Val
Ser Pro Thr Gln Gln Lys Thr Phe Phe Asp Asn Ala Lys Ala Ser Leu Asp
Ser Pro Val Phe Thr Ala Asp Leu Gly Tyr His Ala Pro Gly Thr Tyr Asn
Phe Gly Phe Ile Asp Thr Thr Ala Tyr Thr Gly Ser Ile Thr Tyr Thr Ala
Val Ser Thr Lys Gln Gly Phe Trp Glu Trp Thr Ser Thr Gly Tyr Ala Val
Gly Ser Gly Thr Phe Lys Ser Thr Ser Ile Asp Gly Ile Ala Asp Thr Gly
Thr Thr Leu Leu Tyr Leu Pro Ala Thr Val Val Ser Ala Tyr Trp Ala Gln
Val Ser Gly Ala Lys Ser Ser Ser Ser Val Gly Gly Tyr Val Phe Pro Cys
Ser Ala Thr Leu Pro Ser Phe Thr Phe Gly Val Gly Ser Ala Arg Ile Val
Ile Pro Gly Asp Tyr Ile Asp Phe Gly Pro Ile Ser Thr Gly Ser Ser Ser
```

-continued

Cys Phe Gly Gly Ile Gln Ser Ser Ala Gly Ile Gly Ile Asn Ile Phe Gly

Asp Val Ala Leu Lys Ala Ala Phe Val Val Phe Asn Gly Ala Thr Thr Pro

Thr Leu Gly Phe Ala Ser Lys.

A cassette for the expression of an endothiapepsin precursor denotes here a DNA sequence comprising the sequence coding for this precursor, flanked by signals enabling this coding sequence in *Cryphonectria parasitica* to be transcribed and translated.

Endothiapepsin precursor is understood to mean a protein capable of being secreted and of generating endothiapepsin in the culture medium after one or more maturation steps.

The natural precursor of endothiapepsin, referred to as preproendothiapepsin and having the following sequence (P4)(SEQ ID NO:2), will preferably be used:

Met Ser Ser Pro Leu Lys Asn Ala Leu Val Thr Ala Met Leu Ala Gly Gly

Ala Leu Ser Ser Pro Thr Lys Gln His Val Gly Ile Pro Val Asn Ala Ser

Pro Glu Val Gly Pro Gly Lys Tyr Ser Phe Lys Gln Val Arg Asn Pro Asn

Tyr Lys Phe Asn Gly Pro Leu Ser Val Lys Lys Thr Tyr Leu Lys Tyr Gly

Val Pro Ile Pro Ala Trp Leu Glu Asp Ala Val Gln Asn Ser Thr Ser Gly

Leu Ala Glu Arg Ser Thr Gly Ser Ala Thr Thr Thr Pro Ile Asp Ser Leu

Asp Asp Ala Tyr Ile Thr Pro Val Gln Ile Gly Thr Pro Ala Gln Thr Leu

Asn Leu Asp Phe Asp Thr Gly Ser Ser Asp Leu Trp Val Phe Ser Ser Glu

Thr Thr Ala Ser Glu Val Asp Gly Gln Thr Ile Tyr Thr Pro Ser Lys Ser

Thr Thr Ala Lys Leu Leu Ser Gly Ala Thr Trp Ser Ile Ser Tyr Gly Asp

Gly Ser Ser Ser Ser Gly Asp Val Tyr Thr Asp Thr Val Ser Val Gly Gly

Leu Thr Val Thr Gly Gln Ala Val Glu Ser Ala Lys Lys Val Ser Ser Ser

Phe Thr Glu Asp Ser Thr Ile Asp Gly Leu Leu Gly Leu Ala Phe Ser Thr

Leu Asn Thr Val Ser Pro Thr Gln Gln Lys Thr Phe Phe Asp Asn Ala Lys

Ala Ser Leu Asp Ser Pro Val Phe Thr Ala Asp Leu Gly Tyr His Ala Pro

Gly Thr Tyr Asn Phe Gly Phe Ile Asp Thr Thr Ala Tyr Thr Gly Ser Ile

Thr Tyr Thr Ala Val Ser Thr Lys Gln Gly Phe Trp Glu Trp Thr Ser Thr

Gly Tyr Ala Val Gly Ser Gly Thr Phe Lys Ser Thr Ser Ile Asp Gly Ile

Ala Asp Thr Gly Thr Thr Leu Leu Tyr Leu Pro Ala Thr Val Val Ser Ala

Tyr Trp Ala Gln Val Ser Gly Ala Lys Ser Ser Ser Ser Val Gly Gly Tyr

Val Phe Pro Cys Ser Ala Thr Leu Pro Ser Phe Thr Phe Gly Val Gly Ser

Ala Arg Ile Val Ile Pro Gly Asp Tyr Ile Asp Phe Gly Pro Ile Ser Thr

Gly Ser Ser Ser Cys Phe Gly Gly Ile Gln Ser Ser Ala Gly Ile Gly Ile

Asn Ile Phe Gly Asp Val Ala Leu Lys Ala Ala Phe Val Val Phe Asn Gly

Ala Thr Thr Pro Thr Leu Gly Phe Ala Ser Lys.

Sielecki, 1986, Nature, 319, 33–38) and *S. cerevisiae* protease A (Woolford et al., 1986 Mol. Cel. Biol. 6, 2500–2510), it may be assumed that the natural precursor of endothiapepsin generates an inactive secreted form, referred to as proendothiapepsin, which self-activates to mature endothiapepsin.

As a result of the degeneracy of the genetic code, there is a large number of DNA sequences coding for a protein whose sequence P4 (SEQ ID NO:2) corresponds to the formula given above. Among these, a suitable sequence is that which comprises the following sequence (N4a)(SEQ ID NO:3):

By anology with what is known for other aspartic proteases such as calf chymosin (Foltmann, 1970, Methods in Enzymol., 19, 421–435), swine pepsinogen (James and

```
ATGTCTT  CCCCTCTCAA  GAACGCCTTG  GTGACCGCCA  TGTTGGCTGG
TGGTGCTCTC  AGCTCGCCTA  CAAAGCAACA  CGTTGGAATT  CCCGTCAACG
CCTCTCCTGA  AGTTGGCCCC  GGAAAGTACT  CGTTCAAGCA  AGTCCGGAAC
CCCAACTACA  AGTTCAACGG  GCCTCTGTCG  GTCAAGAAGA  CGTACCTCAA
GTACGGCGTG  CCGATCCCAG  CCTGGCTGGA  GGATGCTGTC  CAGAACTCTA
CCTCGGGCCT  GGCTGAGCGC  TCGACCGGTT  CTGCGACCAC  AACTCCCATC
GACAGCCTCG  ATGATGCTTA  CATCACTCCG  GTTCAGATCG  GCACCCCTGC
GCAGACTCTG  AACCTGGACT  TTGACACTGG  ATCTTCGGAT  CTGTGGGTCT
TCAGCAGCGA  GACTACAGCC  AGCGAGGTCG  ATGGGCAGAC  CATCTACACC
CCCAGCAAGA  GCACCACCGC  CAAGCTGCTG  TCGGCGCTAC  CTGGTCCATC
TCCTACGGAG  ACGGTAGCTC  TTCCAGCGGC  GATGTCTACA  CTGACACCGT
CTCGGTTGGA  GGCCTTACCG  TGACGGGCCA  GGCTGTCGAG  TCGGCCAAGA
AGGTTTCTTC  CAGCTTCACC  GAGGACTCGA  CCATTGACGG  TCTCCTGGGC
CTGGCCTTCA  GCACCCTGAA  CACTGTGTCG  CCTACCCAGC  AAAAGACTTT
CTTCGACAAT  GCGAAGGCGT  CCTTGGACTC  GCCTGTGTTC  ACGGCTGATC
TTGGCTACCA  TGCCCCTGGT  ACCTACAACT  TCGGCTTCAT  CGATACCACT
GCCTACACGG  GCTCCATCAC  CTACACCGCT  GTCTCGACCA  AGCAAGGGTT
CTGGGAGTGG  ACTTCGACCG  GCTACGCCGT  CGGCTCCGGC  ACCTTCAAGT
CGACTTCCAT  CGACGGCATC  GCTGACACTG  GCACGACCCT  CCTGTACCTC
CCTGCCACCG  TCGTGTCGGC  CTACTGGGCC  CAGGTCTCGG  GCGCCAAGTC
CAGCTCTTCC  GTCGGCGGCT  ACGTCTTCCC  CTGCAGCGCG  ACCCTGCCTT
CCTTCACCTT  CGGCGTTGGC  TCAGCTCGCA  TTGTGATTCC  TGGCGACTAC
ATTGATTTCG  GCCCCATCTC  CACTGGAAGC  TCGTCTTGCT  TTGGCGGCAT
CCAGTCCAGC  GCTGGTATCG  GCATCAACAT  CTTCGGTGAT  GTCGCTCTGA
AGGCTTTGTC  GTCTTCAACG  GGGCTACAAC  TCCCACTCTT  GGCTTTGCTT
CCAAG
```

It is preferable for the sequence coding for the endothiapepsin precursor to be interrupted by at least one intron. It is known, in effect, that the presence of introns in the coding portion of a gene can in some cases increase the expression of the latter (see, for example, the work of J. Callis et al., 1987, Genes and Development, 1, 1183–1200).

An advantageous sequence coding for preproendothiapepsin is hence that which comprises the sequence (N4a) (SEQ ID NO:3) interrupted by at least one intron. An especially valued sequence of this type is that which comprises the following sequence (N4b)(SEQ ID NO:4):

```
                                   AT  GTCTTCCCCT  CTCAAGAACG
CCTTGGTGAC  CGCCATGTTG  GCTGGTGGTG  CTCTCAGCTC  GCCTACAAAG
CAACACGTTG  GAATTCCCGT  CAACGCCTCT  CCTGAAGTTG  GCCCCGGAAA
GTACTCGTTC  AAGCAAGGTG  AGTAGAGCTG  CTTCTGTGTG  TTGCAACAGA
AGACCAACGC  AAAAAGAAGA  GGTCAAGGCA  AGACGGATAT  TTTACTGACA
ATTATACTTT  TGAAGTCCGG  AACCCCAACT  ACAAGTTCAA  CGGGCCTCTG
TCGGTCAAGA  AGACGTACCT  CAAGTACGGC  GTGCCGATCC  CAGCCTGGCT
GGAGGATGCT  GTCCAGAACT  CTACCTCGGG  CCTGGCTGAG  CGCTCGACCG
GTTCTGCGAC  CACAACTCCC  ATCGACAGCC  TCGATGATGC  TTACATCACT
```

-continued
```
CCGGTTCAGA TCGGCACCCC TGCGCAGACT CTGAACCTGG ACTTTGACAC

TGGATCTTCG GATCTGTGGG TCTTCAGCAG CGAGACTACA GCCAGCGAGG

TTGGTCAACC CTCGCCCGCA TTTTATTGCA TACATTTTTA GTTTTTTTGG

TAATCAGAAT ACTAACATTG GGAATTTCCC AACTGTAGGT CGATGGGCAG

ACCATCTACA CCCCCAGCAA GAGCACCACC GCCAAGCTGC TGTCGGGCGC

TACCTGGTCC ATCTCCTACG GAGACGGTAG CTCTTCCAGC GGCGATGTCT

ACACTGACAC CGTCTCGGTT GGAGGCCTTA CCGTGACGGG CCAGGCTGTC

GAGTCGGCCA AGAAGGTTTC TTCCAGCTTC ACCGAGGACT CGACCATTGA

CGGTCTCCTG GGCCTGGCCT TCAGCACCCT GAACACTGTG TCGCCTACCC

AGCAAAAGAC TTTCTTCGAC AATGCGAAGG CGTCCTTGGA CTCGCCTGTG

TTCACGGCTG ATCTTGGCTA CCATGCCCGT GAGTGACCCC TCTTGATACA

TATACTTTTT GATGAATCTT GTTGGAGAAG CATTCCCCAC TAATATGGAA

ATTGTTTGTA TCTACAGCTG GTACCTACAA CTTCGGCTTC ATCGATACCA

CTGCCTACAC GGGCTCCATC ACCTACACCG CTGTCTCGAC CAAGCAAGGG

TTCTGGGAGT GGACTTCGAC CGGCTACGCC GTCGGCTCCG GCACCTTCAA

GTCGACTTCC ATCGACGGCA TCGCTGACAC TGGCACGACC CTCCTGTACC

TCCCTGCCAC CGTCGTGTCG GCCTACTGGG CCCAGGTCTC GGGCGCCAAG

TCCAGCTCTT CCGTCGGCGG CTACGTCTTC CCCTGCAGCG CGACCCTGCC

TTCCTTCACC TTCGGCGTTG GCTCAGCTCG CATTGTGATT CCTGGCGACT

ACATTGATTT CGGCCCCATC TCCACTGGAA GCTCGTCTTG CTTTGGCGGC

ATCCAGTCCA GCGCTGGTAT CGGCATCAAC ATCTTCGGTG ATGTCGCTCT

GAAGGCCGCC TTTGTCGTCT TCAACGGGGC TACAACTCCC ACTCTTGGCT

TTGCTTCCAA G
```

A functional promoter means here a constitutive or regulable promoter capable of producing in *Cryphonectria parasitica* transcription of the sequence coding for the endothiapepsin precursor. This promoter contains a TATA element located in a zone rich in AT, a transcription initiation region downstream of this element and, upstream of the latter, sequences referred to as upstream activating sequences UAS or upstream repressing sequences URS which regulate the strength of the promoter through the effect of regulatory proteins.

To determine the functionality of a DNA sequence as a promoter, the method described in Section 11 will conveniently be used. This consists in transforming a *Cryphonectria parasitica* strain rendered deficient in the production of endothiapepsin by a mutation of the structural gene for this protein, with the expression cassette carrying the test sequence and a selection marker, and then in identifying among the transformants those which are producers of endothiapepsin using the selection test on agar medium containing casein described in Section 7.

A valued promoter is the promoter of the gene coding for preproendothiapepsin or a functional portion of this promoter. The portion in question comprises, for example, a portion carrying the TATA box of the following sequence (N5)(SEQ ID NO:5):

```
AAGCTTATCC GCCGCCGGCG GGGGAATTCT ATTGAACTTG TTCGAATCAT
TGGTCCGTGG TCTTTTCGTC CATGCGGGCT CCGCTGGCGG ATGAATGACC
TTCTGGCTTC TAGCCTGGCG AAGCGATGTT ACTCTGTTGT CTATACTATA
CGATATGGTC AAGAGAGCAC ATGTGCCGCC AGATGAAGAC ATGTATATAA
AAGGAGTGGC CTCGACGGTT GCTCAACCAT CTTCTGTCTG TCCCAACGCC
ATCGACTCTT CAACTTCTCC TTCGTGTTCC ACCACCATCA CCTTGCTCCA
GACTTAGGAC TTTCAGCAAC CTTCAAAG
``` and, upstream of the sequence (N5)(SEQ ID NO:5), a segment X of the fragment C bounded by the 5' end of the fragment A and the 5' end of the fragment C, chosen so that the segment X contains an activator region. The fragment C is a portion of the genomic DNA of *Cryphonectria parasitica* contained in the *E. coli* strain deposited with the CNCM on 31.08.1990 under No. I-998. Its restriction map, as well as that of the fragment A contained in the fragment C, are shown in FIG. 4. The nucleotide sequence of the fragment A, which comprises the genomic DNA of Cryphonectria parasitica coding for preproendothiapepsin, is shown in FIG. 2, and is identified in the Sequence Listing as SEQ ID NO:32.

A more precise localisation of this activator region may be effected by obtaining a series of segments of the fragment C (prepared, for example, by digestion using endonucleases or exonucleases) comprising the fragment A flanked on the 5' side by segments of different sizes of the portion of the fragment C bounded by the 5' end of the fragment A and the 5' end of the fragment C, and determining the functionality of the promoter obtained using the method mentioned above.

An example of a segment X of the fragment C containing an activator region is the fragment of sequence below (SEQ ID NO:6):

```
GCATGCTTGG CTCTTTAACG TCCTGCCCAT TCAGGGCCTT CAGCCGGCAC
TGGTCCTTCA TCAAGGGGGA CCTCATGACC ATGAACTAAT CTGTGATATC
TGATATATTC TAGAAGGCTT GGCTCCTCAA AGTTTCCAGC TAATGAATCA
GCGGCCCGCC GCCCTTAAAC CGCATCAGGC AAGTCGTTTG GTGTTGCCAG
GCGATGGCGA CAGGAGAGTG GTGTTGATGG GACAAGGGGA GGGAGGCTTA
GCCGACTTCA TCCATAGCAC CCACCTGCTT GGCGCCGATA AGTCTGACGA
TCCGCTTGAG CTGCAAAACG GCTCCTTGAC CTTTGTTTGG TCGACCGAGG
GAAATAGTCT CTTTTTGCGT GATCGTGCGC GCTTCGTATA GCAATAGCAG
CCAGCACCAG CAGGACGGGC CGTTGTCACG GTCACATCGT TCGCAACATG
CCGAGCGTAG GGATGAACGA ATGACTCGAG CCTTGCCTGA CAGTCTGGCA
ATCAATCTAT GGTCACGCAC GATCACAAGC CAATCGCTGT GACTGCGTTA
CTAGCCCAAT AATCCCTTGT TCGATCAGAG TGTTCTACAG ACTTCAAGTG
AGGTTCAC
```

Examples of functional portions of the promoter of the gene coding for preproendothiapepsin are the BglII-ScaI and BamHI-ScaI segments of the fragment C (see FIG. 4).

It can also be advantageous to use a promoter originating from another gene known to be expressed in *Cryphonectria parasitica* or in another filamentous fungus of the Ascomycetes group, for example the promoter of the gene coding for glyceraldehyde-3-phosphate dehydrogenase of *Cryphonectria parasitica* described by Choi et al., 1990, Nucleic Acids Research, 18, 18, Oxford University Press, or that of the gene coding for glyceraldehyde-3-phosphate dehydrogenase of *Aspergillus nidulans* described by Mullaney et al., 1985, Mol. Gen. Genet., 199, 37–45.

The expression cassette is introduced into *Cryphonectria parasitica* preferably by cotransformation with a vector carrying the selection gene. The expression cassette is itself carried by a vector, or preferably in the form of a linear fragment. The expression cassette is preferably maintained in the integrated state in the chromosome. The vector carrying the selection gene is maintained either by integration in the chromosome, or in extrachromosomal linear form using sequences of the telomeric sequence type. After sporulation, transformants which have lost the selection marker are preferably selected.

The invention hence also relates to a *Cryphonectria parasitica* strain productive of endothiapepsin, characterised in that it is transformed with the cassette defined above and overproduces endothiapepsin compared with the untransformed strain, that is to say secretes more endothiapepsin than the latter.

For use of this strain in the agri-foodstuffs industry, it is advantageous for this strain to be devoid of a dominant selection marker such as, for example, an antibiotic resistance gene.

Preferably, the host strain is the strain SEBR103 obtained as a result of a conventional mutation/selection process and deposited with the CNCM at the Institut Pasteur, 28, rue du Dr. Roux, 75724 Paris C e dex 15, France, on 31.08.1990 under No. I-997. It is then perceived that the transformed strain overproduces endothiapepsin compared with the strain SEBR103 with an overproduction ratio equal to at least two.

The invention also relates to a process for preparing endothiapepsin, characterised in that it comprises a step of culturing of the strain defined above, followed by a step of isolation and purification of this protein. This process will advantageously replace the current processes for producing endothiapepsin.

The invention also relates to a process for obtaining a *Cryphonectria parasitica* strain over-productive of endothiapepsin, transformed with the cassette defined above and devoid of a dominant selection marker, characterised in that it comprises at least one cycle entailing a step of cotransformation with a cassette according to one of Claims 1 to 12, and a dominant selection marker, followed by a step of purification by sporulation enabling the dominant selection marker to be removed. Preferably, this process comprises at least two cycles of this type.

A better understanding of the invention will be gained from the description below, divided into sections, which comprises experimental results and a discussion of the latter. Some of these sections relate to experiments performed with the aim of carrying out the invention, others to examples of embodiment of the invention, naturally given purely by way of illustration.

A large part of the collective techniques below, which are well known to those skilled in the art, is described in detail in the work by Sambrook and Maniatis: "Molecular cloning: a Laboratory manual" published in 1989 by Cold Spring Harbor Press publications, New York (2nd edition):

A better understanding of the description below will be gained by reference to FIGS. 1 to 12.

BRIEF DESCRIPTION OF THE DRAWINGS

FIG. 1 shows the amino acid sequence of endothiapepsin (SEQ ID NO:1).

FIG. 2 shows the nucleotide sequence of the fragment A (SEQ ID NO:32), the BstEII site used in Section 10 being indicated by vertical broken lines, as well as the amino acid sequence (SEQ ID NO:33) translated.

FIG. 3 shows the amino acid sequence (SEQ ID NO:33) of preproendothiapepsin.

FIG. 5 shows the genomic DNA sequence coding for preproendothiapepsin, interrupted by three introns which are underlined (SEQ ID NO:4).

— = DNA segment emanating from plasmid pBR322

- - - - - - -

◯ = localisation of the origin of replication (ORI)

— = DNA segment containing the sequence coding for a natural precursor of hGH

▓ = DNA segment of phage fd containing a transcription terminator

/////// = DNA segment containing a tryptophan/lactose hybrid promoter/operator UV5

■ = DNA segment coding for β-lactamase (Ap^R: ampicillin resistance).

Figure 7:
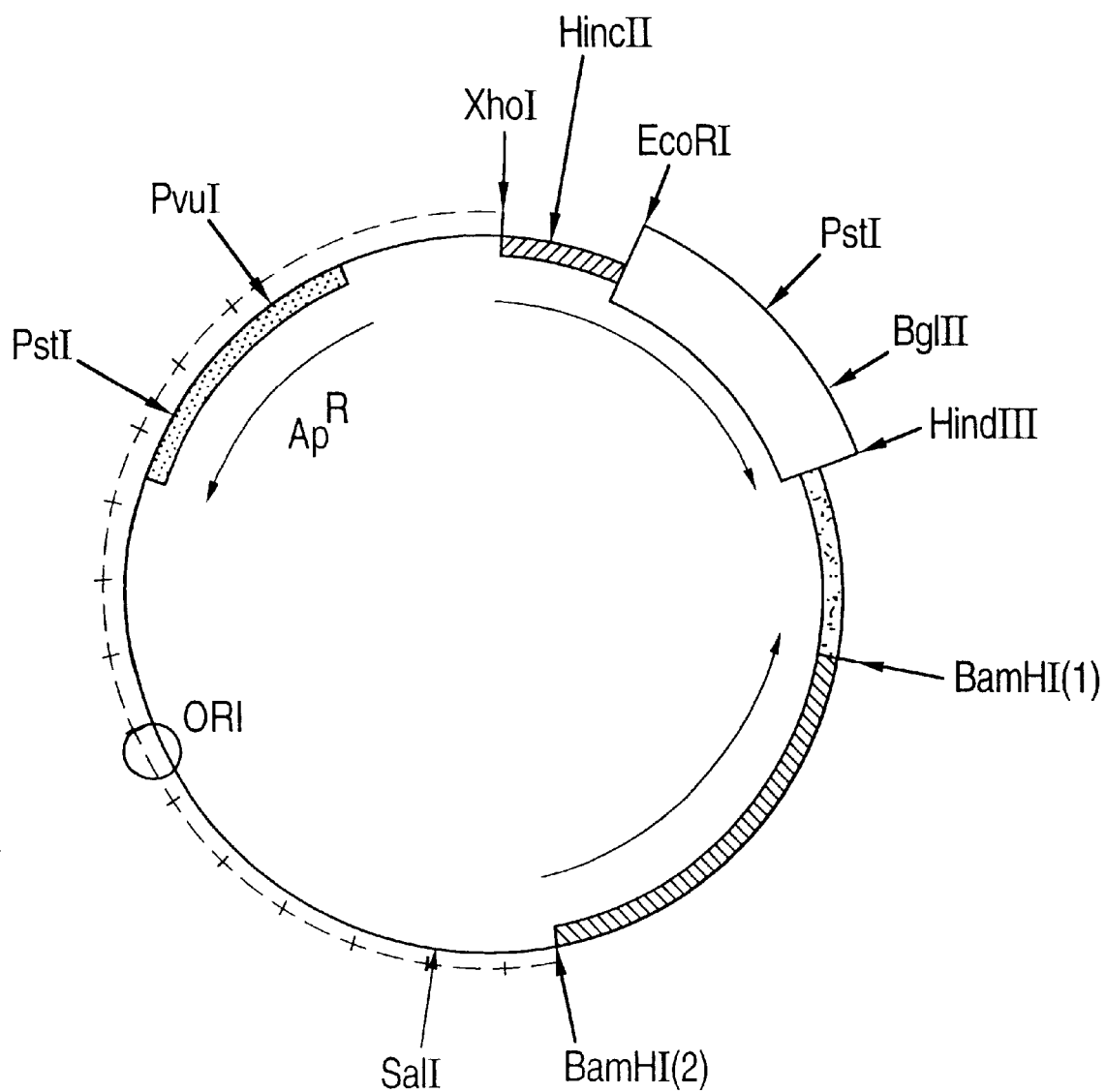

FIG. 7 shows the restriction map of a plasmid p160 of which the PvuI-XhoI-BamHI(1) and PvuI-ORI-BamHI(2) fragments originate, respectively, from plasmids p163,1 and pBR327, and of which the small BamHI(2)-BamHI(1) fragment is the fragment 3 described below.

Figure 8:
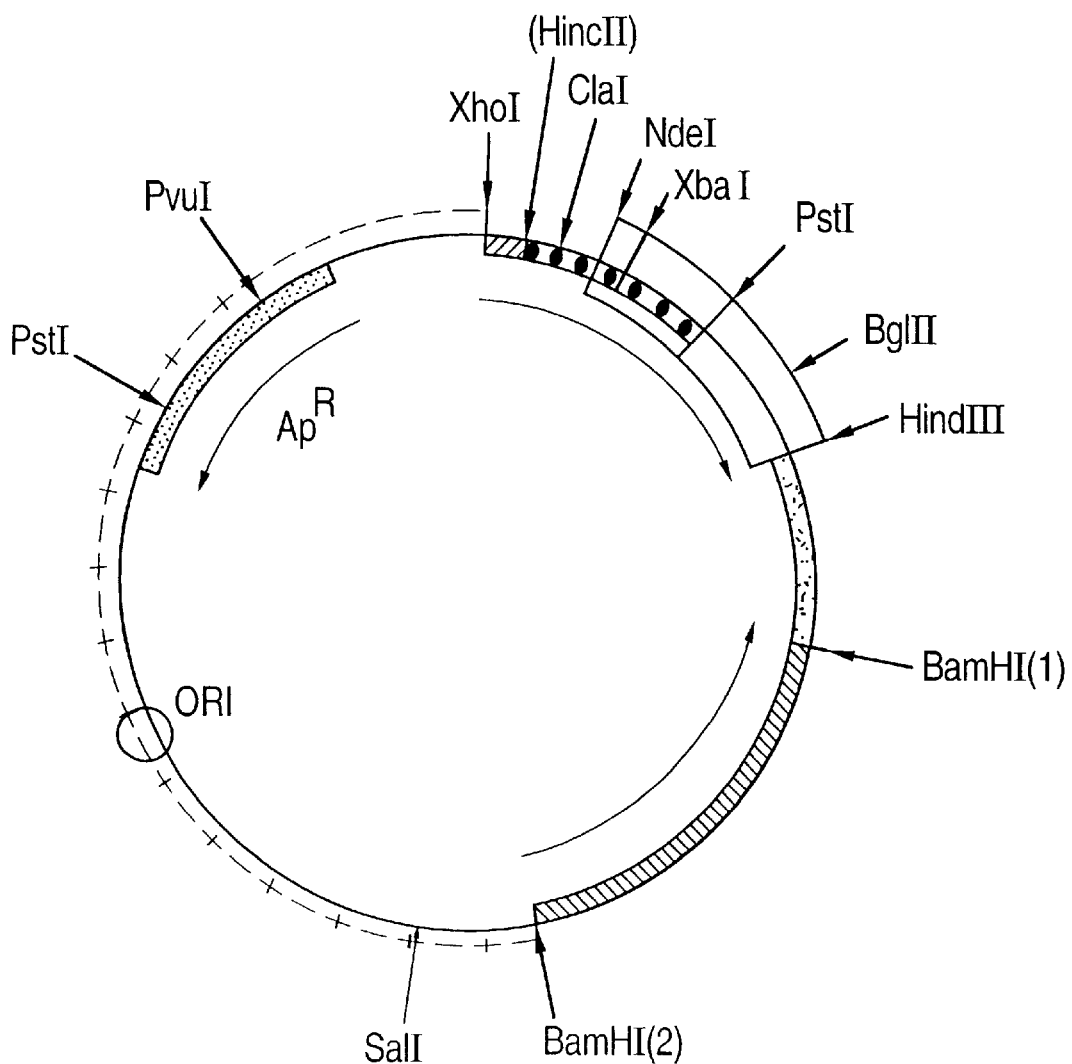

FIG. 8 shows the restriction map of plasmid p373,2. The different restriction segments are arbitrarily labelled according to the following legend:

+—+—+ = PvuI-BamHI sequence emanating from plasmid pBR327

——— = PvuI-XhoI sequence emanating from plasmid p163,1

- - - - - -

/////// = XhoI-HincII sequence emanating from plasmid p163,1

(HincII) ClaI NdeI PstI
●●●●●●● Fragment 4 described below

XXXXX = Fragment 3 described below

▓ = DNA segment of phage fd containing a transcription terminator

Figure 9:
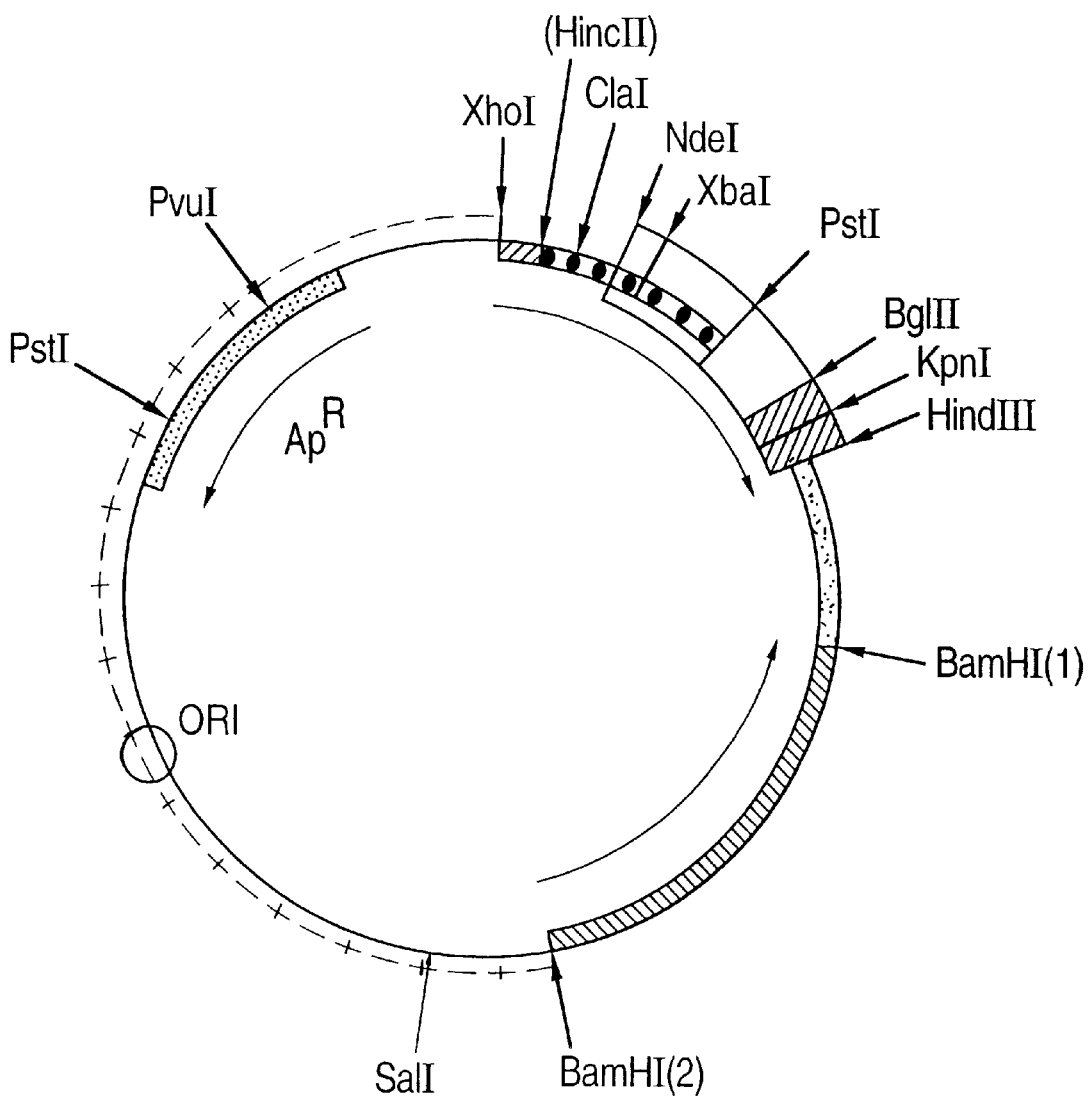

FIG. 9 shows a restriction map of plasmid p462, the synthetic BglII-HindIII fragment defined below being indicated by:

▨

Figure 10:
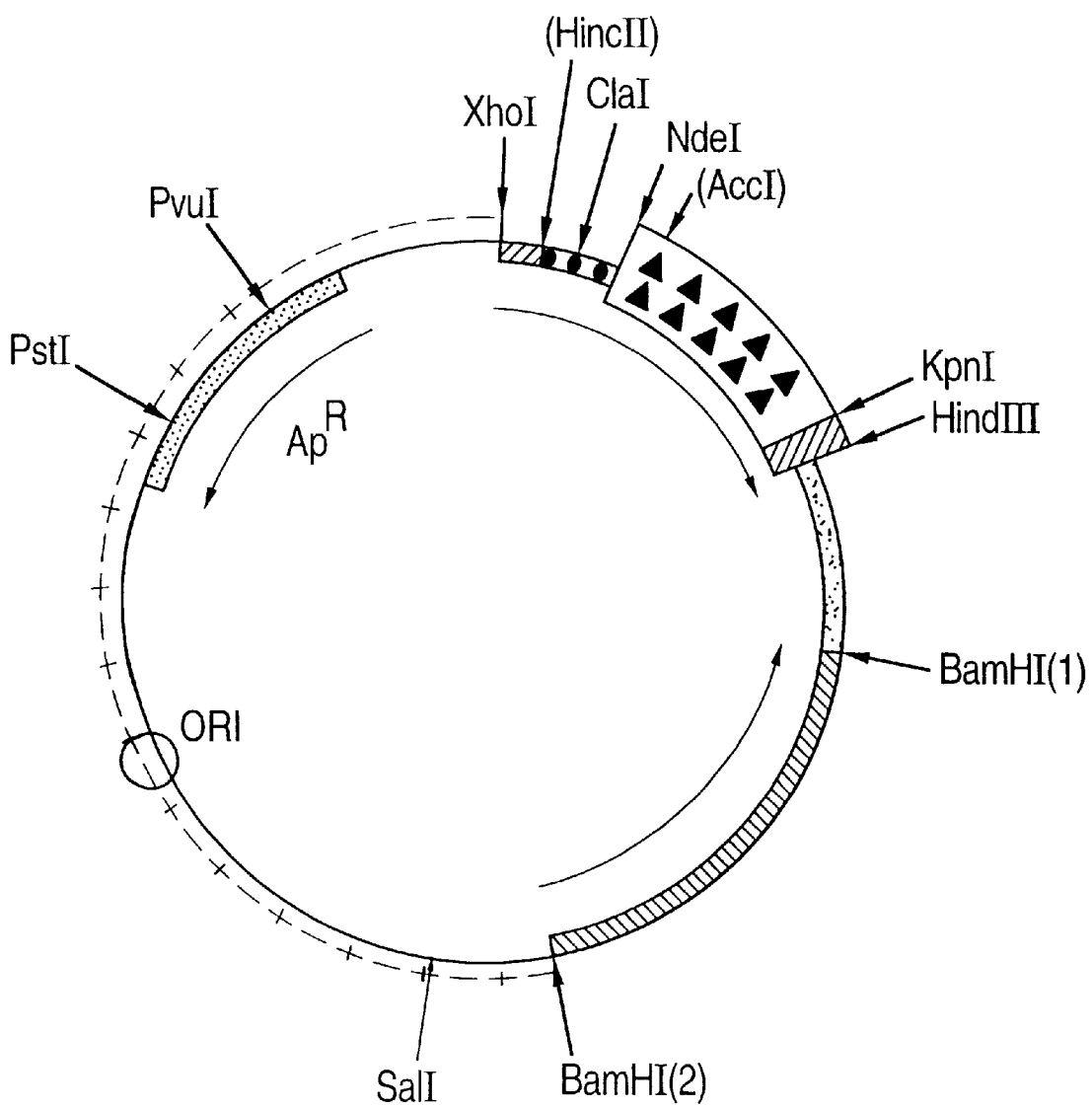

FIG. 10 shows a restriction map of plasmid p466, the NdeI-KpnI fragment comprising the gene coding for urate oxidase being indicated by:

▲▲▲▲▲▲

FIG. 11 shows the complementary DNA sequence coding for preproendothiapepsin (SEQ ID NO:3).

FIG. 12 shows the sequence of the SphI-HindIII segment of the fragment F (SEQ ID NO:5).

Section 1

Isolation of the fragment A, an approximately 2.1-kb fragment of genomic DNA containing the coding sequence of the endothiapepsin precursor.

1) Preparation of the genomic DNA

The strain referred to as SEBR 103 was identified by the Centraal Bureau Voor Schimellcultures as belonging to the species *Cryphonectria parasitica* and deposited with the Collection Nationale de Culture de Microorganismes (National Collection of Microorganism Cultures) C.N.C.M. under No. I-997.

From conidiospores of *Cryphonectria parasitica* strain SEBR 103 harvested at the surface of a Petri dish containing an agar medium, referred to as medium G and whose composition is specified in Table 3 below, previously inoculated with a mycelial implant or with a suspension of conidiospores of this same strain and then incubated for 4 weeks at room temperature and in the light, a Petri dish containing 25 ml of an agar medium, referred to as medium A and whose composition is given in Table 1 below, is inoculated by plating out one drop of conidiospore suspension. After 3 days' incubation at 30° C., the mycelium obtained is used to inoculate a 1—1 flask containing 100 ml of a liquid medium, referred to as medium B and whose composition is specified in Table 2 below. After 24 h of incubation at 28° C. with stirring at 220 rpm, 25 ml of the culture broth are used for inoculating 250 ml of fresh medium B contained in a 1—1 flask. The following day, after incubation under the conditions already defined, the whole of the culture broth (250 ml) is centrifuged at 5,000 g for 5 min. The pellet is resuspended in 0.15M sodium acetate solution containing 1 mM EDTA. The mycelium is recovered by filtration on Whatman 3MM paper, frozen in liquid nitrogen and reduced to a powder using a mortar and pestle.

10 g of mycelium powder are taken up in 40 ml of 0.15M sodium acetate solution containing 4% of lauroylsarcosine sodium salt, pH 5. After 30 min of gentle stirring at room temperature, sodium chloride is added to a final concentration of 0.1M. After 30 min of gentle stirring at room temperature, the proteins are extracted with a phenol solution (49% v/v) containing isoamyl alcohol (2% v/v) and chloroform (49% v/v). After 3 extractions with this mixture, extraction is performed with a chloroform solution containing isoamyl alcohol (96% of chloroform/4% of isoamyl alcohol). After 2 extractions of this type, the aqueous phase is subjected to the addition of 2 volumes of ethanol. The 2 solutions are mixed gently by inversion, which causes the appearance of a filament of precipitated DNA. This filament is removed using a Pasteur pipette and deposited in an Eppendorf tube. This tube is centrifuged for 5 min at 100 g. The pellet is washed in 70% ethanol solution and then dried under vacuum. The pellet is taken up in 1 ml of buffer, referred to as TE buffer, of composition [10 mM Tris-HCl, pH 8; 1 mM EDTA].

TABLE 1

| Composition of medium A | | |
|---|---|---|
| Glucose, anhydrous | 50 | g/l |
| Soybean flour (Soyoptim of Société Industrielle des Oléagineux) | 20 | g/l |
| Calcium nitrate | 9 | g/l |
| Agar (Difco Bacto-agar) | 15 | g/l |
| Saline solution 1 (composition specified below) | 0.5 | g/l |
| Check or adjust the pH to 6.0 using 1N HCl or 1N NaOH | | |
| Composition of saline solution 1 | | |
| $H_3BO_3$ | 30 | ml |
| $MnCl_2.4H_2O$ | 79 | ml |

TABLE 1-continued

| | | |
|---|---|---|
| $ZnCl_2$ | 200 | ml |
| $Na_2MoO_4.2H_2O$ | 20 | ml |
| $FeCl_3$, anhydrous | 50 | ml |
| $CuSO_4.5H_2O$ | 200 | ml |
| Distilled water qs | 500 | ml |
| (This suspension is stored for not more than one month at +4° C.) | | |

TABLE 2

| Composition of medium B | | |
|---|---|---|
| Glucose | 10 | g/l |
| Thiamine | 2 | mg/l |
| Saline solution 2 (composition given below) | 62.5 | ml/l |
| Yeast extract (Difco) | 2.5 | g/l |
| Malt extract (Difco) | 7.5 | g/l |
| Check or adjust the pH to 6.0 using 1N HCl or 1N NaOH | | |
| Sterilise for 30 min at 110° C. | | |
| Composition of saline solution 2 | | |
| $NH_4NO_3$ | 24 | g/l |
| $KH_2PO_4$ | 16 | g/l |
| $NaH_2SO_4$ | 4 | g/l |
| KCl | 8 | g/l |
| $MgSO_4.7H_2O$ | 2 | g/l |
| $CaCl_2$ | 1 | g/l |
| Saline solution 1 (composition specified in Table 1) | 8 | ml/l |

TABLE 3

| Composition of medium G | | |
|---|---|---|
| Part A | | |
| Malt extract | 20 | g |
| Yeast extract | 2 | g |
| Agar | 16 | g |
| Water | 1 | l |
| Adjust to pH 5.5 | | |
| Autoclave for 20 min at 120° C. | | |
| Part B | | |
| Aspartic acid | 1,000 | mg |
| Biotin | 10 | mg |
| Water | 1 | l |
| Dilute part B to 1/10, distribute it while filtering at a concentration of 0.2M in 1 ml fractions and store at −20° C. | | |

At the time of use, add 1 ml of diluted part B to 1 l of part A supercooled to 45° C., then distribute the mixture in Petri dishes.

2) Preparation of probe 1 and probe 2

These probes are pools of synthetic oligonucleotides, comprising the collective coding sequences for two peptides chosen from within the amino acid sequence of mature endothiapepsin exported into the culture medium of *C. parasitica*, described by V. BARKHOLT, 1987, Eur. J. Biochem., 167, 327–338, shown in FIG. 1. The peptides chosen from within this sequence, referred to as peptide 1 and peptide 2 and corresponding, respectively, to probe 1 and probe 2, are as follows:

Peptide 1(SEQ ID NO:7): Val-Asp-Gly-Gln-Thr

Peptide 2(SEQ ID NO:8): Gly-Phe-Trp-Glu-Trp-Thr

To these peptides there correspond, respectively, 256 ($4^3 \times 2^2$) and 64 ($4^2 \times 2^2$) oligonucleotides coding for the latter, represented by the formulae below.

```
         A    A      A
         C    C   C  G   C
         GT GA GG CA AC         probe 1(SEQ ID NO:9)
          G  T  G  A G
          T     T    T
          A              A
          C  C      A    C
         GG TT TGGGA TGGAC      probe 2(SEQ ID NO:10)
          G  T    G    G
          T            T
```

3) Labelling of probe 1 and probe 2

The probes are labelled with terminal deoxynucleotidyl transferase (TdT) (marketed by Stratagene, ref.: 600 132).

The reaction is performed on 100 ng of a mixture of oligonucleotides dissolved in "Cobalt" reaction buffer (supplied at 10-fold concentration by IBI Inc.): 1.4M potassium cacodylate pH 7.2, 300 mM dithiothreitol, 1 µl of terminal deoxynucleotidyl transferase enzyme (Stratagene) and 50 µCi of $^{32}$P-labelled deoxycytidine triphosphate dCTP.

The reaction is carried out at 37° C. for 10 minutes and is then stopped by adding 1 µl of 0.5M EDTA.

The products are extracted with phenol and the mixture is dialysed on a Biogel P 10 polyacrylamide column (Biorad: 150-1050).

Radiolabelled probe 1 and radiolabelled probe 2 are thereby obtained.

4) Hydrolysis of *Cryphonectria parasitica* genomic DNA

The genomic DNA obtained at the end of 1) was subjected separately to a digestion with each of the following restriction enzymes: EcoRI, HindIII and BamHI. In each case, 10 µg of the digestion product were spotted on 0.8% agarose gel and subjected to electrophoresis in the presence of a series of radiolabelled size markers (Amersham ref. SJ5000). The DNA was then transferred onto a nitrocellulose filter (Biorad, ref. 162-0117) according to the technique well known to those skilled in the art under the name of Southern blotting, described in Maniatis, op. cit., this operation being repeated so as to obtain two nitrocellulose filters intended for hybridisation, one with probe 1, the other with probe 2.

5) Hybridisation

Each nitrocellulose filter treated according to the usual techniques (Maniatis et al., op. cit.) was first washed in a prehybridisation solution containing 6×SSC, 10×Denhardt's and 100 µg/ml of sonicated and denatured salmon sperm DNA (Sigma D9156) for a few hours at 42° C., and then incubated in the same solution and under the same conditions as those stated above in the presence of one of the labelled probes 1 and 2. The hybridisation is left to proceed overnight. The 6×SSC solution is obtained by dilution of a 20×SSC solution. The preparation of the 20×SSC buffer is described in Maniatis, op. cit. In brief, this buffer contains 175.3 g/l of NaCl and 88.2 g/l of sodium citrate, and is adjusted to pH 7 with a few drops of 1N NaOH. The 10×Denhardt's solution contains 1 g of Ficoll, 1 g of polyvinylpyrrolidone and 1 g of bovine serum albumin per 500 ml final volume.

After the hybridisation, each of the filters is washed individually in a solution containing 0.5 SSC at 42° C. The filters are then exposed to a photographic film (Kodak XAR5) overnight. Analysis of the developed film shows, in the case of the hydrolysate obtained with the enzyme HindIII, that a band whose molecular weight corresponds approximately to a fragment of size slightly greater than 2.1 kb responds positively with both radio-labelled probes.

6) Cloning of an approximately 2.1-kb HindIII-HindIII DNA- fragment which hybridises with the radio-labelled probes 1 and 2 a) Formation of a library of genomic DNA.

100 µg of *Cryphonectria parasitica* DNA are hydrolysed with the enzyme HindIII and the fragments are separated by electrophoresis on 0.8% agarose gel. The region which corresponds to the fragments of size slightly greater than 2.1 kb is cut out and the DNA is purified by adsorption on silica milk (Geneclean Tm, Biorad P.O. Box 2284, La Jolla, Calif. 92038-2284). These fragments are ligated using phage T4 DNA ligase (Gibco BRL) in pBR322 which has been hydrolysed with HindIII and dephosphorylated (Biolabs Ref. 321). Competent cells (that is to say cells capable of being transformed) (RRI cells, Gibco BRL, Ref. 520-8261 SA) are transformed, as directed by the supplier, with the ligation solution and plated out on agar medium, referred to as LB agar medium (Maniatis, op. cit.), of composition specified in Table 4 below. The collection of colonies obtained is the library of genomic DNA.

TABLE 4

| Composition of LB agar medium | |
|---|---|
| Bacto tryptone casein hydrolysate (Difco) | 10 g/l |
| Bacto yeast extract (Difco) | 5 g/l |
| NaCl | 10 g/l |
| Adjust the pH to 7.0 using 5N NaOH | |
| Bacto agar (Difco) | 15 g/l |
| Autoclave for 20 min at 120° C. | | b) Selection of clones carrying the HindIII—HindIII fragment which hybridises with the radiolabelled probes 1 and 2, referred to as fragment A.

The colonies obtained after transformation are adsorbed on a nitrocellulose filter (Schleicher and Schull, Ref. 40117) and replicated on two other nitrocellulose filters. A first series of filters is hybridised with radiolabelled probe 1 and a second series of filters is hybridised with radiolabelled probe 2. The prehybridisation, hybridisation and washing conditions are the same as those used previously (see 5 above).

The clones which respond positively with both probes are purified. The plasmid DNA of one of these clones is isolated. The corresponding plasmid is referred to as p472. After checking that it did indeed hybridise with each of the two radiolabelled probes 1 and 2, the 2.1-kb HindIII—HindIII fragment carried on this plasmid was isolated and subcloned into M13mpl9 (Pharmacia). This fragment is referred to as fragment A. It was sequenced by the cyclone technique (IBI "Cyclone I Biosystem").

The nucleotide sequence of the fragment A is shown in FIG. 2, which also indicates the numbering of the nucleotides, chosen arbitrarily so as to assign No. 1 to the nucleotide of the 5' end of the fragment A, as well as the amino acid sequence translated.

7) Description of the sequence of the frament A (see FIG. 2 (SEQ ID NO:32))

The fragment A carries the nucleotide sequence coding for the peptide sequence of mature endothiapepsin exported into the culture medium, described by Barkolt (see FIG. 1), which begins at nucleotide 694 and ends at nucleotide 1861 and is interrupted by two introns located at nucleotides 850–938 and 1279–1367. Upstream of nucleotide 694, the open reading frame continues as far as nucleotide 566, where there is a signal characteristic of the end of an intron: AG. At nucleotides 468–469, there is a signal characteristic of the beginning of an intron: GT. It will be noted that the sequence straddling the beginning of the intron and the end of the exon, namely AAGGTGAGT, corresponds to the 5' consensus sequence of the splicing junction described by Mount S. M., 1982, Nucl. Ac. Res., 10, 459–472. Upstream of nucleotide 468, there is only a single open reading frame (frame not interrupted by a stop codon) containing at least one ATG. This frame contains an ATG at position 365–367 (the nucleotide environment of which is compatible with M. Kozak, 1984, Nucl. Ac. Res. 12, p. 2) and an ATG at position 329–331, this reading frame being interrupted by the stop codon TAG at position 305–307. University of Wisconsin software U.W.G.C.G.: Devereux et al., 1984, Nucl. Ac. Res., 12, 8711–8721-Option: Testing for a signal peptide according to the method of G. von Heijne, 1986, Nucl. Ac. Res., 14, 483–490, predicts in this open reading frame a single sequence coding for a signal peptide, the sequence below (SEQ ID NO:11), referred to as a pre nucleotide sequence (beginning at nucleotide 329):

ATGTCTT CCCCTCTCAA GAACGCCTTG GTGACCGCCA TGTTGGCTGG

TGGTGCTCTC AGC coding for the signal peptide of 20 amino acids of the following sequence, referred to as a pre peptide sequence (SEQ ID NO:12):

Met Ser Ser Pro Leu Lys Asn Ala Leu Val Thr Ala Met Leu Ala Gly Gly Ala Leu Ser

A signal peptide is expected by those skilled in the art, since endothiapepsin is a secreted protein, which requires the presence of a signal peptide.

Between the sequence coding for the above signal peptide and that coding for the mature protein, there is the following nucleotide sequence (SEQ ID NO:13), referred to as a pro nucleotide sequence (beginning at nucleotide 389):

TCGCCTA CAAAGCAACA CGTTGGAATT CCCGTCAACG

CCTCTCCTGA AGTTGGCCCC GGAAAGTACT CGTTCAAGCA AGTCCGGAAC

CCCAACTACA AGTTCAACGG GCCTCTGTCG GTCAAGAAGA CGTACCTCAA

GTACGGCGTG CCGATCCCAG CCTGGCTGGA GGATGCTGTC CAGAACTCTA

CCTCGGGCCT GGCTGAGCGC coding for the following peptide sequence, referred to as a pro peptide sequence (SEQ ID NO:14).

Ser Pro Thr Lys Gln His Val Gly Ile Pro Val Asn Ala Ser Pro Glu Val

Gly Pro Gly Lys Tyr Ser Phe Lys Gln Val Arg Asn Pro Asn Tyr Lys Phe

Asn Gly Pro Leu Ser Val Lys Lys Thr Tyr Leu Lys Tyr Gly Val Pro Ile

Pro Ala Trp Leu Glu Asp Ala Val Gln Asn Ser Thr Ser Gly Leu Ala Glu

Arg

A pro peptide sequence (389–693) is also expected by those skilled in the art, since it has the function of inhibiting endothiapepsin, which is probably toxic to *C. parasitica*, before it is exported to the outer medium, following which this sequence is cleaved off.

There is hence upstream of the sequence coding for mature endothiapepsin the sequence coding for the following prepro peptide sequence (SEQ ID NO:15):

Met Ser Ser Pro Leu Lys Asn Ala Leu Val Thr Ala Met Leu Ala Gly Gly

Ala Leu Ser Ser Pro Thr Lys Gln His Val Gly Ile Pro Val Asn Ala Ser

Pro Glu Val Gly Pro Gly Lys Tyr Ser Phe Lys Gln Val Arg Asn Pro Asn

Tyr Lys Phe Asn Gly Pro Leu Ser Val Lys Lys Thr Tyr Leu Lys Tyr Gly

Val Pro Ile Pro Ala Trp Leu Glu Asp Ala Val Gln Asn Ser Thr Ser Gly

Leu Ala Glu Arg

The nucleotide sequence beginning at nucleotide 329 (FIG. 2) and ending at nucleotide 1861 (FIG. 2), interrupted by three introns, is shown in FIG. 5, the introns being underlined, and hence codes for preproendothiapepsin, the amino acid sequence of which is shown in FIG. 3.

The fragment A comprises in addition a sequence of 328 nucleotides on the 5' side of the initiation ATG (329–331) and a sequence of 275 nucleotides on the 3' side of the TAA stop codon (1862–1864), which contains several potential polyadenylation sites.

The portion of the fragment A on the 5' side of the initiation ATG comprises, on the one hand the untranslated 5' end of the messenger RNA, and on the other hand, upstream of this end, a TATAA sequence (187–191), usually referred to as a TATA box, a consensus sequence present in most promoters of eukaryotes (Ballance D. J., 1986, Yeast, 2, 229–236). In contrast, this portion does not comprise a sequence of the type usually referred to as an upstream activating sequence (UAS) or an upstream regulatory sequence (URS), which are present, for example, in Saccharomyces (Guarente L., 1988, all, 52, 303–305) and in Neurospora (Frederick G. D., 1990,Mol. Gen. Gent., 221, 148–154). There is hence no promoter-activating region upstream of the TATA box in the fragment A. The promoter is hence not functional, as will be shown in Section 6.

Section 2

Isolation of the fragment B, an approximately 32.6-kb fragment of genomic DNA containing the coding sequence of the endothiapepsin precursor.

1) Preparation of *C. parasitica* DNA

Genomic DNA of *C. parasitica* SEBR 103 was prepared according to a protocol similar to that described by B. TURCQ (University Thesis: specialist field Life Sciences, examined orally on Jan. 6, 1989 at the University of BORDEAUX II), summarised below.

Preparation of protoplasts

The mycelium originating from 250 ml of culture broth of *Cryphonectria parasitica* strain SEBR 103, prepared as described in Section 1, is filtered off on gauze and then rinsed with 50 ml of 1M $MgSO_4$. After incubation for 30 min at 37° C., the mycelium is again filtered off on gauze and taken up in 20 ml of 1M $MgSO_4$. 20 ml of 1M $MgSO_4$ containing 10 mg/l of the enzyme mixture CAYLASE C3 (company CAYLA), consisting of chitinases and β-1,3-, β-1,6-, α-1,3- and α-1,4-glucanases as well as other polysaccharidases, are then added and the resulting mixture is incubated for 1 h 30 min at 37° C. with gentle stirring. After filtration of the mixture, the filtrate is centrifuged for 10 min at 3,000 g, and the protoplast pellet obtained is taken up in 20 ml of a buffer, referred to as ST buffer, of composition 0.8M sorbitol, 100 mM Tris-HCl, pH 7.5.

Extraction of genomic DNA from the protoplasts

After a further centrifugation for 10 min at 3,000 g, the protoplast pellet is taken up with 14 ml of lysis buffer (100 mM Tris-HCl pH 9, 35 mM EDTA pH 8; 4% (weight/volume) SDS; proteinase K (Sigma) 600 μg/ml), and the mixture is then incubated for 1 h at 50° C. After a centrifugation for 10 min at 12,000 g, the supernatant volume is adjusted to 15.5 ml with TE buffer of composition 10 mM Tris-HCl pH 8, 1 mM EDTA, and 19.53 g of CsCl are then added. After an ultracentrifugation (16 h at 50,000 rpm in a vertical rotor), the gradient is collected in fractions, which are dialysed against buffer of composition 10 mM Tris-HCl pH 8, 1 mM EDTA, and analysed on 0.8% agarose gel. The fraction possessing a spectrometric ratio between the absorption at 260 nm and the absorption at 280 nm in the region of 1.8 was retained.

Construction of the cosmid library

Approximately 10 μg of genomic DNA of the above fraction were subjected to a partial digestion with the restriction enzyme MboI and ligated using T4 ligase to cosmid pHC79-ura5, an approximately 8-kb cosmid vector constructed by inserting the EcoRI-EcoRI fragment containing the ura5 gene (Begueret et al., 1984, Gene, 32 487–492) at the EcoRI site of the commercially available cosmid pHC79 (marketed by BRL and constructed by HOHN B. et al., 1980, Gene, 11, 291–298), the cosmid pHC79-ura5 having been linearised beforehand with the endonuclease BamHI and dephosphorylated with alkaline phosphatase (Promega ref. CIP—M 204).

The ligation mixture was packaged in phage particles using the Stratagene "Gigapack plus" kit, and was used for transforming the *E. coli* receptor strain LE 392 (Murray et al., 1977,Mol. gen. Genet. 150, p. 53), com-mercially available and distributed by Genofit. After plating out on LB agar medium (see Table 4) supplemented with 100 mg/l of ampicillin, approximately 4,500 ampicillin-resistant clones thereby obtained were subcultured individually on microtitration plates containing LB liquid medium, of composition specified in Table 4 -but without agar, and stored at −80° C. It was shown by digestion of cosmids extracted from some 12 clones taken at random that the average size of the inserts of the library was approximately 37 kb.

2) Screening of the library by hybridisation with the fragment A

The fragment A containing the endothiapepsin structural gene was used as a probe for hybridisation experiments. Initially, the clones contained in the microtitration plates were subcultured in Petri dishes containing LB agar medium (see Table 4) with the addition of ampicillin, and then transferred onto nylon membranes (Hybond $N^+$, Amersham). The bacteria were then lysed using a solution containing 1.5M NaCl and 0.5M NaOH. After treatment with a solution of proteinase K (Sigma) for 30 min at 37° C., the filters are washed with 2×SSC (NaCl 17.5 g/l, sodium citrate 8.82 g/l, pH 7) and pre-hybridised at 42° C. for 20 min. The filters are hybridised at 42° C. overnight with the fragment A isolated in Example 1, labelled with horseradish peroxidase (Amersham), and are revealed with the "Gene detection system" ECL chemiluminescent probe kit (RPN 2101, Amersham). The hybridisation signals obtained are visualised on a suitable film. Of the 4,500 clones of the library, 2 clones gave a positive signal. These two clones, hereinafter designated 8H12 and 41H7 and containing, respectively, the cosmids referred to as p8H12 and p41H7, were subcultured on LB liquid medium containing 100 mg/l of ampicillin. After culturing overnight at 37° C., the cosmids are extracted by the method of lysis in an alkaline medium and purified by ultracentrifugation with caesium chloride and ethidium bromide according to the techniques described in Maniatis, op. cit. The cosmids thus purified were digested with the enzyme HindIII and the fragments obtained were subjected to electrophoresis on 0.8% agarose gel. Southern blotting on a nylon membrane was performed, and the filter was hybridised with the fragment A using the technique described above. The presence of this fragment in each of the cosmids p8H12 and p41H7 was thereby confirmed.

3) Physical analysis of the Positive cosmids p8H12 and p41H7

It was found that the restriction profiles of cosmids p8H12 and p41H7, obtained using the enzymes NotI, SmaI, SfiI, XbaI, BamHI and PvuI, were identical, thereby indicating that this region of the genomic DNA containing the gene coding for endothiapepsin of C. parasitica was cloned without rearrangement for these two clones. The restriction profile for cosmid p8H12, the cosmid adopted for the next part of the study, is given in Table 5 below.

TABLE 5

Restriction profile of cosmid p8H12

| Restriction enzyme | Number of cleavage sites | Size in kb | TOTAL in kb |
|---|---|---|---|
| NotI | 1 | not determined | — |
| SmaI | 2 | not determined | — |
| SfiI | 3 | 20; 16; 4.1 | 40.1 |
| XbaI | 4 | 23; 14; 2.9; 1.2 | 41.1 |
| BamHI | 5 | 15; 9; 7; 7; 2.6 | 40.6 |
| PvuI | 5 | 23; 7.4; 6.4; 2.1; 1.5 | 40.4 |
| | | Average | 40.6 |

This profile makes it possible to calculate the average size of cosmid p8H12, equal to approximately 40.6 kb, and hence that of the genomic insert, equal to approximately 40.6–8.0= 32.6 kb. This genomic insert is referred to as fragment B.

It was shown, moreover, by Southern blotting on a nylon membrane, that the approximately 9-kb BamHI—BamHI fragment (see Table 5), hereinafter referred to as fragment C, was the only BamHI—BamHI fragment to be hybridised with the fragment A used as a probe; it hence contained the whole of this fragment.

Section 3

Cloning of the fragment C, an approximately 9-kb fragment of genomic DNA containing the coding sequence of the endothiapepsin precursor.

10 μg of cosmid p8H12 were digested with the endonuclease BamHI and the different fragments were separated on 0.8% agarose gel.

The product of digestion with the enzyme BamHI, containing the fragment C, was ligated using T4 DNA ligase (Gibco BRL) to plasmid pBR322 opened at the BamHI site and dephosphorylated (marketed by Biolabs—ref. 320). The ligation product was used to transform competent cells of E. coli strain K12 RR1 (Gibco BRL ref. 520-8261A). After the transformation mixture has been plated out on Petri dishes containing LB agar medium supplemented with ampicillin (100 μg/ml), and incubation of the dishes at 37° C. for 24 h, the colonies are replicated on nylon membranes; the bacteria are then lysed and the membranes are thereafter hybridised with the fragment A, as described above in Section 2.2). 18 colonies containing DNA which hybridises with the fragment A were thereby detected. Their plasmid DNA content was extracted and analysed on 0.8% agarose gel after digestion with the endonuclease BamHI. It was thus verified that all these colonies contained a plasmid derived from pBR322 which had an approximately 9-kb fragment inserted at the BamHI site. A clone referred to as SEBR 3104, containing the plasmid designated pEp1, was chosen for the next part of the study. The clone SEBR 3104 was deposited with the CNCM under No. I-998.

Figure 4:
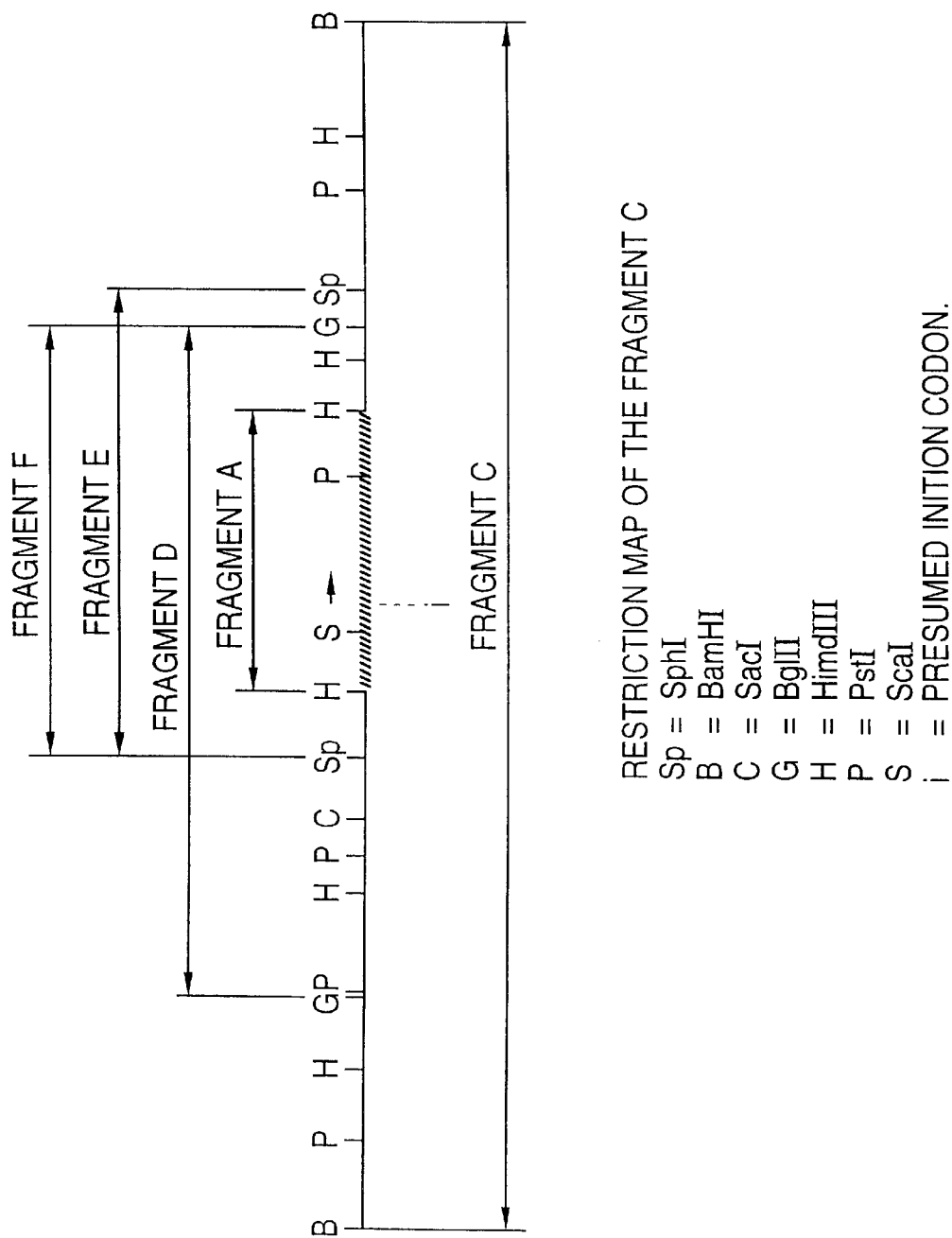
FIG. 4 shows a restriction map of the fragment C, the BamHI, HindIII, PstI, SphI, SacI, BglII and ScaI sites being symbolised by the letters B, H, P, Sp, C, G and S, as well as the fragments A, D, E and F contained in the fragment C.
Figure 6:
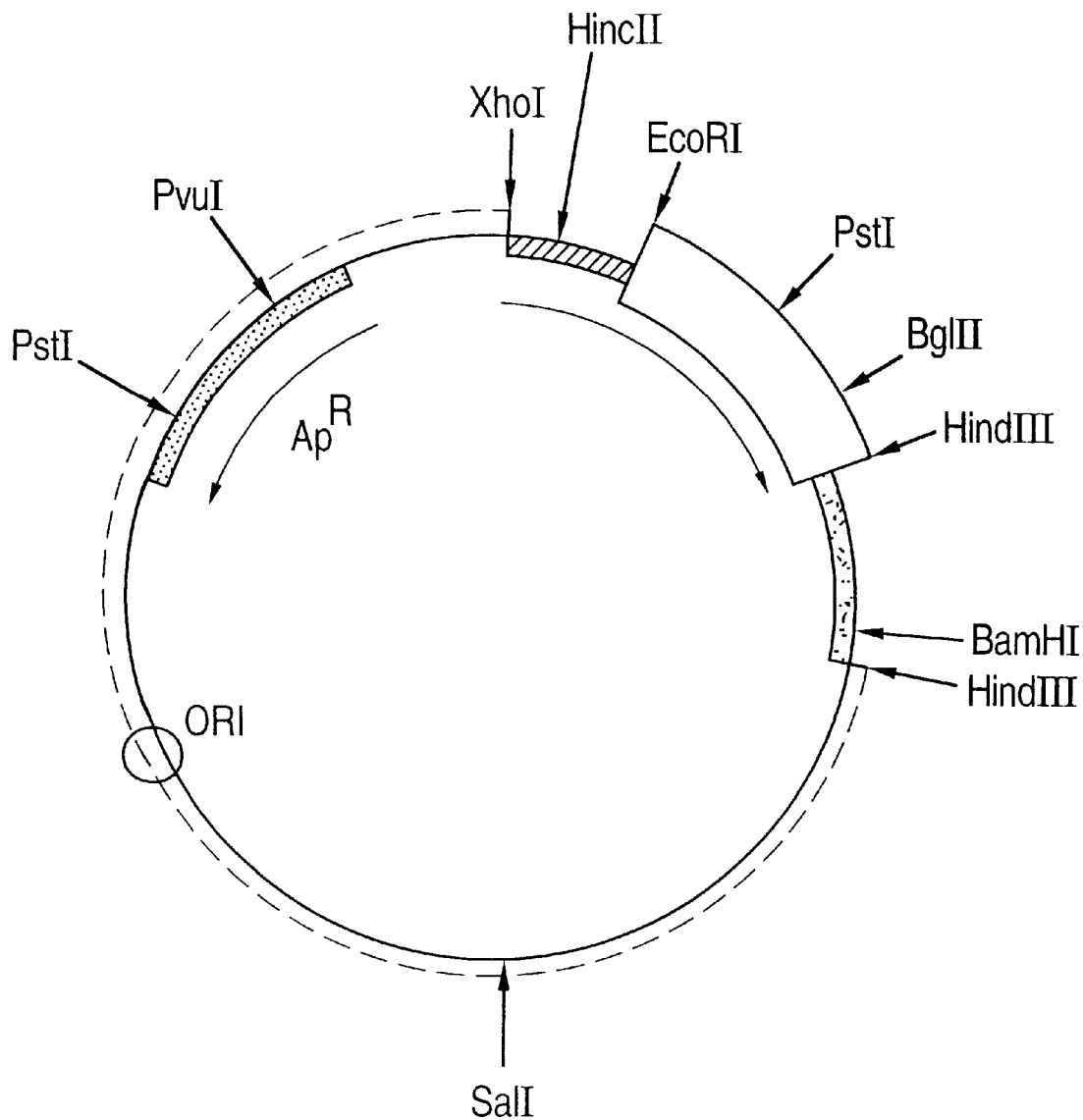
FIG. 6 shows a restriction map of plasmid p163,1. The different restriction segments are arbitrarily labelled according to the following legend.

Plasmid pEp1 was subjected to single and/or multiple digestions using the enzymes BamHI, HindIII, PstI, SacI, SphI, BglII and ScaI. The restriction map obtained is shown in FIG. 4, the symbols B, H. P, Sp, C, G and S representing, respectively, BamHI, HindIII, PstI, SphI, SacI, BglII and ScaI, the initiation codon of the endothiapepsin gene of C. parasitica being indicated by an i and the arrow indicating the direction of transcription of the endothiapepsin gene.

The fragment A described in Section 2, as well as the fragments D, E and F described in Sections 4 and 5, are also shown in this figure.

It is apparent that the BamHI site (B) which forms the 5' end of the fragment C is located approximately 4 kb from the initiation codon, and that the BglII site (G) on the 5' side is located approximately 3 kb from the initiation codon. It hence appears to be advantageous to isolate and clone the approximately 5.1-kb BglII-BglII fragment containing the whole of the fragment A, referred to as fragment D, and which probably contains the information necessary for expression of the endothiapepsin precursor.

Section 4

Cloning of the fragment D, an approximately 5.2-kb fragment of genomic DNA containing the coding sequence of the endothiapepsin precursor.

20 μg of plasmid pEp1 were digested with the enzyme BglII (see FIG. 4) and the digestion products were separated on 0.8% low-melting-temperature agarose (Sigma —Ref. A9414) gel. After staining of the agarose gel with ethidium bromide, the agarose band containing the approximately 5.2-kb fragment D is cut out with a scalpel under ultraviolet light at 310 nm. The DNA is then extracted according to the instructions in the NACS. 52PREPAC kit (Gibco BRL), and thereafter diluted in 10 μl of TE buffer of composition 10 mM Tris-HCl pH 8, 1 mM EDTA; 1 μl of the suspension obtained was ligated using T4 DNA ligase (Gibco BRL) to plasmid pBT6, derived from plasmid pBT3 by the insertion of a BglII linker at the SmaI site of the polylinker of pUC12. Plasmid pBT3, described by Orbach M. J. et al., 1986,Mol. Cell. Biol., 6, 2452–2461, carries a mutated gene for β-tubulin of Neurospora crassa (a filamentous ascomycete fungus) conferring benomyl resistance (dominant selection marker). Before ligation, plasmid pBT6 was linearised with the endonuclease BglII and dephosphorylated with alkaline phosphatase (Promega, Ref. CIP-M204).

The ligation product was used to transform competent cells of E. coli strain K12 RR1 (Gibco BRL Ref. 530-8261SA). After the transformation mixture has been plated out on Petri dishes containing LB agar medium supplemented with ampicillin (100 μg/ml), and incubation of the dishes at 37° C. for 24 h, the colonies are replicated on nylon membranes. The bacteria are then lysed, and the membranes are thereafter hybridised with the fragment A, as described in Section 2.2). Two colonies containing DNA which hybridises with the fragment A were thereby detected. Their plasmid DNA content was extracted and analysed on 0.8% agarose gel after digestion with the endonuclease BglII. It was thus verified that these two colonies contained a plasmid derived from pBT6 which had the approximately 5.2-kb fragment D inserted in both possible orientations at the BglII site. A clone containing this plasmid, designated plasmid pEp2, was chosen for the next part of the study.

Section 5

Cloning of the fragment F, an approximately 3.5-kb fragment of genomic DNA containing the coding sequence of the endothiapepsin precursor.

The cloning was carried out in two steps. First, the approximately 3.7-kb fragment E containing the whole of the fragment F was cloned into plasmid pUC18 at the SphI site of the polylinker. Plasmid pEp3 thereby obtained enabled the fragment F to be purified, which fragment was then subcloned in its turn into plasmid pUC18 at the BamHI site of the polylinker. Plasmid pEp4 was thereby obtained.

1) Construction of plasmid pEp3

1 μg of plasmid pEp1 was digested with the enzyme SphI (see FIG. 4), and the DNA was then purified with 0.1 volume of 3M sodium acetate and 2 volumes of ethanol. An approximately 3.7-kb SphI fragment, referred to as fragment E, was thereby obtained. The DNA was then dissolved in 40 μl of TE buffer of composition (10 mM Tris-HCl pH 8, 1 mM EDTA) and thereafter dialysed on a P10 column (Pharmacia). 1 μl of the mixture obtained above was then ligated using T4 DNA ligase (Gibco BRL) with approximately 25 ng of plasmid pUC18 previously linearised with the endonuclease SphI and dephosphorylated with alkaline phosphatase (Promega, Ref. CIP-M204). The ligation product was used to transform competent cells of E. coli strain DH5a (Gibco BRL, Ref. 530-8263 SA). After the transformation mixture had been plated out on Petri dishes containing LB agar medium supplemented with ampicillin (100 μg/ml), X-gal (40 μg/ml) and IPTG (2 μg/ml), and incubation of the dishes at 37° C. for 24 h, 350 white colonies were subcultured on the same medium. The colonies were then replicated on nylon membranes, the bacteria were thereafter lysed and finally the membranes were hybridised with the fragment A as described above in Section 2.2). 37 colonies containing DNA which hybridises with the fragment A were thereby detected.

The plasmid DNA of 30 clones was extracted and analysed on 0.8% agarose gel after digestion with the endonuclease SphI. Two colonies containing a plasmid derived from pUC18 which had the 3.7-kb fragment E inserted (in both possible orientations) at the SphI site were retained. These plasmids were referred to as pEp3(a) and pEp3(b). In plasmid pEp3(b), the BglII site of the fragment E is at a distance of approximately 3.5 kb from the BamHI site located on the polylinker of pUC18.

2) Construction of plasmid pEp4

10 μg of plasmid pEp3(b) were subjected to three successive digestions with the endonucleases BglII, BamHI and PvuI, and the digestion products were separated on 0.8% agarose gel. After staining of the gel with ethidium bromide, the agarose band containing the approximately 3.5-kb SphI fragment, designated fragment E, mixed with an SphI-BamHI fragment of the polylinker of pUC18, was cut out with a scalpel under ultraviolet light at 310 nm. The DNA is then extracted and thereafter dissolved in 20 μl of TE buffer of composition (10 mM Tris-HCl pH 8, 1 mM EDTA). 5 μl of the suspension obtained were ligated to approximately 750 ng of plasmid pUC18 previously linearised with the endonuclease BamHI and dephosphorylated with alkaline phosphatase. The ligation product was used to transform competent cells of E. coli strain DH5α according to the protocol described above. The plasmid DNA of 30 while colonies was extracted and analysed on 0.8% agarose gel after digestion with the endonucleases BamHI, BglII or SmaI. A colony was adopted which contains a plasmid derived from pUC18 which has the approximately 3.5-kb fragment F, mixed with an SphI-BamHI fragment of the polylinker of pUC18, inserted at the BamHI site. This plasmid was designated pEp4.

3) Determination of the sequence of the SphI-HindIII segment of the segment F

This sequence, determined as above (see Section 1), is shown in FIG. 12. It contains signals for activation of the promoter of the gene coding for preproendothiapepsin, as will be shown in Section 10.

Section 6

Transformation of C. parasitica with each of the vectors containing one of the fragments A, B and C.

Preparation of protoplasts

The mycelium originating from 250 ml of the culture broth of C. parasitica strain SEBR 103, prepared as described in Section 1, is rinsed with 50 ml of 1M $MgSO_4$. After incubation for 30 min at 37° C., the mycelium is filtered off on gauze and taken up in 20 ml of 1M $MgSO_4$. 20 ml of 1M MgSO4 containing 10 mg/l of the enzyme mixture CAYLASE C3 (company CAYLA), consisting of chitinases and β-1,3-, β-1,6-, α-1,3- and α-1,4-glucanases as well as other polysaccharidases, are then added and the resulting mixture is incubated for 1 h 30 min at 37° C. with gentle stirring. After filtration of the mixture, the filtrate is centrifuged for 10 min at 3,000 g, and the protoplast pellet obtained is then taken up in 15 ml of the buffer, referred to as ST buffer, of composition 0.8M sorbitol, 100 mM Tris-HCl, pH 7.5. After a further centrifugation for 10 min at 3,000 g, the pellet is taken up in 10 ml of a buffer, referred to as STC10 buffer, of composition 0.8M sorbitol, 100 mM Tris-HCl pH 7.5, 10 mM $CaCl_2$. The protoplasts are then counted using a Malassez cell, so as to adjust their concentration to $10^8$/ml after centrifugation for 10 min at 3,000 g and taking up the pellet in a buffer, referred to as STC50 buffer, of composition 0.8M sorbitol, 100 mM Tris-HCl pH 7.5, 50 mM $CaCl_2$.

Cotransformation of protoplasts with cosmid p8H12 and plasmid pBT3

Cosmid p8H12 which contains the fragment B (see Section 2) does not carry a dominant selection marker (usable for direct selection). Plasmid pBT3, described by Orbach M. J. et al., 1986, Mol. Cell. Biol., 6, 2452–2461, which carries a mutated gene for β-tubulin of *Neurospora crassa* (filamentous Ascomycete fungus) conferring resistance to benomyl (dominant selection marker) was hence used jointly with cosmid p8H12 (cotransformation method: see the work on cotransformation of *Aspergillus niger* of Wernars K. et al., 1987, Mol. Gen. Genet., 209, 71–77).

A mixture composed of 1 μg of plasmid pBT3, previously purified by ultracentrifugation in a buffer containing caesium chloride and ethidium bromide according to the techniques described in Sambrook, op. cit., and 4 μg of cosmid p8H12, purified in the same manner, in 10 ml of TE buffer of composition (10 mM Tris-HCl pH 8, 1 mM EDTA), is incubated for 20 minutes at 0° C. with 100 ml of the protoplast preparation prepared above (equivalent to $10^7$ protoplasts). After the addition of 1 ml of a solution consisting of 60% (weight/volume) of PEG 4000 (polyethylene glycol of molecular mass 4000) and buffer of composition 20 mM Tris-HCl pH 7.5, 100 mM $CaCl_2$, and incubation of the mixture for 10 min at room temperature, 1 ml of STC10 buffer (defined above) is mixed with the mixture. The protoplasts thus treated are included in 60 ml of agar medium containing 1 mg/l of Benlate (antifungal marketed by Dupont Nemours), referred to as medium D and whose composition is specified in Table 6 below, maintained supercooled at 45° C. The supercooled mixture is plated out on Petri dishes containing an agar medium supplemented with 1 mg/l of Benlate (antifungal marketed by Dupont Nemours which contains 50% of benomyl), referred to as medium C and whose composition is specified in Table 7 below. The Petri dishes are incubated at 28° C. for the time necessary for the appearance of benomyl-resistant regenerated protoplasts. The regenerated transformants thereby obtained are referred to as 29Pn, n designating the number of the clone under consideration. The benomyl resistance of the clones is confirmed by subculturing mycelial implants of each clone on medium B made into an agar medium by adding 20 g/l of agar and supplemented with 1 mg/l of Benlate.

Only the clones which grow on this medium are set up for sporulation according to the method described in Section 1.1). The conidiospres obtained are harvested in bulk in a buffer containing at least 15% of glycerol and stored at −80° C.

TABLE 6

Composition of medium D

| | | |
|---|---|---|
| Sucrose | 250 | g/l |
| Glucose | 20 | g/l |
| Thiamine | 2 | g/l |
| Asparagine | 100 | mg/l |
| Malt extract | 0.2 | g/l |
| Agar | 20 | g/l |
| Saline solution 1 (composition specified in Table 2) | 62.5 | ml |
| Adjust the pH to 6.0 using 1N HCl or 1N NaOH, | | |
| Autoclave for 30 min at 110° C., then | | |
| Add 1 mg/l of Benlate to the medium cooled to 60° C. | | |

TABLE 7

Composition of medium C

| | |
|---|---|
| Medium D | 750 ml/l |
| STC10 buffer | 250 ml/l |
| (of composition 0.8M sorbitol, 100 mM Tris-HCl pH 7.5, 10 mM CaCl₂) | |
| Adjust the pH to 6.0 | |
| Add 1 mg/l of Benlate to the medium autoclaved at 60° C. | |

Cotransformation of protoplasts with plasmid p472 and plasmid PBT3 on the one hand, as well as with plasmid pEp1 and plasmid pBT3 on the other hand Neither plasmid p472 which contains the fragment A (see Section 1) nor plasmid pEp1 which contains the fragment C (see Section 3) carries a dominant selection marker.

*C. parasitica* strain SEBR 103 was cotransformed according to a protocol identical to that described in the subsection above, with the following mixtures of plasmids: 4 µg of pEp1 and 1 µg of pBT3, 4 µg of p472 and 1 µg of pBT3. The transformants thereby obtained are referred to as 30Pn for the cotransformation with plasmids pEp1 and pBT3, and 31Pn for the cotransformation with plasmids p472 and pBT3, n designating the number of the clone under consideration.

Section 7

Selection of transformed strains over-productive of endothiapepsin.

1) General method a) Selection on agar medium containing casein

Mycelial implants of approximately 100 benomylresistant colonies were subcultured on an agar medium containing casein, referred to as medium E and whose composition is specified in Table 8 below. On this medium, *Cryphonectria parasitica* colonies which produce the protease give rise to a halo of precipitation whose area is proportional to the quantity of endothiapepsin secreted.

The overproductive strains are adopted on the basis of a ratio of the diameter of the halo of precipitation to the diameter of the colony, the ratio being significantly higher than that for the untransformed control strain. A preparation of conidiospores of these overproductive strains is made according to the method used in Section 1.1). In addition, it was verified by adding 5 µg/ml of pepstatin, a substance specifically inhibiting aspartic proteases, to medium E that the increase in the halos observed in the overproductive strains was reduced. This result shows that the observed effect is indeed due to an overproduction of an aspartic protease.

b) Selection in liquid medium

α) Study in flasks:

To confirm this result, tests of production in flasks were carried out in the following manner: inoculation of 250-ml flasks containing 40 ml of medium F whose composition is specified below. The flasks are then incubated at 28° C. on an eccentric rotary agitator adjusted to 220 rpm for 48 h. For each strain, culturing was carried out in 3 different flasks and the mean of the results of assay of coagulant activity for the 3 flasks was calculated. The control consists of untransformed *Cryphonectria parasitica* strain SEBR 103. The assay of coagulant activity is carried out according to the official method of determination of the enzyme content of coagulant solutions, published in the Journal Officiel de la République Française (Official Journal of the French Republic) of Mar. 20, 1981 (section C), summarised below:

1 ml of culture supernatant diluted with water so as to obtain a coagulation time of between 5 and 10 min is added to 10 ml of standardised milk (supplied by INRA—Experimental Dairy Station-39800 POLIGNY), placed in a suitable bottle;

the coagulation time, identified by the appearance of a flocculation of the milk on the wall of the bottle when rotated in a waterbath at 30° C., is measured;

the coagulant activity, designated CA, expressed in mg/l, is given by the formula:

$$CA = \frac{K}{T - a} \times \alpha$$

with K and a factors dependent on the milk and on the enzyme under consideration (expressed in mgs/l and in s, respectively).

T: coagulation time (expressed in seconds)

α: dilution factor.

β) Study under fermenter conditions

The production of endothiapepsin was assessed in a 2-l fermenter (Biolaffite) containing 1.2 l of a culture medium obtained by concentration of medium F, sterilised by autoclaving for 45 min at 120° C. The culture conditions are as follows: agitation at 800 rpm; aeration: 2 vvm (vvm: volume of air per volume of medium per min). The fermenter is inoculated in the proportion of 5% (v/v) with a flask pre-culture as described above (in α). The temperature is maintained at 28° C. Measurement of the coagulant activity is performed after approximately 90 h of fermentation according to the assay method described above.

It is verified by determination of the dry weight of the culture that the quantity of biomass produced by the overproductive transformants does not differ significantly from that produced by the control strain.

TABLE 8

Composition of medium E

| | | |
|---|---|---|
| KH₂PO₄ | 0.36 | g/l |
| Na₂HPO₄.2H₂O | 0.71 | g/l |
| MgSO₄.7H₂O | 0.50 | g/l |
| NaCl | 0.10 | g/l |
| Casein hydrolysate (Difco casamino acids) | 0.05 | g/l |
| Casein (Hammarsten) | 6.0 | g/l |
| CaCl₂ | 0.06 | g/l |
| Saline solution 2 (composition specified in Table 2 of Example 2) | 10 | ml/l |

TABLE 8-continued

Composition of medium E

Leave stirring for 15 min so as to
avoid foam formation.
Add 15 g of agar (Difco Bacto-agar).
Adjust the pH to 6.2 using 1N HCl or
1N NaOH.
Autoclave for 20 min at 120° C.

TABLE 9

Composition of medium F

| | |
|---|---|
| Cottonseed meal | 10 g/l |
| Glucose | 35 g/l |
| Ca(NO$_3$)$_2$ | 3.5 g/l |
| CaCO$_3$ | 0.75 g/l |
| Linseed oil | 2.5 ml/l |
| Sodium oleate | 1.5 g/l |

Adjust the pH to 6.20 using 1N HCl or
1N NaOH.
Autoclave for 45 min at 120° C.

Analysis of the enzyme secreted by the transformants

The fermentation must obtained after culturing (either in flasks or in fermenters) the overproductive transformants and the untransformed C. parasitica control strain SEBR 103 was subjected to a centrifugation so as to remove the mycelial mass. After denaturation of the proteins in the supernatant in the presence of SDS for 5 min at 100° C., electrophoresis was performed on polyacrylamide gel in the presence of SDS. After staining with Coomassie blue, a predominant band of molecular mass in the region of 36 kDa is observed, corresponding to the molecular mass of mature endothiapepsin deduced from its sequence (see FIG. 1) and more intensely stained in the case of the overproductive transformants than in the case of the control strain; and bands of lesser importance which are identical for the overproductive transformants and the control strain.

It was verified, moreover, by an antigen-antibody reaction (Rennetest kit, France Biochem) on the culture supernatants of the overproductive transformants and of the untransformed control strain that the secreted enzyme is identical to that of *Cryphonectria parasitica* according to the identification method described in the Journal Officiel de la Répulique Française (Official Journal of the French Republic) of Mar. 20, 1981.

In addition, the ratio of coagulant activity to proteolytic activity of the secreted enzyme was assessed. The coagulant activity, expressed in g/l, is measured according to the method described above in subsection b) α); the proteolytic activity, expressed as glycine milliequivalents per litre, is measured using the TNBS reagent, described by R. Fields, Biochem. J. (1971) 124: 518–590, by assaying the amino groups which have appeared after proteolysis of dimethylcasein.

This ratio is between 0.045 and 0.050 for the overproductive transformants, which is very close to that obtained with the untransformed control strain. It may be concluded from these three studies that endothiapepsin production is indeed the feature which has been specifically increased in the overproductive transformants.

c) Verification of the integration of the fragment A, B or C by Southern blotting.

The genomic DNA of the selected transformants is prepared according to a protocol similar to that described by Raeder and Broda, 1965, Letters in Applied Microbiology 1, 17–20, summarised below:

The mycelium originating from a flask culture performed as described in Section 1.1) is lyophilised and filtered off on gauze. After rinsing in 20 mM EDTA solution, pH 8, the mycelium is again filtered off, then frozen at −80° C. and lyophilised. 50 mg of the lyophilisate obtained are then ground and thereafter resuspended in 500 μl of the following extraction buffer: 200 mM Tris-HCl pH 8.5, 250 mM NaCl, 25 mM EDTA, 0.5% SDS, proteinase K (Sigma) 200 μg/ml. The mixture is incubated for 45 min at 45° C., and the DNA is then extracted with phenol/chloroform and then precipitated with isopropanol. The pellet is then taken up in 100 μl of TE (10 mM Tris-HCl pH 8, 1 mM EDTA).

The DNA is then digested with the appropriate endonucleases and the fragments obtained are separated by electrophoresis on 0.8% agarose gel. The fragments are transferred by capillarity onto a nylon membrane (Hybon N$^+$-Amersham) according to the method recommended by the manufacturer. The filters are then hybridised at 42° C. overnight with, successively, the fragment A and the HindIII-HindIII fragment containing the mutated gene for β-tubulin of Neurospora of plasmid pBT3, these fragments being labelled with horseradish peroxidase (Amersham) and revealed with the "Gene detection system" ECL chemiluminescent probe kit (RPN 2101, Amersham). The hybridisation signals obtained are visualised on a suitable film.

2) Selection of overproducers from among the 29Pn transformants (containing cosmid p8H12 which carries the fragment B—see Section 4)

164 benomyl-resistant colonies were obtained during the cotransformation with cosmid p8H12 and plasmid pBT3. 127 clones were chosen at random from among the latter for the selection test on agar medium containing casein, which enabled 14 clones to be adopted. From among the latter, 7 chosen at random were subjected to the selection test in liquid medium. 3 clones were thereby adopted; the clones 29P1, 29P2 and 29P3, possessing after flask culture a coagulant activity of 0.9, 1.07 and 0.94 g/l, respectively, whereas the untransformed control strain possesses an activity of 0.62 g/l (the overproduction factor, namely the ratio of the coagulant activity of the overproductive strain to the coagulant activity of the control strain is hence 1.45, 1.73 and 1.54, respectively). The clones 29P2 and 29P3 were then tested in a 2-1 fermenter, and produced a coagulant activity of 1.76 and 2.19 g/l, respectively, the control strain producing only 1.20 g/l (the overproduction factor is hence +1.47 and +1.83).

The clone 29P3 and the C. parasitica control strain SEBR 103 were cultured in a 20-1 fermenter under less limiting experimental conditions, especially as regards agitation, aeration and bulk transfer, and close to the conditions used in the industrial process.

This test enabled a quantity of endothiapepsin equal to approximately twice the quantity produced by the control strain to be obtained.

The 7 clones chosen above at random were analysed by Southern blotting. Their genomic DNA and that of the untransformed C. parasitica control strain SEBR 103 were digested with the enzyme SmaI, which generates only two cleavage sites in cosmid p8H12 and none in the fragment A. After hybridisation with the latter, two hybridisation bands were observed with the clones 29P1, 29P2 and 29P3 and a single hybridisation band, identical in size to one of the two bands mentioned above, with the control strain and the other clones not adopted after the selection test in liquid medium. The three overproductive clones 29P1, 29P2 and 29P3 have hence integrated a copy of cosmid p8H12 at a different locus of their genome, since the supernumerary bands observed differ in size. Finally, the Southern blot obtained above was hybridised with the HindIII fragment of plasmid pBT3 which confers benomyl resistance, and this enabled it to be established that the 7 benomyl-resistant clones all received at least one copy of plasmid pBT3, since they show several additional hybridisation bands compared with the control strain, the latter showing only one band corresponding to the endogenous β-tubulin gene (β-tubulin is a structural protein present in filamentous fungi, especially *Neurospora crassa* and *C. parasitica*).

These results show that the fragment B hence contains the signals necessary for the expression (and secretion) of endothiapepsin. It hence contains a functional gene for endothiapepsin, that is to say a sequence coding for an endothiapepsin precursor, flanked by a functional promoter and a functional terminator. This functional promoter hence comprises an activator region located upstream of the TATA box localised in the fragment A (see Section 1).

The addition of a further copy of this fragment to the genome of *C. parasitica* strain SEBR 103 by transformation enables transformed strains which overproduce endothiapepsin with a factor in the region of 2 to be obtained.

3) Selection of overproducers from among the 30Pn transformants (containing plasmid pEp1 which carries the fragment C: see Section 6)

663 benomyl-resistant colonies were obtained during the cotransformation with plasmid pEp1 and plasmid pBT3. 108 clones were chosen at random from among the latter for the selection test in agar medium containing casein, which enabled 32 clones to be adopted. It will be noted that this test enabled a markedly higher level (32/108) of overproducers to be adopted from among the 30Pn transformants than that obtained for the 29Pn transformants (14/127). This indicates that the frequency of cotransformation obtained with the approximately 13.4-kb plasmid pEp1 is greater than that obtained with the approximately 40.6-kb cosmid p8H12.

From among these 32 clones, 12 clones chosen at random were subjected to the selection test in liquid medium. 7 clones were thereby adopted: the clones $30P_1$, $30P_2$, $30P_3$, $30P_4$, $30P_5$, $30P_8$ and $30P_7$, possessing after flask culture a coagulant activity of 1.12, 1.06, 0.96, 1.12, 1.05, 0.88 and 0.90 g/l, respectively, whereas the untransformed control strain possesses an activity of 0.62 g/l (the overproduction factor is hence between +1.42 and +1.81).

The clones $30P_1$, $30P_2$ and $30P_5$ were then tested in a 2-1 fermenter, and produced a coagulant activity of 3.05, 3.0 and 3.04 g/l, respectively, the control strain producing only 1.20 g/l (the overproduction factor is hence +2.54, +2.50 and +2.53, respectively).

It is probable (see 2 above) that, under the non-limiting experimental conditions of the 20-1 fermenter, it would be possible to achieve an overproduction factor of approximately 3.

The 7 clones chosen above at random were analysed by Southern blotting. Their genomic DNAs and that of the untransformed *C. parasitica* control strain SEBR 103 were digested with the enzyme SacI, chosen since it generates only a single cleavage site in plasmid pEp1, a site localised in the fragment C outside the fragment A (see FIG. 4). After hybridisation for each of the 7 clones with the fragment A, at least two hybridisation bands (2 to 4 depending on the clone) were observed, including the band of the endogenous endothiapepsin gene also present for the control strain, the profile being different for each of the clones. For the clones $30P_1$, $30P_2$ and $30P_5$, a hybridisation band identical in size to that of the linearised plasmid pEp1 is observed among the bands, which indicates the probable integration in tandem of at least two additional copies of this plasmid.

It is, in effect, well known to those skilled in the art that the integration in tandem of several copies of a plasmid after transformation is a common event in filamentous fungi (Fincham J. R. S., March 1989,Microbiological Reviews, 148–170), and that digestion of the genomic DNA in which the plasmid has thereby been integrated, with an endonuclease generating only a single cleavage site in this plasmid, liberates this plasmid.

These results show that the fragment C contains all the signals necessary for the expression (and secretion) of endothiapepsin. It hence contains a functional gene for endothiapepsin, and hence a complete functional promoter. The promoter-activating region is hence located in the fragment C.

The addition of at least two further copies of this fragment to the genome of *C. parasitica* strain SEBR 103 enables transformed strains which overproduce endothiapepsin with a factor in the region of 3 to be obtained.

4) Selection of overproducers from among the 31Pn transformants (containing plasmid p472 which carries the fragment A: see Section 6)

840 benomyl-resistant colonies were obtained during the cotransformation with plasmid p472 and plasmid pBT3. 108 clones were chosen at random for the selection test on agar medium containing casein. In contrast to the results obtained above with the 29Pn and 30Pn cotransformants, no overproducer could be detected. Nevertheless, 5 clones $30P_1$, $30P_2$, $30P_3$, $30P_4$ and $30P_5$, chosen from among those giving a hydrolysis halo which was large but not significantly larger than that of the untransformed control strain, were subjected to the selection test in liquid medium. The abovementioned clones possess after flask culture a coagulant activity of 0.38, 0.66, 0.66, 0.56 and 0.65 g/l, respectively, whereas the control strain possesses an activity of 0.62 g/l (the difference found is hence −38, +6, +6, −22 and +4%). No significant overproduction is detected by this test in liquid medium, confirming the negative result of the selection test in casein agar medium.

Analysis by Southern blotting showed that the 5 clones integrated at least one copy of plasmid pBT3, and 3 clones out of 5 are genuinely cotransformed by plasmid pBT3 and plasmid p472. The addition of a further copy of the fragment A contained in plasmid p472 hence does not lead to an overproduction of endothiapepsin, which indicates that DNA sequences essential for the expression of endothiapepsin are lacking in this fragment. The fragment A hence does not contain a functional gene for endothiapepsin, which confirms that the fragment A lacks an activating region upstream of the promoter necessary for rendering the latter functional (see Section 1–7).

The activating region upstream of the promoter is hence located in the fragment C between its 5' end (BamHI site) and the 5' end (HindIII site) of the fragment A which it contains.

A more precise localisation of this activator region may be determined by obtaining a series of sub-fragments of the fragment C (prepared, for example, by digestion using endonucleases or exonucleases) comprising the fragment A flanked at the 5' end by different-sized segments of the portion of the fragment C bounded by the 5' end of the fragment A and a nucleotide located between the 5' end of the fragment A and the 5' end of the fragment C, transformation of *Cryphonectria parasitica* SEBR 103 with these subfragments and selection of the transformants expressing the recombinant protease. Examples of such subfragments of the fragment C are the fragments D and F, the preparation of which is described in Sections 4 and 5.

Section 8

Method of purification (removal of the selection marker) of a transformant over-productive of endothiapepsin, and of amplification of the gene coding for endothiapepsin by successive transformations.

1) Background

It is known (see, in particular, Fincham J. R. S., March 1989,Microbiological Reviews, 148–170) that fungal cells comprise several nuclei, in general containing the same genetic material. The protoplasts obtained after enzymatic digestion of their walls can be anucleate (incapable of regenerating), uninucleate or multinucleate. After transformation of the latter, it is hence possible to obtain transformed cells of the heterokaryon type, containing transformed nuclei, where appropriate of different kinds (depending on the mode of integration and the nature of the integrated material, which can vary) and untransformed nuclei. In the case of C. parasitica, the conidiospores are uninucleate (Puhalla J. E. et al., Phytopathology, 1971, 61, 169–173).

The work described below employs these characteristics of fungal cells to construct strains containing only the recombinant DNA of interest and not the selection marker.

2) Purification of the transformant 29P3 (removal of the selection marker) for the purpose of testing for benomyl-sensitive overproducers A preparation of conidiospores of the initial transformant overproductive of endothiapepsin 29P3 [see Section 1.1) and Section 7.2)], sufficiently dilute to obtain isolated colonies, was used to inoculate Petri dishes containing medium B (see Table 2 above) made into an agar medium by adding 20 g/l of agar. After incubation for 5 days at 30° C., mycelial implants of 50 colonies were subcultured in parallel on the same agar medium B and on the latter supplemented with 1 µg/ml of Benlate (containing 50% of benomyl). After incubation for 5 days at 30° C., 6 clones show normal growth on agar medium B and zero growth on agar medium B supplemented with Benlate. These 6 benomyl-sensitive clones, each derived from the germination of one spore, are of the homokaryon type, hence pure.

The 6 clones and the initial transformant 29P3 were subjected to the test of selection of overproduction of endothiapepsin on agar medium containing casein [see Section 7.1) a)], which enabled a benomyl-sensitive clone, referred to as 29P3 benS, to be selected, which clone shows an overproduction not significantly different from that of the initial transformant. The clone 29P3 ben$^S$, the clone 29P3 and the C. parasitica control strain SEBR 103 were subjected, after sporulation, to the selection test in liquid medium. The clones 29P3 and 29P3 ben$^s$ produce a coagulant activity which is identical (taking into account the margin of experimental error) but markedly greater than that of the control strain. In addition, Southern blotting performed on these two clones and the control strain, after digestion of their genomic DNA with the endonuclease SmaI, shows that each of the two clones have the same hybridisation profile with the fragment A as a probe, which profile contains a super-numerary band compared with the control (see Section 7.2)), indicating that in both clones the integration of the functional gene for endothiapepsin is identical, and a different hybridisation profile with the HindIII-HindIII fragment of plasmid pBT3 which confers resistance to benomyl (see Section 6), the initial transformant 29P3 showing several hybridisation bands with this fragment and the clone 29P3 ben$^S$ and also the control strain showing a single hybridisation band identical in size (corresponding to the endogenous gene for β-tubulin).

These results show that the purification method made it possible to obtain a transformant which was pure (as regards its genotype) and devoid of the selection marker (gene conferring benomyl resistance), and that the character of overproduction of endothiapepsin is integrated stably in the clone 29P3 ben$^s$ since it is derived from the germination of a uninucleate conidiospore and all the mycelial cells possess nuclei which have integrated cosmid p8H12 in their DNA.

3) Amplification

Protoplasts prepared from the clone 29P3 ben$^S$ were transformed with plasmid pBT3 according to the protocol described in Section 6. 400 benomyl-resistant clones were obtained for 1 µg of plasmid DNA.

It is hence possible to obtain, after cotransformation with a cosmid containing the functional gene for endothiapepsin and a plasmid containing a selection marker, a transformant which is overproductive of endothiapepsin and devoid of the selection marker, capable of being transformed again. It is hence possible, by performing several successive cycles comprising a step of cotransformation using the above two vectors followed by a step of purification enabling the selection marker to be removed, to amplify selectively in C. parasitica the gene coding for the endothiapepsin precursor.

Section 9

Testing for strains deficient in the production of endothiapepsin after transformation of C. parasitica SEER 103

An exhaustive analysis of the benomyl-resistant clones obtained after contransformation (see Section 6) of C. parasitica strain SEBR 103 with cosmid p8H12 and plasmid pBT3 enabled a clone to be obtained which did not produce a halo of hydrolysis on agar medium E containing casein. This clone was purified according to the method described in Section 8, and a large number of benomyl-sensitive clones which did not produce a halo of hydrolysis were obtained. One clone, designated 29P (end$^-$), was chosen at random from among these benomylsensitive clones. After flask culture, the clone 29P (end$^-$) possesses a coagulant activity of less than 0.01 g/l, whereas the untransformed Cryphonectria parasitica control strain SEBR 103 possesses a coagulant activity of 0.62 g/l (the observed fall in production is hence more than 98%). It was, in addition, observed that the morphological and physiological characteristics of this clone are modified relative to those of C. parasitica strain SEBR 103.

Southern blot analysis of the genomic DNA of the clone 29P(end$^-$) and of the control strain SEBR 103, after hybridisation with the fragment A on the one hand and the fragment containing the benomyl resistance gene of plasmid pBT3 on the other hand, showed no differences.

These results show that the clone 29P(end$^-$) selected and purified has been rendered deficient for the production of endothiapepsin after cotransformation of the C. parasitica strain with cosmid p8H12 and plasmid pBT3. It is seen to be obvious to those skilled in the art that transformants deficient in the production of endothiapepsin could be obtained by cotransformation of C. parasitica SEBR 103 with a selection marker, such as plasmid pBT3, and a DNA containing the preproendothiapepsin gene rendered non-functional, for example by deletion of a portion of the coding sequence, followed by selection of the benomyl-resistant transformants which do not produce a halo of hydrolysis of casein. Such a DNA carrying a non-functional gene may be readily obtained by linearisation of the DNA of plasmid pEp1, for example by performing an ScaI and SfiI double digestion, then purifying the largest fragment by electrophoresis on 0.8% agarose gel and finally treating the ends of this fragment with Klenow polymerase in the presence of the four deoxyribonucleotide triphosphates dNTP in order to permit a religation of the vector and thereby to obtain a plasmid carrying a non-functional gene for endothiapepsin.

Section 10

Construction of the strain SEBR 3700, deficient in the production of endothiapepsin and devoid of a dominant selection marker 1) Construction of a fragment, referred to as fragment EM, in which the sequence coding for endothiapepsin is interrupted by two translation stop codons.

At the beginning of the sequence coding for the endothiapepsin precursor, mutations were introduced bringing about a stoppage of translation, as a result of which endothiapepsin is no longer produced from the messenger RNA carrying these mutations. The fragment A of endothiapepsin comprises an approximately 360-bp HindIII-BstEII fragment (see FIG. 2), the BstEII site being localised 25 bp downstream of the beginning of the coding sequence. The natural sequence in question is as follows (SEQ ID NO:16):

```
                                    BsteII
                                      |
5'-G ATG TCT TCC CCT CTC AAG AAC GCC TTG GTG ACC
```

The underlined ATG triplet represents the codon opening the coding frame. The BstEII site is indicated by a vertical line.

The desired mutated sequence (SEQ ID NO:17) is:

```
                                    BsteII
                                      |
5'-G ATG TCT TCC CCT CTC TAA TGA ACG CCT TGG TGA CC
```

This sequence differs from the natural sequence by the introduction of 2T, one between the 5th and 6th codon, the other within the 6th codon (between the 2nd and the 3rd base). These introductions result in the creation of 2 stop codons stopping the reading frame of the endothiapepsin gene.

A HindIII-BstEII fragment differing from the wild-type sequence only in these two modifications was obtained by the PCR amplification technique described in Section 15, using for one of the primers an oligonucleotide carrying the desired mutations.

Oligonucleotide 1 has the following sequence (SEQ ID NO:18):

```
         HindIII
           |
5' - GCT AAA GCT TAT CCG CCG CCG GCG GGG GAA TTC
```

This sequence is to be found at the HindIII end of the HindIII-BstEII fragment. The HindIII site is designated by a vertical line.

Oligonucleotide 2 has as its sequence (SEQ ID NO:19):

```
BamHIBstEII    BamHI    BsteII
    |            |        |
    5' - CAA TGG ATC CGG TCA CCA AGG CGT TCA TTA GAG AGG GGA AGA
CAT C
```

This oligonucleotide is complementary to the desired mutated sequence; a BamHI site flanking the natural BstEII site has been attached to it. The underlined nucleotides correspond to the additions creating the stop codons on the complementary strand.

The DNA used as a template is the DNA of plasmid p472 described in Section 1. The amplification mixture comprises:

300 ng (equivalent to 3 µl) of p472 DNA
100 ng (equivalent to 1 µl) of each oligonucleotide
5 µl of buffer bipv2 concentrated 10-fold
40 µl of water
2 units (equivalent to 0.5 µl) of enzyme: Taq polymerase.

The buffer bipv2 10-fold concentrated has the following composition: 670 mM Tris-HCl pH 8.8; 165 mM ammonium sulphate; 10 mM 2-mercaptoethanol; gelatin 2 mg/ml; Triton X-100 1.5%; 67 µM EDTA; 20 mM MgCl$_2$; 2 mM DATP; 2 mM dCTP; 2 mM dGTP; 2 mM dTTP.

Three amplification tests are carried out in parallel. 15 amplification cycles are performed, each cycle being divided into 1 min of denaturation at 92° C., 1 min of hybridisation at 55° C. and 1 min of elongation at 72° C. After PCR amplification, the 3 tubes are combined in 1 Eppendorf tube and precipitated with 2 volumes of absolute ethanol containing 0.3M ammonium acetate (for 20 min at 0° C.), then centrifuged at 10,000 g (for 20 min). The pellet is washed with 70% ethanol and then dried under vacuum for 10 min.

The DNA is taken up in 60 µl of TE solution (10 mM Tris-HCl pH 7.5, 1 mM EDTA) and analysed on agarose gel. The band corresponding to the 360-bp fragment is eluted from the gel, purified and cloned into the replicative form of a phage M13 (Ml3mpl9) between the HindIII and BamHI sites after the action of these enzymes.

The fragment thus cloned was sequenced from the single-stranded fragment, and it was verified that the sequence did indeed correspond to the fragment mutated at the expected points.

The approximately 2.1-kb fragment A described in Section 1 is bounded by 2 HindIII sites and possesses a single BstEII site localised at 360 base pairs from one end. The single BstEII site hence bounds two segments of the fragment A; the shorter corresponds to the sequence subjected to PCR amplification. By preparing the large, BstEII-HindIII segment of the fragment A and the mutated, small, HindIII-BstEII segment, and ligating the whole in pBR322 cut with HindIII, a fragment A carrying the two mutations, referred to as fragment A-M, is thereby reformed.

The fragment A-M possesses a PstI site which is unique for this fragment. This PstI site hence bounds 2 segments of the fragment A-M, including an approximately 1.67-kb HindIII-PstI segment which carries the double mutation.

Plasmid pEp3 described in Section 5 is derived from a pUC plasmid into which an approximately 3.7-kb SphI fragment, referred to as fragment E, has been cloned. This 3.7-kb fragment comprises the fragment A as a subfragment. This fragment A was replaced by the fragment A-M in the following manner:

Plasmid pEp3b was digested both with the enzymes ScaI and PstI on the one hand and the enzymes ScaI and HindIII on the other hand. From the first digestion, the approximately 2.250-kb ScaI-PstI fragment was isolated. From the second digestion, the approximately 2.42-kb ScaI-HindIII fragment was isolated. Ligation of these 2 fragments with the 1.67-kb HindIII-PstI segment carrying the double mutation enables a new plasmid, referred to as pEpM3b, which differs from pEP3b only in the double mutation, to be obtained.

The SphI fragment carrying the double mutation, referred to as fragment E-M, was prepared from an SphI digestion of pEpM3b followed by a separation of the 2 DNA fragments on 0.8% agarose gel and extraction of the mutated 3.7-kb fragment in 20 µl of TE solution.

2) Cotransformation of *Cryphonectria parasitica* with the fragment EM and the SfiI fragment carrying a benomyl resistance gene flanked by telomeric sequences.

The purified fragment EM was used in cotransformation with the DNA of plasmid p578.12 digested with SfiI.

Plasmid p578.12 is a derivative of plasmid pBT3 already-described. The DNA of pBT3 was linearised with the endonuclease XhaI and the ends were rendered blunt with Klenow DNA polymerase. In it was integrated an XhaI fragment, repaired with the polymerase and which comprises the telomeric sequences of Tetrahymena originating from plasmid pPAT ura described by Perrot, Barreau and Bégueret Mol. Cel. Biol. (1987) 7 p. 1725–1730, modified so as to replace the BamHI sites by SfiI. Digestion of p578.121 with SfiI liberates a linear fragment which carries a benomyl resistance gene and which terminates at each of its ends with a telomeric sequence. Perrot et al. (ref. above) showed that such a fragment could be maintained in the state of a linear plasmid (not integrated in the chromosome) in the filamentous fungus *Podospora anserina*. Moreover, Powell and Kistler (J. Bacteriology, 1990, vol. 172, pp 3163–3171) showed that repeated sequences of the telomeric type permitted the autonomous replication of linear plasmids in *C. parasitica*. This property was turned to good account in order to construct appropriate strains by cotransformation with the linear fragment. The absence of integration of the benomyl resistance marker in the chromosome should enable benomyl-sensitive strains to be recovered with a very great frequency from the conidia obtained after sporulation of the transformants.

2 cotransformation experiments were carried out on *Cryphonectria parasitica* strain SEBR 103 with, for each one, approximately 0.5 $\mu$g (3 $\mu$l) of the fragment E-M and 0.5 $\mu$g (4 $\mu$l) of the SfiI fragment of plasmid p578.12. 397 benomyl-resistant colonies were obtained. 395 of these colonies were subcultured on medium E (see Section 7) to test for the presence of a halo as described in Section 7.

One colony no longer forming a halo of coagulation of casein was found; this colony, referred to as colony AJ7.272, was transferred onto sporulation (conidiation) medium according to the method described in Section 1. The conidiospores were harvested in bulk and diluted with the germination medium. 152 colonies derived from the conidiation were tested on casein medium: none of them showed a halo of coagulation. The benomyl resistance of these colonies was also tested: 58 of the 152 had lost this transformation character. 5 of the 58 were taken; they were referred to as colony AJ7272/A, colony AJ7272/B, colony AJ7272/J, colony AJ7272/L and colony AJ7272/M. The genomic DNA was extracted from each colony, and the hybridisation profiles and that of the strain SEBR 103 were compared by the Southern blotting technique, using various restriction enzymes. No difference was found between the strain SEBR 103 and the 5 mutants, probed with the fragment A (endothiapepsin gene), with pUC18 (bacterial sequences) or with the gene for beta-tubulin of Neurospora. With the fragment A, the sequences of the endothiapepsin gene are revealed; since the hybridisation profile is the same in all the strains, it may be concluded that there is no “ectopic” recombination of the mutated fragment (that is to say non-homologous recombination) in the mutants. With pUC18, no hybridisation is obtained, irrespective of the strain, which indicates that no sequence of bacterial origin remains integrated in the mutants. With the β-tubulin gene, a sequence is revealed in all the strains; this very probably corresponds to the “endogenous” gene for β-tubulin of *C. parasitica*.

In order to check that the strains derived from the colony AJ7272 were indeed mutated in the endothiapepsin structural gene, it was verified that their lack could be complemented by transformation. Each of the above colonies was used as a receptor for a cotransformation involving the DNAs of plasmid pBT3 and of plasmid pEP2.

The following table shows that the majority of benomyl-resistant transformants obtained in this manner again produce endothiapepsin.

| Strain | Benomyl-resistant colonies (test on casein) | Colonies productive of protease |
|---|---|---|
| AJ7.272/A | 2 | 2 |
| AJ7.272/B | 8 | 7 |
| AJ7.272/J | 13 | 11 |
| AJ7.272/L | 17 | 16 |
| AJ7.272/M | 10 | 10 |

Control: transformation of the segregants with plasmid pBT3 alone gives no transformant productive of protease.

Analysis of the culture supernatants by acrylamide gel electrophoresis confirmed that the mutated strains did not produce a detectable amount of endothiapepsin before transformation.

A strain AJ7.272 which, after sporulation, gave rise to 5 colonies which differ from the strain SEBR 103 only in one or more mutations affecting the endothiapepsin structural gene was hence constructed. One of these colonies was adopted. It is referred to as SEBR 3700. It is deficient in the production of endothiapepsin and devoid of a dominant selection marker.

Section 11

Verification of the functionality of the fragments D and F by complementation of the strain SEER 3700 deficient in the production of endothiapepsin.

It was demonstrated in Section 7, subsection 3, that the fragment C contained in plasmid pEp1 carries all the signals necessary for the expression of endothiapepsin. Using the strain SEBR 3700 deficient for the production of endothiapepsin, obtained in Section 10, the functionality of the fragments D and F contained in plasmids pEp2 and pEp4 was verified.

1) Transformation of protoplasts of the strain SEBR 3700 with plasmids pEp2 and pBT3

Plasmid pEp2 carries both the benomyl resistance gene and the fragment D, and can hence be used directly for transformation. Plasmid pBT3 which does not carry a gene coding for endothiapepsin is used as a negative control. The strain SEBR 3700 was transformed according to a protocol identical to that described for the strain SEBR 103 (see Section 6) with approximately 1 μg of plasmid pEp2 and 1 μg of plasmid pBT3.

2) Cotransformation of protoplasts of the strain SEBR 3700 with plasmids pEp1 and PBT3 and plasmids pEp4 and pBT3.

Plasmids pEp1 and pEp4 do not carry a dominant selection marker. Plasmid pEp1 is used as a positive control-of complementation of the strain SEBR 3700.

The strain SEBR 3700 was cotransformed with the following mixtures of plasmids: 4 μg of pEp1 and 1 μg of pBT3, 4 μg of pEp4 and 1 μg of pBT3.

3) Detection of transformants producing endothiapepsin

Mycelial implants of several transformants selected for each of the transformations and cotransformations described above were subcultured on medium E, an agar medium containing casein. After incubation, the colonies showing a halo of precipitation characteristic of the secretion of endothiapepsin were identified. The results obtained are as follows:

- transformants obtained with plasmid pBT3: no clone gave a halo of precipitation
- transformants obtained either with plasmids pEp1 and pBT3, or with plasmids pEp4 and pBT3: a proportion of approximately 30% of the clones gave halos of precipitation
- transformants obtained with plasmid pEp2: 92% of the clones tested gave halos of precipitation.

These results show that plasmids pEp1, pEp2 and pEp4 complement the strain SEBR 3700 deficient in the production of endothiapepsin, and hence that the fragments C, D and F contained in these plasmids all carry a functional promoter of endothiapepsin. However, the relative strength of the promoter present in each of the fragments cannot be deduced from this qualitative test.

It may be deduced from these results that the SphI-HindIII segment of the fragment F, the sequence of which has been determined in Section 5, possesses signals involved in the activation of the promoter of the gene coding for preproendothiapepsin.

Section 12

Selection of transformants overproductive of endothiapepsin and devoid of a dominant selection marker.

1) Selection protocol

The different steps of the protocol are shown in the table below. Its principle is as follows:

- *C. parasitica* SEBR 103 protoplasts are cotransformed, according to a protocol identical to that described in Section 6, with a mixture composed of 0.5 to 2 μg of fragment C, D or F, previously purified on agarose gel after digestion of plasmids pEp1 or pEp2 and extracted according to the instructions of the Biorad Gene-clean kit, and 0.5 μg of the selection plasmid pBT3 or pBT6, either in circular form or in linear form.

After regeneration of the protoplasts on medium C, the transformants obtained, which are designated initial transformants, are simultaneously subcultured on medium B made into an agar medium by adding 20 g/l of agar (non-selective medium) and on medium E, an agar medium containing casein, where appropriate supplemented with 5 μg/ml of pepstatin. The clones possessing a ratio of the diameter of the halo of precipitation to the colony diameter significantly higher than that of the untransformed control strain are designated overproductive initial transformants and are set up for sporulation. A preparation of conidiospores of these strains is made according to the method used in Section 1.1, and a dilution of each conidiospore suspension is plated out on medium G so as to obtain isolated colonies. Mycelial implants originating from about fifty colonies are subcultured for each overproductive initial transformant, simultaneously on medium B made into an agar medium by adding 20 g/l of agar, where appropriate supplemented with 0.5 mg/l of Benlate (benomyl sensitivity test) and on medium E (test on casein medium). At this stage, the clones which are sensitive to benomyl and overproductive of endothiapepsin are designated overproductive benomyl(s) segregants and are set up for sporulation. A conidiospore preparation is then made in order to verify the overproduction of endothiapepsin after culturing in flasks, to verify the integration of one or more copies of the fragment C, D or F by hybridisation of the genomic DNA with a probe consisting of the fragment A, and to check the absence of heterologous DNA using a probe consisting of all or part of the selection plasmid. The strain satisfying these three criteria positively is designated overproductive appropriate strain. A further cycle of cotransformation/selection may then be performed from this overproductive appropriate strain in order to amplify again the fragment C, D or F.

The advantage of this process, in addition to that obtained by amplification of the fragment of interest, is to construct transformants devoid of a dominant selection marker, which are more acceptable from the standpoint of statutory regulations.

Protocol for the selection of overproductive transformants devoid of a dominant selection marker

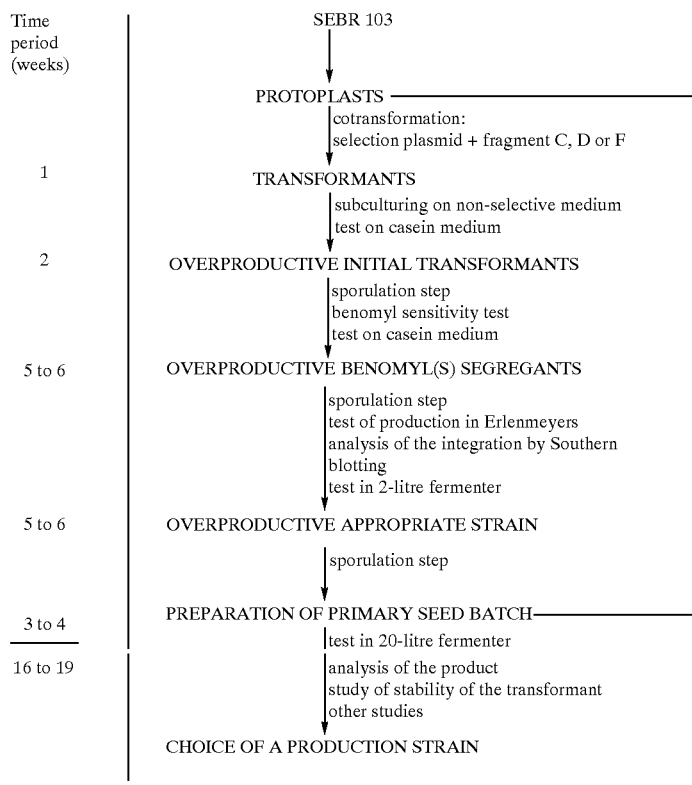

2) Selection of overproductive transformants devoid of a dominant selection marker after cotransformation of SEBR 103 with the fragment C, D or F and plasmid pBT3

The following table summarises the results obtained

| Cotransformation | Fragment F | Fragment C | Fragment D |
|---|---|---|---|
| Quantity | 0.5 µg | 2 µg | 0.5 µg |
| Selection plasmid | circular | circular | linear |
| Initial transformants | 4 | 137 | 106 |
| Overproductive initial transformants | 1 | 26 | 33 |
| Benomyl(s) segregants | 1 | 4 * | 8 ** |
| Overproductive benomyl(s) segregants | 0 | 2 | 7 |
| overproductive appropriate strains | 0 | 1 | 4 |

No overproductive appropriate strain could be obtained with the fragment C, which is not surprising in view of the low number of initial transformants.
* selection performed on the progeny of 12 overproductive initial transformants
** selection performed on the progeny of 21 overproductive initial transformants The overproductive appropriate strain obtained with the fragment D was tested in a 2-litre fermenter and produced a coagulant activity of 1.9 g/l, the control strain producing only a coagulant activity of 1.2 g/l (the overproduction factor is hence +1.58). Analysis of the genomic DNA by Southern blotting of the strain SEBR 3574 showed that it had integrated at least 3 additional copies of the fragment D, including 2 copies in tandem.

Among the four overproductive appropriate strains obtained with the fragment F, the strain SEBR 3912 was tested in a 2-litre fermenter and produced a coagulant activity of 2.4 g/l (the overproduction factor relative to the control strain is hence +2). Analysis of the genomic DNA by Southern blotting showed that it had integrated at least 5 additional copies of the fragment F, in tandem according to a head-to-tail orientation.

In the overproductive strains obtained, no integration of the selection plasmid was detected. These strains may hence be subjected to a further cycle of cotransformation/selection. Furthermore, if the over-production factor observed for these strains is compared with the presumed number of copies integrated, it is found that the ratio obtained is in the region of 0.2, whereas it is approximately 1 for the 30Pn transformants which have integrated two additional copies of plasmid pEp1 containing the fragment C. This hence suggests that, upstream of the BglII site located at the 5' end of the fragment D up to the BamHI site, there are regulatory sequences which are important for a strong expression of the endothiapepsin gene.

Section 13

Construction of plasmid pEMR713, a vector for the expression of preproendothiapepsin in C. parasitica which comprises the promoter region of the gene coding for glyceraldehyde-3-phosphate dehydrogenase of Aspergillus nidulans Plasmid pAN52 (Punt et al., 1987, Gene, 56, 117–124) carries, in addition to the gene coding for ampicillin resistance and the origin of replication of pUC18, the promoter region of the gene coding for glyceraldehyde-3 -phosphate dehydrogenase (gpd) of *Aspergillus nidulans* [Punt et al., gene, 93, (1990) 101–109] and the terminator region of the trpC gene of *Aspergillus nidulans* [Mullaney et al., Mol. Gen. Genet. (1985) 189; 37–45]. The promoter region and the terminator region are separated by a DNA sequence which comprises nucleotide sequences recognised by the restriction enzymes NcoI and MluI, which sequences are unique in plasmid pAN52. The sequence of the NcoI site, namely CCATGG, is especially useful inasmuch as it comprises the ATG codon which codes for a methionine which is the initiation codon for the majority of proteins.

The aim of this experiment is to express the gene coding for endothiapepsin using the expression signals described above. Integration of the gene coding for endothiapepsin is carried out by the PCR (polymerase chain reaction) technique, which is described in detail in Section 15 below.

1—Description of the primers used for the PCR Gene amplification by PCR permits modification of the sequence to be amplified. This property is used in order to introduce an NcoI site at the 5' end of the prepro sequence of the gene coding for endothiapepsin, and an MluI site at the non-coding 3' end of the gene coding for endothiapepsin. The sequences of the two primers are hence as follows:

- 5' primer carrying the NcoI site SEQ ID NO:20:

5'-ACG-TCC-ATG-GCT-TCC-CCT-CTC-AAG-AAC-GCC-3'

This primer consists mainly of:
 a) The sequence recognised by the restriction enzyme NcoI: CCATGG
 b) The modified sequence of the 5' end of the signal peptide of endothiapepsin.

The modification consists in the change of the first codon after the methionine; in effect, the TCT codon coding for a serine is replaced by the GCT codon coding for an alanine. This modification has no effect on the efficacy of the signal peptide.

- 3' primer carrying the MluI site SEQ ID NO:21:

5'-ACG-TAC-GCG-TCC-ACG-CCT-ACC-CAA-CAA-GAC-3'

This primer consists mainly of:
 a) The sequence recognised by the restriction enzyme MluI: ACGCGT
 b) The sequence of the non-coding 3' end of endothiapepsin, which is the sequence complementary to the sequence located between nucleotides 1921 and 1940 of FIG. 2.

2—Production of the amplified fragment containing the gene coding for modified endothiapepsin Plasmid p472, the production of which is described in Section 1, is used as a template.

a) The PCR reaction 100 ng of plasmid p472, previously purified on a P10 column, are mixed with 100 ng of the 5' primer, 100 ng of the 3' primer, 2 mM $MgCl_2$, 0.2 mM dNTP and 5 µl of reaction mixture concentrated 10-fold (final quantity: 67 mM Tris-HCl pH 8.8, 16.6 mM $(NH_4)_2SO_4$, 1 mM β-mercaptoethanol, 6.7 mM EDTA, 0.15% Triton X-100, 200 g/ml of gelatin).

The volume of the mixture is then brought to 50 µl by adding water.

The reaction mixture thereby obtained is incubated for 4 min at 94° C. and then brought to a temperature of 50° C., which is maintained for 4 min.

0.5 µl, equivalent to 2.5 units, of Taq polymerase (Boehringer Mannheim Ref. 1146-165) is then added. The reaction mixture is then covered with paraffin in order to prevent evaporation of the aqueous solution.

The amplification is carried out during 18 reaction cylces, the steps of which are as follows:
 2 min at 92° C.→denaturation
 2 min at 50° C.→hybridisation
 2 min at 72° C.→polymerisation.

After the 18 cycles, the enzymatic reaction is stopped by adding 20 mM EDTA solution.

The DNA fragment thus amplified, which possesses the expected size of approximately 1620 bp, is then isolated and purified on 1% agarose gel, dialysed on a P10 column (Pharmacia) and then hydrolysed simultaneously with the enzymes NcoI and MluI. After hydrolysis, the fragment is purified on a P10 column.

b) Production of plasmid pEMR713

The DNA of plasmid pAN52 is hydrolysed with the restriction enzymes NcoI and MluI. The fragment carrying the promoter region of the gpd gene, the origin of replication of *E. coli*, the gene coding for ampicillin resistance and the trpC terminator is purified. 100 ng of this fragment are ligated in the presence of DNA ligase to 100 ng of the amplified fragment carrying the endothiapepsin gene (see subsection 2 above). The ligation mixture is then used to transform the strain RRI. The resulting plasmid is pEMR713 in which the gene coding for modified endothiapepsin is placed under the control of the promoter region of gpd and the terminator region of trpC.

Preparation of protoplasts
 see Section 6

Cotransformation of protoplasts of the strain SEBR 3700 with plasmid DEMR713 and plasmid pBT3
 see Section 6

Approximately 2,000 transformants obtained are capable of growing on agar medium B containing 0.5 mg/l of Benlate, which indicates that all these colonies carry at least one plasmid pBT3.

Selection of transformed strains productive of endothiapepsin

A) General method
a) Selection on agar medium containing casein

Mycelial implants of the 2,000 benomyl-resistant colonies are subcultured on an agar medium containing casein, referred to as medium E and whose composition is specified in TABLE 8 above . On this medium, the *Cryphonectria parasitica* colonies which produce the protease give rise to a halo of precipitation whose area is proportional to the quantity of endothiapepsin secreted.

The productive strains are adopted on the basis of the presence of the halo of precipitation. A preparation of conidiospores of these productive strains is made according to the method used in Section 1.1). In addition, it was verified by adding 5 µg/ml of pepstastin, a substance specifically inhibiting aspartic proteases, to medium E that the increase in the halos observed in the overprodutive strains was reduced. This result shows that the observed effect is indeed due to an overproduction of an aspartic protease.

3 transformants capable of producing a halo of coagulation were isolated. Control experiments show that the size of the halo of the recombinant clones transformed with plasmids pBT3 and pEMR713, referred to as clone 1, clone 2 and clone 3, is comparable to that obtained for the strain SEBR 103.

b) Selection in liquid medium by a study in flasks

To confirm this result, tests of production in flasks were carried out in the following manner: inoculation of 250-ml flasks containing 40 ml of medium F (see Section 7). The flasks are then incubated at 28° C. on an eccentric rotary agitator adjusted to 220 rpm for 48 h. For each strain, culturing was carried out in 3 different flasks and the mean of the results of assay of coagulant activity for the 3 flasks was calculated. The control consists of untransformed *Cryphonectria parasitica* strain SEBR 103. The assay of coagulant activity is carried out according to the official method of determination of the enzyme content of coagulant solutions, published in the Journal Officiel de la République Française (Official Journal of the French Republic) of Mar. 20, 1981 (section C), summarised in Section 7.

c) Analysis of the enzyme secreted by the clones 1, 2 and 3

The fermentation must obtained after culturing the productive transformants and that of the untransformed *C. parasitica* control strain SEBR 3700 were subjected to a centrifugation so as to remove the mycelial mass. After denaturation of the proteins in the supernatant in the presence of SDS for 5 min at 100° C., an electrophoresis was performed on polyacrylamide gel in the presence of SDS. After staining with Coomassie blue, a predominant band of molecular mass in the region of 36 kDa is observed, corresponding to the molecular mass of mature endothiapepsin, deduced from its sequence (see FIG. 1), of the same intensity in the case of the productive transformants as in the case of the control strain, and bands of lesser importance which are identical for the overproductive transformants and the control strain.

It was verified, moreover, by an antigen-antibody reaction (Rennetest kit, France Biochem) on the culture supernatants of the overproductive transformants and of the untransformed control strain that the secreted enzyme is identical to that of *Cryphonectria parasitica* according to the identification method described in the Journal Officiel de la République Française (Official Journal of the French Republic) of 20th Mar. 1981.

In addition, the ratio of coagulant activity to proteolytic activity of the secreted enzyme was assessed. The coagulant activity, expressed in g/l, is measured using the TNBS reagent, described by R. Fields, Biochem. J. (1971) 124: 581–590, by assaying the amino groups which have appeared after proteolysis of dimethylcasein.

This ratio is between 0.040 and 0.045 for the overproductive transformants, which is very close to that obtained with the untransformed control strain. It may be concluded from these three studies that endothiapepsin has indeed been specifically produced by the clones 1, 2 and 3.

This experiment shows that it is possible to express in *C. parasitica* the gene coding for endothiapepsin, using a promoter region and a heterologous terminator region (not belonging to *C. parasitica*).

Section 15

Amplification by the PCR technique of the complementary DNA coding for the endothiapepsin precursor.

1) Isolation of the messenger RNAs of *C. parasitica*

*C. parasitica* strain SEBR 103 was cultured under conditions of production of endothiapepsin. The mycelium was recovered by filtration on gauze, washed with water and frozen in liquid nitrogen.

15 g of frozen mycelium (wet weight) are suspended in 45 ml of lysis buffer and then taken up in the same volume of beads (0.45 µm in diameter). The lysis buffer consists of 4M guanidine thiocyanate, 10 mM Tris-HCl pH 7.6, 10 mM EDTA and 50 mg/l β-mercaptoethanol. The mycelial suspension is ground for 5 min.

The ground preparation is recovered and the beads removed after settling has taken place. Approximately 45 ml of supernatant are withdrawn, lithium chloride is added to a final concentration of 3M and the preparation is stored at 0° C.

After two days, the above solution is centrifuged for 60 min at 10,000 rpm. The supernatant is withdrawn and the pellet is taken up in 40 ml of 3M LiCl. The suspension obtained is recentrifuged at 10,000 rpm for 1 h 30 min. Proteinase K (SIGMA) 40 µg/ml, SDS (0.1% w/v) and 20 mM EDTA are added. The mixture is incubated at 37° C. for 3 h. Precipitation is performed with 2 volumes of ethanol and the precipitate is then washed with 70% ethanol. The pellet is taken up in 0.5 ml of TE buffer (10 mM Tris-HCl, 1 mM EDTA pH 7.5), the mixture is extracted twice with chloroform and the product is precipitated with ethanol. The RNA is stored at −80° C. in ethanol.

2) Purification of the poly(A)$^+$ fraction of the RNA

Approximately 1 mg of RNA is precipitated for 20 min at 4° C. (15,000 rpm), then washed with 70% ethanol and then dried. The pellet is taken up in 1 ml of TE buffer and suspended by vortexing. Type 3 oligo(dT)-cellulose (marketed by Collaborative Research Inc, Biomedicals Product Division) is prepared according to the manufacturer's recommendations. The RNA is applied to the oligo(dT), agitated gently to resuspend the beads and then heated for 1 min to 65° C.

The suspension is adjusted to 0.5 M NaCl and then agitated gently for 10 min. The suspension is then centrifuged for 1 min at 1,000 rpm, the supernatant is removed and the pellet is washed twice with 1 ml of TE buffer containing 0.5M NaCl. The supernatants are removed. Elution of the polyadenylated fraction of the RNA (consisting of messenger RNAs) is obtained by suspending the beads in 1 ml of TE buffer and then heating this suspension to 60° C. for 1 min, followed by agitation for 10 min on a rocking-stage mixer. The mixture is then centrifuged for 1 min at 1,000 rpm, permitting recovery, on the one hand of the supernatant containing free mRNAs in solution, and on the other hand of the pellet of cellulose beads. All the above operations (beginning with elution) are repeated. The supernatants thereby obtained are combined, the excess beads are removed by centrifugation and the supernatant is precipitated with ethanol containing NaCl according to the usual techniques (Maniatis: op. cit.).

3) Description of the polymerase chain reaction (PCR) technique

The polymerase chain reaction (PCR) technique is a method, well known to those skilled in the art, which enables both strands of a previously denatured DNA sequence to be copied simultaneously using two oligonucleotides as primers (see, in particular, the work by H.A. Erlich: "PCR Technology: Principles and Applications for DNA amplification" published in 1989 by Macmillan Publishers Ltd publications, United Kingdom, and that of M. A. INNIS et al. "PCR Protocols" published in 1990 by Academic Press Inc. San Diego, Calif. 92101, USA). The principle of this technique is summarised below.

A large number of cycles, each of which consists of three steps, produce amplification of the DNA strands of interest; these three steps are:

a) denaturation of the template b) hybridisation of the primers with the template c) extension of the primers.

After a few hours of cycles, hundreds of thousands of copies of the original template have been produced using a heat-stable DNA polymerase of *Thermus acuaticus*, commonly referred to as Taq polymerase.

The PCR technique is based on the repetition of three steps.

a) Denaturation of the template

The double-stranded DNA is denatured to single-stranded DNA by incubation at high temperature (from 92° C. to 96° C.) for approximately 2 min.

b) Hybridisation of the primers

These primers are a pair of synthetic oligonucleotides which hybridise with the ends of the region to be amplified. The two primers hybridise with the opposite strands. The primers are added in excess so that formation of the primer-template complex is favoured.

c) Extension of the primers

The step during which Taq polymerase effects extension of the primer-template complex from 5' to 3' is performed at 72° C.

In the PCR technique, the product of interest appears in the third cycle and it is then amplified significantly. As the cycles proceed, the amplification product rapidly becomes the major template with which the primers hybridise.

4) Description of the primers used

Two synthetic oligonucleotides were prepared from the sequence of the fragment A (see FIG. 2).

The first oligonucleotide, referred to as primer 1 and whose sequence is as follows (SEQ ID NO:22):

possesses two distinct regions: region 1, which carries a cloning site AAGCTT corresponding to the recognition site of the endonuclease HindIII, and region 2, which is a region intended for hybridisation with the non-coding region of the coding strand of the fragment A, located on the 3' side of the sequence coding for preproendothiapepsin (see FIG. 2—position 1870–1881).

The second oligonucleotide, referred to as primer 2 and whose sequence is as follows (SEQ ID NO:23):

also consists of two distinct regions: region 1, which carries a cloning site CATATG corresponding to the recognition site of the endonuclease NdeI and in which is included the sequence of the initiation codon ATG, and region 2, which carries a nucleotide sequence identical to that coding for the first five amino acids of preproendothiapepsin which follow the initial methionine. This region is intended for hybridisation with the non-coding strand of the fragment A.

5) Production of the amplified fragment representing the complementary DNA of endothiapepsin A pool of messenger RNA known to contain the messenger RNA coding for endothiapepsin is used as a template; an enzymatic reaction using reverse transcriptase is performed on the messenger RNA before amplification.

a) Demonstration of the presence of the messenger RNA coding for endothiapepsin in the total RNA preparation.

α) Northern blotting

The Northern technique is used (Maniatis). It consists essentially in separating approximately 10 μg of total RNA by electrophoresis on 1.0% agarose gel under denaturing conditions (20 mM MOPS pH 7, 5 mM sodium acetate, 1 mM EDTA, 6.6% formaldehyde). The RNA thus separated is transferred onto a nitrocellulose sheet (Maniatis op. cit.). Two different nitrocellulose filters are thereby prepared, one of which is hybridised with radiolabelled probe 1 and the other with radiolabelled probe 2 [see Section 1.2) and 1.3) for the preparation of the probes and their labelling with $^{32}$P].

β) Hybridisation with radiolabelled probe 1 and radiolabelled probe 2

The hybridisation conditions are the same as those described in Section 1.5). After hybridisation, each of the filters is washed individually in a solution containing 0.5× SSC at 42° C. The filters are then exposed to a photographic film (Kodak XAR5) overnight.

Analysis of the films shows that an RNA population responds specifically to both probes, thereby indicating that the messenger RNA coding for endothiapepsin is present in the preparation.

b) The reaction using reverse transcriptase

The reaction of reverse transcriptase with 1 μg of messenger RNA is performed in the presence of 10 mM dithiothreitol DTT, RNasin (RNase inhibitor, Genofit) 0.0040 U/μl, a mixture of the four deoxyribonucleotide triphosphates dNTP at a concentration of 10 mM, buffer of composition 50 mM Tris-HCl pH 8.3, 20 mM KCl and 10 mM MgCl$_2$, 0.7 unit of reverse transcriptase (Stratagene) and 0.1 ng of primer 1 as well as 0.1 ng of primer 2 for a final volume of 10 μl. After incubation for half an hour at 46° C., the reaction is stopped by adding 20 mM EDTA and the mixture is then incubated for 5 min at 65° C.

c) The PCR reaction

The mixture described above is subjected to chromatography on a P10 polyacrylamide gel column in order to remove the small molecules (nucleotides, EDTA, and the like). The solution then obtained is incubated for 2 min at 92° C. in order to denature the template composed of a strand of complementary DNA and a strand of messenger RNA. 100 ng of primer 1, 100 ng of primer 2, 2 mM MgCl$_2$, 0.2 mM dNTP and 5 μl of reaction mixture concentrated 10-fold (final quantity: 67 mM Tris-HCl pH 8.8, 16.6 mM (NH$_4$)$_2$SO$_4$, 1 mM β-mercaptoethanol, 6.7 mM EDTA, 0.15% Triton X-100, 200 g/ml of gelatin) are then added to the tube.

The volume of the mixture is then brought to 50 μl by adding water.

The reaction mixture thereby obtained is incubated for 4 min at 94° C. and then taken to a temperature of 41° C., which is maintained for 4 min. The temperature of 41° C. corresponds to a value 5 degrees lower than the temperature of half-denaturation of the oligonucleotide, calculated with an empirical formula well known to those skilled in the art.

0.5 μl, equivalent to 2.5 units, of Taq polymerase (Boehringer Mannheim ref. 1146-165) is then added. The reaction mixture is then covered with paraffin in order to prevent evaporation of the aqueous solution.

The amplification is carried out during 30 reaction cycles, the steps of one cycle being as follows:

2 min at 92° C.→denaturation 2 min at 41° C.→hybridisation 2 min at 72° C.→polymerisation.

After the 30 cycles, the enzymatic reaction is stopped by adding 20 mM EDTA.

The DNA fragment thus amplified, which possesses the expected size of approximately 1,300 bp, is then isolated and purified on 1% agarose gel, dialysed on a P10 column and then hydrolysed simultaneously with the enzymes NdeI and HindIII according to the usual techniques well known to those skilled in the art (Maniatis, op. cit.) in order to form the NdeI and HindIII cohesive ends. After hydrolysis, the fragment is purified on a P10 column.

Section 16

Construction of plasmid p572, a vector for the cloning and expression in *E. coli* of the complementary DNA coding for the endothiapepsin precursor. Determination of the sequence of this complementary DNA and expression of the latter.

1) Construction of plasmid p572

Plasmid p572 was prepared from plasmid p466, a vector for the cloning and expression of the complementary DNA of urate oxidase of *Aspergillus flavus* in *E. coli*, described in Patent Application PCT-FR-90/00,532, which comprises a fragment of plasmid pBR327 including the origin of replication and the ampicillin resistance gene, a synthetic promoter of *E. coli* (R. RODRIGUEZ and M. CHAMBERLIN "Promoters-Structure and function" (1982) Preager), a Shine-Dalgarno sequence followed by a polylinker possessing single NdeI and HindIII sites, a transcription terminator (derived from phage fd) and the lac i gene.

a) Construction of plasmid p466

Plasmid p466, an expression vector in *E. coli*, was prepared. It comprises a fragment of pBR327 including the origin of replication and the ampicillin resistance gene; it also comprises a synthetic promoter of *E. coli* (R. RODRIGUEZ and M. CHAMBERLIN "Promoters-Structure and function" (1982) Preager), a Shine-Dalgarno sequence followed by a polylinker possessing single NdeI and KpnI sites, a transcription terminator (derived from phage fd) and the lac i gene.

This plasmid was constructed from a plasmid for the expression of hGH in *E. coli* (p462) by substitution of a fragment carrying the hGH gene by the cDNA of urate oxidase.

The construction of plasmid p466 will now be described in greater detail in the account below, in which reference will be made to FIGS. 6, 7, 8, 9 and 10.

1) Construction of plasmid p373,2

The strategy employed makes use of fragments obtained from pre-existing plasmids available to the public and fragments prepared synthetically according to techniques now in common use. The cloning techniques employed are those described by T. MANIATIS, E. F. FRITSCH and J. SAMBROOK, Cold Spring Harbor Laboratory (1982). Oligonucleotide synthesis is carried out using a Biosearch 4600 DNA synthesiser.

Plasmid p163,1 (FIG. 6), described in Patent Application EP-A-0,245,138 and deposited with the CNCM under reference I-530 on 17th Feb. 1986, was subjected to a digestion with the enzymes PvuI and BamhI. This plasmid contains the gene coding for hGH. The PvuI-BamHI fragment—hereinafter fragment 1—containing the site of action of the restriction enzyme XhoI, shown in FIG. 6, was purified.

Similarly, plasmid pBR327, well known to those skilled in the art (see SOBERON, X et al., Gene, 9 (1980) 287–305), was subjected to a digestion with the enzymes PvuI and BamHI. The PvuI-BamHI fragment—herein-after fragment 2—containing the origin of replication was purified.

The fragment 3, which is a synthetic BamHI(1)–BamHI (2) fragment containing the lac i gene and its promoter and whose sequence is as follows (SEQ ID NO:24), on which sequence the two ends of the strand are identified by the numbers 1 and 2 in order to specify the orientation of the fragment in the plasmids described in FIGS. 7 and 8, was then prepared.

---

FRAGMENT 3 (SEQ ID NO: 24)

```
BamHI(1)
5'        GATCC GCGGAAGCAT AAAGTGTAAA GCCTGGGGTG CCTAATGAGT

GAGCTAACTT ACATTAATTG CGTTGCGCTC ACTGCCCGCT TTCCAGTCGG

GAAACCTGTC GTGCCAGCTG CATTAATGAA TCGGCCAACG CGCGGGGAGA

GGCGGTTTGC GTATTGGGCG CCAGGGTGGT TTTTCTTTTC ACCAGTGAGA

CGGGCAACAG CTGATTGCCC TTCACCGCCT GGCCCTGAGA GAGTTGCAGC

AAGCGGTCCA CGCTGGTTTG CCCCACCACC CGAAAATCCT GTTTGATGGT

GGTTAACGGC GGGATATAAC ATGAGCTGTC TTCGGTATCG TCGTATCCCA

CTACCGAGAT ATCCGCACCA ACGCGCAGCC CGGACTCGGT AATGGCGCGC

ATTGCGCCCA GCGCCATCTG ATCGTTGGCA ACCAGCATCG CAGTGGGAAC

GATGCCCTCA TTCAGCATTT GCATGGTTTG TTGAAAACCG GACATGGCAC

TCCAGTCGCC TTCCCGTTCC GCTATCGGCT GAATTTGATT GCGAGTGAGA

TATTTATGCC AGCCAGCCAG ACGCAGACGC GCCGAGACAG AACTTAATGG

GCCCGCTAAC AGCGCGATTT GCTGGTGACC CAATGCGACC AGATGCTCCA

CGCCCAGTCG CGTACCGTCT TCATGGGAGA AAATAATACT GTTGATGGGT

GTCTGGTCAG AGACATCAAG AAATAACGCC GGAACATTAG TGCAGGCAGC

TTCCACAGCA ATGGCATCCT GGTCATCCAG CGGATAGTTA ATGATCAGCC

CACTGACGCG TTGCGCGAGA AGATTGTGCA CCGCCGCTTT ACAGGCTTCG

ACGCCGCTTC GTTCTACCAT CGACACCACC ACGCTGGCAC CCAGTTGATC

GGCGCGAGAT TTAATCGCCG CGACAATTTG CGACGGCGCG TGCAGGGCCA

GACTGGAGGT GGCAACGCCA ATCAGCAACG ACTGTTTGCC CGCCAGTTGT
```

-continued

FRAGMENT 3 (SEQ ID NO: 24)

```
     TGTGCCACGC GGTTGGGAAT GTAATTCAGC TCCGCCATCG CCGCTTCCAC

TTTTTCCCGC GTTTTCGCAG AAACGTGGCT GGCCTGGTTC ACCACGCGGG

AAACGGTCTG ATAACAGACA CCGGCATACT CTGCGACATC GTATAACGTT

ACTGGTTTCA CATTCACCAC CCTGAATTGA CTCTCTTCCG GGCGCTATCA

TGCCATACCG CGAAAGGTTT TGCGCCATTC GATGGTGTCC G           3'

BamHI(2)
```

The fragments 1, 2 and 3 were then ligated so as to obtain plasmid p160, shown in FIG. 7.

This plasmid was subjected to a partial digestion with the restriction enzymes HincII and PstI. The large HincII-PstI fragment, containing the origin of replication and shown in FIG. 7, was then ligated to the fragment 4 (SEQ ID NO:25), shown below, which is a synthetic DNA fragment carrying a sequence coding for the first 44 amino acids of a natural precursor of hGH and, upstream of this sequence, regulation signals (SEQ ID NO:26).

| A = Alanine | M = Methionine |
|---|---|
| C = Cysteine | N = Asparagine |
| D = Aspartic acid | P = Proline |
| E = Glutamic acid | Q = Glutamine |
| F = Phenylalanine | R = Arginine |
| G = Glycine | S = Serine |
| H = Histidine | T = Threonine |
| I = Isoleucine | V = Valine |
| K = Lysine | W = Tryptophan |
| L = Leucine | Y = Tyrosine |

FRAGMENT 4 (SEQ ID NO: 25)

```
                                                  ClaI
                                                   ▼
              5'       TCGAGCTGACTGACCTGTTGCTTATATTACATCGA
                       ----------------------------------
                       AGCTCGACTGACTGGACAACGAATATAATGTAGCT
                                                        ▲
                                                      NdeI
                                                       ▼
TAGCGTATAATGTGTGGAATTGTGAGCGATAACAATTTCACACAGTTTAACTTTAAGAAGGAGATATACAT
----------------------------------------------------------------------
ATCGATATTACACACCTTAACACTCGCCTATTGTTAAAGTGTGTCAAATTGAAATTCTTCCTCTATATGTA

ATG GCT ACC GGA TCC CGG ACT AGT CTG CTC CTG GCT TTT GGC CTG CTC TGC CTG
----------------------------------------------------------------------
TAC CGA TGG CCT AGG GCC TGA TCA GAC GAG GAC CGA AAA CCG GAC GAC ACG GAC
▲
 M   A   T   G   S   R   T   S   L   L   L   A   F   G   L   L   C   L
-26

XbaI
                                                      ▼
CCC TGG CTT CAA GAG GGC AGT GCC TTC CCA ACC ATT CCC TTA TCT AGA CTT TTT
-----------------------------------------------------
GGG ACC GAA GTT CTC CCG TCA CGG AAG GGT TGG TAA GGG AAT AGA TCT GAA AAA
                                                              ▲
 P   W   L   Q   E   G   S   A   F   P   T   I   P   L   S   R   L   F
                                -1  1

GAC AAC GCT ATG CTC CGC GCC CAT CGT CTG CAC CAG CTG GCC TTT GAC ACC TAC
----------------------------------------------------------------------
CTG TTG CGA TAC GAG GCG CGG GTA GCA GAC GTG GTC GAC CGG AAA CTG TGG ATG
 D   N   A   M   L   R   A   H   R   L   H   Q   L   A   F   L   T   Y
                                                                  PstI
CAG GAG TTT GAA GAA GCC TAT ATC CCA AAG GAA CAG AAG TAT TCA TTC CTG CA
----------------------------------------------------------------------
GTC CTC AAA CTT CTT CGG ATA TAG GGT TTC CTT GTC TTC ATA AGT AAG G
 Q   E   F   E   E   A   Y   I   P   K   E   Q   K   Y   S   F
                                                                44
```

In this fragment, the amino acids are designated by letters according to the following code:

In this fragment, the sequences −35 (TTGCTT) and −10 (TATAAT) of the promoter sequence and the Shine- Dalgarno sequence which is well known to those skilled in the art are successively underlined.

Plasmid p380,1 was thereby obtained.

Plasmid p380,1 was then subjected to a digestion with the restriction enzymes ClaI and NdeI so as to remove from it the small ClaI–NdeI fragment of the above fragment 4 and to substitute for it the ClaI–NdeI fragment below (SEQ ID NO:27):

```
    ClaI
5'  CGATAGCGTATAATGTGTGGAATTGTGAGCGGATAACA
    TATCGCATATTACACACCTTAACACTCGCCTATTGT

NdeI
    ATTTCACACAGTTTTTCGCGAAGAAGGAGATATACA
    TAAAGTGTGTCAAAAAGCGCTTCTTCCTCTATATGTAT    5'
```

2) Construction of plasmid p466

Plasmid p373,2 was subjected to a double digestion with the enzymes BglII and HindIII. The large fragment derived from this digestion was purified and ligated with a synthetic DNA fragment whose sequence (SEQ ID NO:28), given below, is intended for re-forming the end of the hGH gene followed at the 3' end by KpnI and SnaBI cloning sites.

Moreover, the cDNA of urate oxidase contains an AccI site situated in proximity to the 5' end.

The AccI-KpnI fragment comprising the larger part of this cDNA was hence isolated and purified. Moreover, two complementary oligonucleotides, whose sequence (SEQ ID NOS:29 and 30), given below:

```
5'-TATGTCTGCGGTAAAAGCAGCGCGCTACGGCAAGGACAATGTTCGCGT
   ACAGACGCCATTTTCGTCGCGCGATGCCGTTCCTGTTACAAGCGCAGA-5'
``` is intended for re-forming the 5' end of the cDNA, were synthesised. This synthetic fragment thereby obtained possesses an NdeI end and an AccII end. The fragment and the synthetic sequence were ligated with the expression vector cut with KpnI and with NdeI. This three-fragment ligation enables the vector, designated p466, for the expression of urate oxidase for *E. coli* to be obtained (see FIG. 10). This plasmid was subjected to a series of enzymatic hydrolyses with restriction enzymes, which enabled the presence of the expected restriction sites to be verified, especially those carried by the gene coding for urate oxidase.

Plasmid p466 hence contains by construction a gene coding for urate oxidase, of the sequence below (SEQ ID NO:31):

```
         B
         g
         l
         I
         I
         GATCTTCAAGCAGACCTACAGCAAGTTCGACACAAACTCACACAACGAT
         ----+---------+---------+----------+---------+
         AAGTTCGTCTGGATGTCGTTCAAGCTGTGTTTGAGTGTGTTGCTA
GACGCACTACTCAAGAACTACGGGCTGCTCTACTGCTTCAGGAAGGACATGGACAAGGTC
---------+---------+---------+---------+---------+---------+
CTGCGTGATGAGTTCTTGATGCCCGACGAGATGACGAAGTCCTTCCTGTACCTGTTCCAG
                 F
                 s
                 p
                 I
GAGACATTCCTGCGCATCGTGCAGTGCCGCTCTGTGGAGGGCAGCTGTGGCTTCTAGTAA
---------+---------+---------+---------+---------+---------+
CTCTGTAAGGACGCGTAGCACGTCACGGCGAGACACCTCCCGTCGACACCGAAGATCATT
                 H
                 i
             S   n
    K        n   d
    p        a   I
    n        B   I
    I        I   I
GGTACCCTGCCCTACGTACCA
---------+---------+-----
CCATGGGACGGGATGCATGGTTCGA
```

This fragment comprises the BglII and HindIII cohesive ends. The new plasmid thereby formed, p462 (see FIG. 9), thus comprises a KpnI site and an NdeI site which will be used for cloning the fragment carrying the cDNA of urate oxidase into the expression vector.

The hybrid plasmid derived from pTZ19R carrying the approximately 1.2-kb cDNA (clone 9C) of urate oxidase comprises a single KpnI site. This site is localised a few base pairs downstream of the cloning site of the cDNA.

```
ATGTCTGCGG TAAAAGCAGC GCGCTACGGC AAGGACAATG TTCGCGTCTA

CAAGGTTCAC AAGGACGAGA AGACCGGTGT CCAGACGGTG TACGAGATGA

CCGTCTGTGT GCTTCTGGAG GGTGAGATTG AGACCTCTTA CACCAAGGCC

GACAACAGCG TCATTGTCGC AACCGACTCC ATTAAGAACA CCATTTACAT

CACCGCCAAG CAGAACCCCG TTACTCCTCC CGAGCTGTTC GGCTCCATCC

TGGGCACACA CTTCATTGAG AAGTACAACC ACATCCATGC CGCTCACGTC

AACATTGTCT GCCACCGCTG GACCCGGATG GACATTGACG GCAAGCCACA

CCCTCACTCC TTCATCCGCG ACAGCGAGGA GAAGCGGAAT GTGCAGGTGG

ACGTGGTCGA GGGCAAGGGC ATCGATATCA AGTCGTCTCT GTCCGGCCTG

ACCGTGCTGA AGAGCACCAA CTCGCAGTTC TGGGGCTTCC TGCGTGACGA

GTACACCACA CTTAAGGAGA CCTGGGACCG TATCCTGAGC ACCGACGTCG

ATGCCACTTG GCAGTGGAAG AATTTCAGTG GACTCCAGGA GGTCCGCTCG

CACGTGCCTA AGTTCGATGC TACCTGGGCC ACTGCTCGCG AGGTCACTCT

GAAGACTTTT GCTGAAGATA ACAGTGCCAG CGTGCAGGCC ACTATGTACA

AGATGGCAGA GCAAATCCTG GCGCGCCAGC AGCTGATCGA GACTGTCGAG

TACTCGTTGC CTAACAAGCA CTATTTCGAA ATCGACCTGA GCTGGCACAA

GGGCCTCCAA AACACCGGCA AGAACGCCGA GGTCTTCGCT CCTCAGTCGG

ACCCCAACGG TCTGATCAAG TGTACCGTCG GCCGGTCCTC TCTGAAGTCT

AAATTG.
```

(The nucleotides different from the nucleotides of the cDNA isolated from *A. flavus* are underlined in the above sequence. These differences were introduced into the synthetic AccI-KpnI fragment so as to have, downstream of the ATG, a nucleotide sequence conforming more closely to those usually encountered in a prokaryotic gene).

Plasmid p466 was hydrolysed with the enzymes NdeI and HindIII, and the fragment carrying the lac i gene, the origin of replication and the gene coding for ampicillin resistance was purified according to the techniques known to those skilled in the art (Maniatis, op. cit.).

This fragment was ligated to the amplified complementary DNA fragment previously hydrolysed with the endonucleases NdeI and HindIII. The product of this ligation was used for transformation in *E. coli* strain K12 RRI. (Gibco BRL-ref.: 520-8261 SA). A transformant, referred to as clone 512, which contains the plasmid referred to as p572, was adopted.

2) Determination of the sequence of the complementary DNA

Plasmid p572 was hydrolysed, on the one hand with the endonucleases ClaI and KpnI, and on the other hand with the enzymes KpnI and HindIII. (The endonuclease KpnI cuts the coding sequence of the fragment A). The ClaI-KpnI fragment carrying the 5' end of the DNA coding for the protein and the KpnI-HindIII fragment carrying the 3' end of the DNA coding for the protein were cloned into phage M13mp19 (Pharmacia) and sequenced by the cyclone technique ("Cyclone I Biosystem" of IBI).

The nucleotide sequence of the complementary DNA thereby obtained is shown in FIG. 11. It is observed that the coding sequence of the complementary DNA is exactly identical to that of the genomic DNA, the only difference being that the latter is interrupted by three introns, which have been correctly localised (see Section 1.7)).

3) Expression of the complementary DNA of preproendothiapepsin

*E. coli* strain K12 RRI (Gibco BRL Ref.: 520-8261A) was transformed for ampicillin resistance with plasmid p572 carrying the complementary DNA of preproendothiapepsin, whose sequence was determined in 2), and with a negative control plasmid pBR322.

Ampicillin-resistant colonies were obtained in both cases.

1 colony of each type was cultured in LB liquid medium (of composition specified in Table 4, but without agar) supplemented with 100 μg/ml of ampicillin. After stirring overnight at 37° C., both cultures were diluted 100-fold in liquid LB medium supplemented with 100 μg/ml of ampicillin. After 1 h of culture, IPTG (isopropyl-β-D-thiogalactoside) was added to a concentration of 1 mM for 3 h.

Immunodetection of preproendothiapepsin by Western blotting a) Procedure

An aliquot fraction corresponding to 0.2 ml with an OD=1 is withdrawn from the culture medium obtained after 3 h of induction with IPTG. The aliquot is centrifuged and the supernatant is removed. The pellet is then subjected to Western blotting, a technique well known to those skilled in the art, which comprises the following steps:

Solubilisation of the pellet by boiling for 10 min in a buffer, designated loading buffer, consisting of 0.125M Tris-HCl pH 6.8, 4% SDS, 0.002% bromophenol blue, 20% glycerol and 10% β-mercaptoethanol (according to the protocol described by LAEMMLI (U. K. LAEMMLI, Nature, 227 (1970), 680–685)), Electrophoretic separation of the different proteins contained in the solubilisate according to the protocol described by LAEMMLI (U. K. LAEMMLI, Nature, 227, (1970), 680–685), Transfer of the said proteins contained in the gel onto a nitrocellulose filter (according to the technique of H. TOWBIN et al. Proc. Natl. Acad. Sci. USA 76 (1979) 4350–4354), Immunodetection, carried out according to the technique of BURNETTE (W. W. BURNETTE Ana. Biochem. 112 (1981) 195–203); this involves successively:

Rinsing the nitrocellulose filter for 10 min with a buffer of composition 10 mM Tris-HCl, 170 mM NaCl, 1 mM KCl.

Bringing the nitrocellulose filter into contact for 30 min at 37° C. with buffer A supplemented with bovine serum albumin in the proportion of 3 g per 100 ml.

Bringing the nitrocellulose filter into contact for 1 h at 37° C. with the polyclonal antibodies of the Rennetest France Biochem kit, according to the method of identification of endothiapepsin described in the Journal Officiel de la République Française (Official Journal of the French Republic) of Mar. 20, 1981.

Rinsing the nitrocellulose filter with buffer A supplemented with 3 g/100 ml of bovine serum albumin.

Bringing the nitrocellulose filter into contact for 1 h at 37° C. with a solution of iodine-125-labelled protein G having an activity of 0.1 microcurie/ml.

Rinsing the filter with buffer A.

Drying the filter between two absorbent sheets.

Bringing the filter into contact with a radiographic film.

Developing the film.

b) Results

It is found that the strain transformed with plasmid p572 overproduces a protein of apparent molecular weight approximately 43 kDa corresponding to the expected molecular mass of preproendothiapepsin, which is recognised by antibodies directed towards endothiapepsin and which is absent in the control strain.

We claim:

1. An endothiapepsin-producing *Cryphonectria parasitica* strain, wherein said strain is transformed with a cassette for the expression of an endothiapepsin precursor of *Cryphonectria parasitica*, said cassette comprising a functional promoter upstream of a nucleic acid sequence coding for said precursor, wherein endothiapepsin has the following amino acid sequence (PI) (SEQ ID NO:1), wherein said precursor is preproendothiapepsin comprising the following amino acid sequence (P4) (SEQ ID NO:2):

```
Met Ser Ser Pro Leu Lys Asn Ala Leu Val Thr Ala Met
                                        Leu Ala Gly

Gly Ala Leu Ser Ser Pro Thr Lys Gln His Val Gly Ile
                                        Pro Val Asn

Ala Ser Pro Glu Val Gly Pro Gly Lys Tyr Ser Phe Lys
                                        Gln Val Arg

Asn Pro Asn Tyr Lys Phe Asn Gly Pro Leu Ser Val Lys
                                        Lys Thr Tyr
```

Leu Lys Tyr Gly Val Pro Ile Pro Ala Trp Leu Glu Asp Ala Val Gln

Asn Ser Thr Ser Gly Ler Ala Glu Arg Ser Thr Gly Ser Ala Thr Thr

Thr Pro Ile Asp Ser Leu Asp Asp Ala Tyr Ile Thr Pro Val Gln Ile

Gly Thr Pro Ala Gln Thr Leu Asn Leu Asp Phe Asp Thr Gly Ser Ser

Asp Leu Trp Val Phe Ser Ser Glu Thr Thr Ala Ser Glu Val Asp Gly

Gln Thr Ile Tyr Thr Pro Ser Lys Ser Thr Thr Ala Lys Leu Leu Ser

Gly Ala Thr Trp Ser Ile Ser Tyr Gly Asp Gly Ser Ser Ser Ser Gly

Asp Val Tyr Thr Asp Thr Val Ser Val Gly Gly Leu Thr Val Thr Gly

Gln Ala Val Glu Ser Ala Lys Lys Val Ser Ser Ser Phe Thr Glu Asp

Ser Thr Ile Asp Gly Leu Leu Gly Leu Ala Phe Ser Thr Leu Asn Thr

Val Ser Pro Thr Gln Gln Lys Thr Phe Phe Asp Asn Ala Lys Ala Ser

Leu Asp Ser Pro Val Phe Thr Ala Asp Leu Gly Tyr His Ala Pro Gly

Thr Tyr Asn Phe Gly Phe Ile Asp Thr Thr Ala Tyr Thr Gly Ser Ile

Thr Tyr Thr Ala Val Ser Thr Lys Gln Gly Phe Trp Glu Trp Thr Ser

Thr Gly Tyr Ala Val Gly Ser Gly Thr Phe Lys Ser Thr Ser Ile Asp

Gly Ile Ala Asp Thr Gly Thr Thr Leu Leu Tyr Leu Pro Ala Thr Val

Val Ser Ala Tyr Trp Ala Gln Val Ser Gly Ala Lys Ser Ser Ser Ser

Val Gly Gly Tyr Val Phe Pro Cys Ser Ala Thr Leu Pro Ser Phe Thr

Phe Gly Val Gly Ser Ala Arg Ile Val Ile Pro Gly Asp Tyr Ile Asp

Phe Gly Pro Ile Ser Thr Gly Ser Ser Ser Cys Phe Gly Gly Ile Gln

Ser Ser Ala Gly Ile Gly Ile Asn Ile Phe Gly Asp Val Ala Leu Lys

Ala Ala Phe Val Val Phe Asn Gly Ala Thr Thr Pro Thr Leu Gly Phe

Ala Ser Lys

2. The strain of claim 1, wherein the nucleic acid sequence encoding said preproendothiapepsin comprises the following nucleic acid sequence (N4a) (SEQ ID NO:3):

```
ATGTCTTCCC CTCTCAAGAA CGCCTTGGTG ACCGCCATGT TGGCTGGTGG TGCTCTCAGC
TCGCCTACAA AGCAACACGT TGGAATTCCC GTCAACGCCT CTCCTGAAGT TGGCCCCGGA
AAGTACTCGT TCAAGCAAGT CCGGAACCCC AACTACAAGT TCAACGGGCC TCTGTCGGTC
AAGAAGACGT ACCTCAAGTA CGGCGTGCCG ATCCCAGCCT GGCTGGAGGA TGCTGTCCAG
AACTCTACCT CGGGCCTGGC TGAGCGCTCG ACCGGTTCTG CGACCACAAC TCCCATCGAC
AGCCTCGATG ATGCTTACAT CACTCCGGTT CAGATCGGCA CCCCTGCGCA GACTCTGAAC
CTGGACTTTG ACACTGGATC TTCGGATCTG TGGGTCTTCA GCAGCGAGAC TACAGCCAGC
GAGGTCGATG GCAGACCAT CTACACCCCC AGCAAGAGCA CCACCGCCAA GCTGCTGTCG
GCGCTACCTG GTCCATCTCC TACGGAGACG GTAGCTCTTC CAGCGGCGAT GTCTACACTG
ACACCGTCTC GGTTGGAGGC CTTACCGTGA CGGGCCAGGC TGTCGAGTCG GCCAAGAAGG
TTTCTTCCAG CTTCACCGAG GACTCGACCA TTGACGGTCT CCTGGGCCTG GCCTTCAGCA
CCCTGAACAC TGTGTCGCCT ACCCAGCAAA AGACTTTCTT CGACAATGCG AAGGCGTCCT
TGGACTCGCC TGTGTTCACG GCTGATCTTG GCTACCATGC CCCTGGTACC TACAACTTCG
GCTTCATCGA TACCACTGCC TACACGGGCT CCATCACCTA CACCGCTGTC TCGACCAAGC
AAGGGTTCTG GGAGTGGACT TCGACCGGCT ACGCCGTCGG CTCCGGCACC TTCAAGTCGA
CTTCCATCGA CGGCATCGCT GACACTGGCA CGACCCTCCT GTACCTCCCT GCCACCGTCG
TGTCGGCCTA CTGGGCCCAG GTCTCGGGCG CCAAGTCCAG CTCTTCCGTC GGCGGCTACG
TCTTCCCCTG CAGCGCGACC CTGCCTTCCT TCACCTTCGG CGTTGGCTCA GCTCGCATTG
TGATTCCTGG CGACTACATT GATTTCGGCC CCATCTCCAC TGGAAGCTCG TCTTGCTTTG
GCGGCATCCA GTCCAGCGCT GGTATCGGCA TCAACATCTT CGGTGATGTC GCTCTGAAGG
CTTTGTCGTC TTCAACGGGG CTACAACTCC CACTCTTGGC TTTGCTTCCA AG
```

3. The strain of claim 11, wherein said promoter is derived from a filamentous fungus of the class Ascomycetes.

4. The strain of claim 1, wherein said strain is devoid of a dominant selection marker.

5. The transformed strain of claim 1, wherein the untransformed *Cryphonectria parasitica* is the strain SEBR103, deposited with CNCM on Aug. 31, 1990, under no° I-997.

6. The strain of claim 2, wherein the nucleic acid sequence N4a (SEQ ID NO:3) is interrupted by at least one intron.

7. The strain of claim 6, wherein the nucleic acid sequence encoding said preproendothiapepsin comprises the following nucleic acid sequence (N4b) (SEQ ID NO:4):

9. The strain of claim 3, wherein said promoter is the glyceraldehyde-3-phosphate dehydrogenase promoter of *Aspergillus nidulans.*

10. The strain of claim 8, wherein said promoter is the preproendothiapepsin *Cryphonectria parasitica* promoter.

11. The strain of claim 10, wherein the functional portion of said promoter is the 5'-Bgl II to Sca I segment of fragment C of FIG. 4.

12. The strain of claim 10, wherein the functional portion of said promoter is the 5'-Bam HI to Sca I segment of fragment C of FIG. 4.

13. The strain of claim 10, wherein said promoter comprises a sequence of the following nucleic acid sequence (N5) (SEQ ID NO:5):

```
ATGTCTTCCC CTCTCAAGAA CGCCTTGGTG ACCGCCATGT TGGCTGGTGG TGCTCTCAGC
TCGCCTACAA AGCAACACGT TGGAATTCCC GTCAACGCCT CTCCTGAAGT TGGCCCCGGA
AAGTACTCGT TCAAGCAAGG TGAGTAGAGC TGCTTCTGTG TGTTGCAACA GAAGACCAAC
GCAAAAAGAA GAGGTCAAGG CAAGACGGAT ATTTTACTGA CAATTATACT TTTGAAGTCC
GGAACCCCAA CTACAAGTTC AACGGGCCTC TGTCGGTCAA GAAGACGTAC CTCAAGTACG
GCGTGCCGAT CCCAGCCTGG CTGGAGGATG CTGTCCAGAA CTCTACCTCG GGCCTGGCTG
AGCGCTCGAC CGGTTCTGCG ACCACAACTC CCATCGACAG CCTCGATGAT GCTTACATCA
CTCCGGTTCA GATCGGCACC CCTGCGCAGA CTCTGAACCT GGACTTTGAC ACTGGATCTT
CGGATCTGTG GGTCTTCAGC AGCGAGACTA CAGCCAGCGA GGTTGGTCAA CCCTCGCCCG
CATTTTATTG CATACATTTT TAGTTTTTTT GGTAATCAGA ATACTAACAT TGGGAATTTC
CCAACTGTAG GTCGATGGGC AGACCATCTA CACCCCCAGC AAGAGCACCA CCGCCAAGCT
GCTGTCGGGC GCTACCTGGT CCATCTCCTA CGGAGACGGT AGCTCTTCCA GCGGCGATGT
CTACACTGAC ACCGTCTCGG TTGGAGGCCT TACCGTGACG GGCCAGGCTG TCGAGTCGGC
CAAGAAGGTT TCTTCCAGCT TCACCGAGGA CTCGACCATT GACGGTCTCC TGGGCCTGGC
CTTCAGCACC CTGAACACTG TGTCGCCTAC CCAGCAAAAG ACTTTCTTCG ACAATGCGAA
GGCGTCCTTG GACTCGCCTG TGTTCACGGC TGATCTTGGC TACCATGCCC GTGAGTGACC
CCTCTTGATA CATATACTTT TTGATGAATC TTGTTGGAGA AGCATTCCCC ACTAATATGG
AAATTGTTTG TATCTACAGC TGGTACCTAC AACTTCGGCT TCATCGATAC CACTGCCTAC
ACGGGCTCCA TCACCTACAC CGCTGTCTCG ACCAAGCAAG GGTTCTGGGA GTGGACTTCG
ACCGGCTACG CCGTCGGCTC CGGCACCTTC AAGTCGACTT CCATCGACGG CATCGCTGAC
ACTGGCACGA CCCTCCTGTA CCTCCCTGCC ACCGTCGTGT CGGCCTACTG GGCCCAGGTC
TCGGGCGCCA AGTCCAGCTC TTCCGTCGGC GGCTACGTCT TCCCCTGCAG CGCGACCCTG
CCTTCCTTCA CCTTCGGCGT TGGCTCAGCT CGCATTGTGA TTCCTGGCGA CTACATTGAT
TTCGGCCCCA TCTCCACTGG AAGCTCGTCT TGCTTTGGCG GCATCCAGTC CAGCGCTGGT
ATCGGCATCA ACATCTTCGG TGATGTCGCT CTGAAGGCCG CCTTTGTCGT CTTCAACGGG
GCTACAACTC CCACTCTTGG CTTTGCTTCC AAG
```

8. The strain of claim 3, wherein said promoter is a *Cryphonectria parasitica* gene promoter.

```
AAGCTTATCC GCCGCCGGCG GGGGAATTCT ATTGAACTTG TTCGAATCAT TGGTCCGTGG
TCTTTTCGTC CATGCGGGCT CCGCTGGCGG ATGAATGACC TTCTGGCTTC TAGCCTGGCG
AAGCGATGTT ACTCTGTTGT CTATACTATA CGATATGGTC AAGAGAGCAC ATGTGCCGCC
AGATGAAGAC ATGTATATAA AAGGAGTGGC CTCGACGGTT GCTCAACCAT CTTCTGTCTG
```

```
TCCCAACGCC ATCGACTCTT CAACTTCTCC TTCGTGTTCC ACCACCATCA CCTTGCTCCA

GACTTAGGAC TTTCAGCAAC CTTCAAAG
``` which carries the TATA box and, upstream of said sequence, a segment comprised of fragment C and bounded by the 5'-Bam HI site and the Hind III site at the 5'-end of fragment A of FIG. 4, such that said segment contains an activator region.

14. The strain of claim 13, wherein segment X of fragment C comprises the following nucleic acid sequence (SEQ ID NO:6):

```
GCATGCTTGG CTCTTTAACG TCCTGCCCAT TCAGGGCCTT CAGCCGGCAC TGGTCCTTCA

TCAAGGGGGA CCTCATGACC ATGAACTAAT CTGTGATATC TGATATATTC TAGAAGGCTT

GGCTCCTCAA AGTTTCCAGC TAATGAATCA GCGGCCCGCC GCCCTTAAAC CGCATCAGGC

AAGTCGTTTG GTGTTGCCAG GCGATGGCGA CAGGAGAGTG GTGTTGATGG GACAAGGGGA

GGGAGGCTTA GCCGACTTCA TCCATAGCAC CCACCTGCTT GGCGCCGATA AGTCTGACGA

TCCGCTTGAG CTGCAAAACG GCTCCTTGAC CTTTGTTTGG TCGACCGAGG GAAATAGTCT

CTTTTTGCGT GATCGTGCGC GCTTCGTATA GCAATAGCAG CCAGCACCAG CAGGACGGGC

CGTTGTCACG GTCACATCGT TCGCAACATG CCGAGCGTAG GGATGAACGA ATGACTCGAG

CCTTGCCTGA CAGTCTGGCA ATCAATCTAT GGTCACGCAC GATCACAAGC CAATCGCTGT

GACTGCGTTA CTAGCCCAAT AATCCCTTGT TCGATCAGAG TGTTCTACAG ACTTCAAGTG

AGGTTCAC
```

15. The transformed strain according to claim 5, wherein said strain overproduces endothiapepsin when compared with SEBR103 by a factor of at least two.

16. A process for preparing endothiapepsin, wherein said process comprises (a) culturing an endothiapepsin-producing *Cryphonectria parasitica* strain, wherein said strain is transformed with a cassette for the expression of an endothiapepsin precursor of *Cryphonectria parasitica*, said cassette comprising a functional promoter upstream of a nucleic acid sequence coding for said precursor, wherein said precursor has the following amino acid sequence (P4) (SEQ ID NO:2):

```
                                Met Ser Ser Pro Leu Lys Asn Ala Leu

Val Thr Ala Met Leu Ala Gly Gly Ala Leu Ser Ser Pro Thr Lys Gln

His Val Gly Ile Pro Val Asn Ala Ser Pro Glu Val Gly Pro Gly Lys

Tyr Ser Phe Lys Gln Val Arg Asn Pro Asn Tyr Lys Phe Asn Gly Pro

Leu Ser Val Lys Lys Thr Tyr Leu Lys Tyr Gly Val Pro Ile Pro Ala

Trp Leu Glu Asp Ala Val Gln Asn Ser Thr Ser Gly Leu Ala Glu Arg

Ser Thr Gly Ser Ala Thr Thr Pro Ile Asp Ser Leu Asp Asp Ala

Tyr Ile Thr Pro Val Gln Ile Gly Thr Pro Ala Gln Thr Leu Asn Leu

Asp Phe Asp Thr Gly Ser Ser Asp Leu Trp Val Phe Ser Ser Glu Thr

Thr Ala Ser Glu Val Asp Gly Gln Thr Ile Tyr Thr Pro Ser Lys Ser

Thr Thr Ala Lys Leu Leu Ser Gly Ala Thr Trp Ser Ile Ser Tyr Gly

Asp Gly Ser Ser Ser Ser Gly Asp Val Tyr Thr Asp Thr Val Ser Val

Gly Gly Leu Thr Val Thr Gly Gln Ala Val Glu Ser Ala Lys Lys Val

Ser Ser Ser Phe Thr Glu Asp Ser Thr Ile Asp Gly Leu Leu Gly Leu

Ala Phe Ser Thr Leu Asn Thr Val Ser Pro Thr Gln Gln Lys Thr Phe

Phe Asp Asn Ala Lys Ala Ser Leu Asp Ser Pro Val Phe Thr Ala Asp

Leu Gly Tyr His Ala Pro Gly Thr Tyr Asn Phe Gly Phe Ile Asp Thr
```

```
Thr Ala Tyr Thr Gly Ser Ile Thr Tyr Thr Ala Val Ser Thr Lys Gln

Gly Phe Trp Glu Trp Thr Ser Thr Gly Tyr Ala Val Gly Ser Gly Thr

Phe Lys Ser Thr Ser Ile Asp Gly Ile Ala Asp Thr Gly Thr Thr Leu

Leu Tyr Leu Pro Ala Thr Val Val Ser Ala Tyr Trp Ala Gln Val Ser

Gly Ala Lys Ser Ser Ser Ser Val Gly Gly Tyr Val Phe Pro Cys Ser

Ala Thr Leu Pro Ser Phe Thr Phe Gly Val Gly Ser Ala Arg Ile Val

Ile Pro Gly Asp Tyr Ile Asp Phe Gly Pro Ile Ser Thr Gly Ser Ser

Ser Cys Phe Gly Gly Ile Gln Ser Ser Ala Gly Ile Gly Ile Asn Ile

Phe Gly Asp Val Ala Leu Lys Ala Ala Phe Val Val Phe Asn Gly Ala

Thr Thr Pro Thr Leu Gly Phe Ala Ser Lys
``` and wherein said strain overproduces endothiapepsin compared with *Cryphonectria parasitica,* followed by (b) isolation and purification of said endothiapepsin.

17. A process for obtaining an endothiapepsin-producing *Cryphonectria parasitica* strain, wherein said strain is transformed with a cassette for the expression of an endothiapepsin precursor of *Cryphonectria parasitica*, said cassette comprising a functional promoter upstream of a nucleic acid sequence coding for said precursor, wherein endothiapepsin has the following amino acid sequence (PI) (SEQ ID NO:1):

```
Ser Thr Gly Ser Ala Thr Thr Thr Pro Ile Asp Ser Leu Asp Asp Ala

Tyr Ile Thr Pro Val Gln Ile Gly Thr Pro Ala Gln Thr Leu Asn Leu

Asp Phe Asp Thr Gly Ser Ser Asp Leu Trp Val Phe Ser Ser Glu Thr

Thr Ala Ser Glu Val Asp Gly Gln Thr Ile Tyr Thr Pro Ser Lys Ser

Thr Thr Ala Lys Leu Leu Ser Gly Ala Thr Trp Ser Ile Ser Tyr Gly

Asp Gly Ser Ser Ser Gly Asp Val Tyr Thr Asp Thr Val Ser Val

Gly Gly Leu Thr Val Thr Gly Gln Ala Val Glu Ser Ala Lys Lys Val

Ser Ser Ser Phe Thr Glu Asp Ser Thr Ile Asp Gly Leu Leu Gly Leu

Ala Phe Ser Thr Leu Asn Thr Val Ser Pro Thr Gln Gln Lys Thr Phe

Phe Asp Asn Ala Lys Ala Ser Leu Asp Ser Pro Val Phe Thr Ala Asp

Leu Gly Tyr His Ala Pro Gly Thr Tyr Asn Phe Gly Phe Ile Asp Thr

Thr Ala Tyr Thr Gly Ser Ile Thr Tyr Thr Ala Val Ser Thr Lys Gln

Gly Phe Trp Glu Trp Thr Ser Thr Gly Tyr Ala Val Gly Ser Gly Thr

Phe Lys Ser Thr Ser Ile Asp Gly Ile Ala Asp Thr Gly Thr Thr Leu

Leu Tyr Leu Pro Ala Thr Val Val Ser Ala Tyr Trp Ala Gln Val Ser

Gly Ala Lys Ser Ser Ser Ser Val Gly Gly Tyr Val Phe Pro Cys Ser

Ala Thr Leu Pro Ser Phe Thr Phe Gly Val Gly Ser Ala Arg Ile Val

Ile Pro Gly Asp Tyr Ile Asp Phe Gly Pro Ile Ser Thr Gly Ser Ser

Ser Cys Phe Gly Gly Ile Gln Ser Ser Ala Gly Ile Gly Ile Asn Ile

Phe Gly Asp Val Ala Leu Lys Ala Ala Phe Val Val Phe Asn Gly Ala

Thr Thr Pro Thr Leu Gly Phe Ala Ser Lys
``` and wherein said strain overproduces endothiapepsin compared with *Cryphonectria parasitica,* comprising (a) at least one cycle of cotransformation of mycelium protoplasts with said cassette and a dominant selection marker, followed by (b) purification by sporulation wherein said marker is removed.

18. The process of claim 17, wherein said process comprises two cycles of cotransformation before said purification.

* * * * *